United States Patent
Zhao et al.

(10) Patent No.: US 9,994,556 B2
(45) Date of Patent: Jun. 12, 2018

(54) TRIAZOLE MODIFIED COUMARIN AND BIPHENYL AMIDE-BASED HSP90 INHIBITORS

(71) Applicant: THE UNIVERSITY OF KANSAS, Lawrence, KS (US)

(72) Inventors: Jinbo Zhao, Lawrence, KS (US); Huiping Zhao, East Brunswick, NJ (US); Brian S. J. Blagg, Lawrence, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 0 days. days.

(21) Appl. No.: 15/318,351

(22) PCT Filed: Jun. 12, 2015

(86) PCT No.: PCT/US2015/035691
§ 371 (c)(1),
(2) Date: Dec. 12, 2016

(87) PCT Pub. No.: WO2015/192099
PCT Pub. Date: Dec. 17, 2015

(65) Prior Publication Data
US 2017/0253582 A1    Sep. 7, 2017

Related U.S. Application Data

(60) Provisional application No. 62/012,071, filed on Jun. 13, 2014.

(51) Int. Cl.
C07D 405/14    (2006.01)
C07D 401/12    (2006.01)

(52) U.S. Cl.
CPC ......... *C07D 405/14* (2013.01); *C07D 401/12* (2013.01)

(58) Field of Classification Search
None
See application file for complete search history.

(56) References Cited

U.S. PATENT DOCUMENTS

| | | |
|---|---|---|
| 7,608,594 B2 | 10/2009 | Blagg et al. |
| 7,622,451 B2 | 11/2009 | Blagg et al. |
| 7,811,998 B2 | 10/2010 | Blagg et al. |
| 7,960,353 B2 | 6/2011 | Blagg |
| 8,212,011 B2 | 7/2012 | Blagg |
| 8,212,012 B2 | 7/2012 | Blagg |
| 9,056,104 B2 | 6/2015 | Blagg et al. |
| 9,120,774 B2 | 9/2015 | Blagg et al. |
| 9,422,320 B2 | 8/2016 | Blagg et al. |
| 2006/0199776 A1 | 9/2006 | Blagg et al. |
| 2007/0270452 A1 | 11/2007 | Blagg et al. |
| 2009/0163709 A1 | 6/2009 | Blagg |
| 2009/0187014 A1 | 7/2009 | Blagg |
| 2010/0048882 A1 | 2/2010 | Blagg et al. |
| 2010/0105630 A1 | 4/2010 | Blagg |
| 2012/0252745 A1 | 10/2012 | Blagg et al. |
| 2012/0309702 A1 | 12/2012 | Blagg et al. |

FOREIGN PATENT DOCUMENTS

| | | | | |
|---|---|---|---|---|
| WO | WO 2006/050501 | | 5/2006 | |
| WO | WO 2010/096650 | | 8/2010 | |
| WO | WO 2010/096650 A1 | * | 8/2010 | ............ C07H 17/06 |
| WO | WO 2011/041593 | | 4/2011 | |
| WO | WO 2012/162054 | | 11/2012 | |
| WO | WO 2015/200514 | | 12/2015 | |

OTHER PUBLICATIONS

Anyika et al., "Development of Noviomimetics as C-Terminal Hsp90 Inhibitors", *ACS Medicinal Chemistry Letters*, 7: 67-71, 2016.

Burlison et al., "Development of Novobiocin Analogues That Manifest Anti-proliferative Activity against Several Cancer Cell Lines," *J. Org. Chem.*, 73:2130, 2008.

Burlison, et al., "Novobiocin: Redesigning a DNA Gyrase Inhibitor for Selective Inhibition of Hsp90," *J. Am. Chem. Soc.*, 128:15529, 2006.

Donnelly, et al., "Cytotoxic sugar analogues of an optimized novobiocin scaffold," *MedChemComm*, 1(2):165-170, 2010.

Huang, et al., "Molecular Design of Anticancer Drug Leads Based on Three-Dimensional Quantitative Structure-Activity Relationship," *J. Chem. Info. Modeling*, 51(8):1999-2006, 2011.

Huang and Blagg, "A library of noviosylated coumarin analogues," *J. Org. Chem.*, 72(10):3609-3613, 2007.

(Continued)

*Primary Examiner* — Brian J Davis
(74) *Attorney, Agent, or Firm* — Parker Highlander PLLC

(57) ABSTRACT

Provided herein are compounds of the formulas: which are 90-kDa heat shock protein inhibitors. Pharmaceutical compositions of the compounds are also provided. In some aspects, these compounds may be used for the treatment of diseases, including cancer, e.g., cancers of the breast, the prostate, and the head & neck.

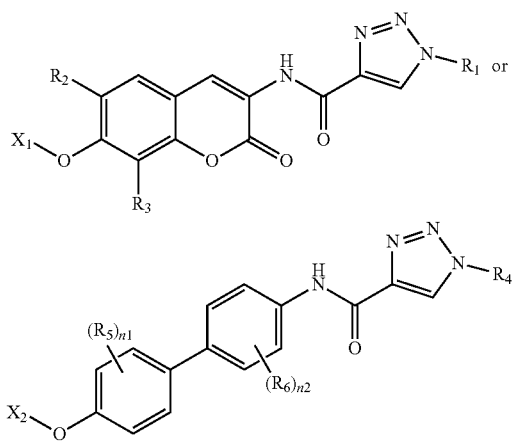

20 Claims, 3 Drawing Sheets

(56) References Cited

OTHER PUBLICATIONS

International Preliminary Report on Patentability issued in corresponding PCT Application No. PCT/US2015/035691, dated Jun. 13, 2014.
International Search Report and Written Opinion issued in corresponding PCT Application No. PCT/US2015/035691, dated Sep. 11, 2015.
Jhaveri, et al., "Advances in the Clinical Development of Heat Shock Protein 90 (Hsp90) Inhibitors in Cancer," *Biochimica et Biophysica Acta—Molecular Cell Research*, 1823(3):742-755, 2012.
Kusuma et al., "Synthesis and Biological Evaluation of Coumarin Replacements of Novobiocin as Hsp90 Inhibitors," *Bioorg. Med. Chem.*, 22(4):1441-1449, 2014.
Marcu, et al., "Novobiocin and Related Coumarins and Depletion of Heat Shock Protein 90-Dependent Signaling Proteins," *J. Natl. Cancer Inst.*, 92:242-248, 2000.
Matts et al., "Elucidation of the Hsp90 C-Terminal Inhibitor Binding Site," *ACS Chem. Biol.*, 6:800-807, 2011.
Peterson and Blagg, "Click chemistry to probe Hsp90: Synthesis and evaluation of a series of triazole-containing novobiocin analogues," *Bioorg Med. Chem. Lett.*, 20:3957-3960, 2010.
Shen et al., "Synthesis of photolabile novobiocin analogues," *Bioorg Med Chem Lett.*, 14(23):5903-6, 2004.
Yu et al., "Hsp90 Inhibitors Identified from a Library of Novobiocin Analogues," *J. Am. Chem. Soc.*, 127:12778, 2005.
Yun et al., "Novobiocin Induces a Distinct Conformation of Hsp90 and Alters Hsp90—Cochaperone—Client Interactions," *Biochemistry*, 43:8217-8229, 2004.
Zhao and Blagg, "Novobiocin analogues with second-generation noviose surrogates," *Bioorg & Med. Chem. Lett.*, 23(2):552-557, 2013.
Zhao et al., "Design, Synthesis, and Biological Evaluation of Biphenylamide Derivatives as Hsp90 C-terminal Inhibitors," *European Journal of Medicinal Chemistry*, 89:442-466, 2014.
Zhao et al., "Engineering an Antibiotic to Fight Cancer: Optimization of the Novobiocin Scaffold to Produce Anti-proliferative Agents," *J. Med. Chem.*, 54:3839-3853, 2011.
Zhao et al., "3D-QSAR-assisted design, synthesis and evaluation of novobiocin analogues", *ACS Med Chem Lett.*, 4(1): 57-62, 2013.
Zhao et al., "Identification of a New Scaffold for Hsp90 C-Terminal Inhibition," *ACS Med. Chem. Lett.*, 5:84-88, 2014.
Zhao et al., "Triazole containing novobiocin and biphenyl amides as Hsp90 C-terminal inhibitors," *MedChemComm*, 5(9):1317, 2014.
Zhao et al., "Synthesis and Evaluation of Noviose Replacements on Novobiocin that Manifest Anti-proliferative Activity," *ACS Med. Chem. Lett.*, 1:311-315, 2010.

* cited by examiner

TRIAZOLE MODIFIED COUMARIN AND BIPHENYL AMIDE-BASED HSP90 INHIBITORS

This application is a national phase application under 35 U.S.C. § 371 of International Application No. PCT/US2015/035691, filed Jun. 12, 2015, which claims the benefit of U.S. Provisional Application 62/012,071, filed on Jun. 13, 2014, the entire content of which are incorporated herein by reference.

This invention was made with government support under CA120458 and CA167079 awarded by the National Institutes of Health. The government has certain rights in the invention.

BACKGROUND OF THE INVENTION

I. Field of the Invention

The present invention relates generally to the fields of biology, chemistry, and medicine. More particularly, it concerns compounds, compositions and methods for the treatment and prevention of diseases such as cancer and other proliferative diseases.

II. Description of Related Art

Neckers and coworkers reported that the DNA gyrase inhibitor, novobiocin, and related natural products bind the Hsp90 C-terminus nucleotide binding pocket with low affinity ($IC_{50} \sim 700$ µM) (Marcu, et al., 2000). Subsequent modifications to novobiocin, including to the coumarin scaffold and the benzamide side chain, led to several compounds with increased inhibitory activity (Yu, et al., 2005; Burlison, et al., 2006; Zhao, et al., 2010; Zhao, et al., 2011; Zhao and Blagg, 2013). Improved activities were also observed for analogues possessing a 2-indole (Burlison, et al., 2008), 3-indole (Peterson and Blagg, 2010) or a 4-methoxyphenyl (Zhao, et al., 2011) side chain. Further development of new novobiocin compounds continues to be of interest because the biological activity profiles of these compounds vary, the wide variety of potential diseases and disorders that may be treated or prevented with these compounds, and manufacturing and supply-chain related considerations.

SUMMARY OF THE INVENTION

The present disclosure provides triazole modified coumarin and biphenyl amide-based Hsp90 inhibitors, including novobiocin analogs with anti-proliferative properties, pharmaceutical compositions thereof, methods for their manufacture, and methods for their use.

In one aspect of the present disclosure, there are provided compounds of the formula:

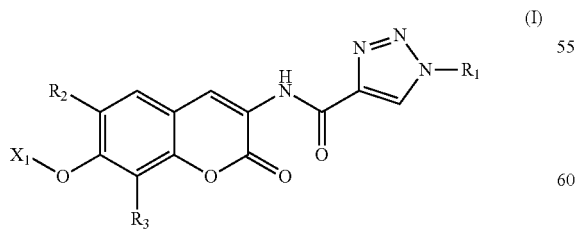

(I)

wherein:
R₁ is alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq8)}$-cycloalkyl$_{(C\leq12)}$, -alkanediyl$_{(C\leq8)}$-cycloalkenyl$_{(C\leq12)}$, or a substituted version of any of these groups;

R₂ is hydrogen, hydroxy, alkyl$_{(C\leq12)}$, substituted alkyl$_{(C\leq12)}$, cycloalkyl$_{(C\leq12)}$, substituted cycloalkyl$_{(C\leq12)}$, alkoxy$_{(C\leq12)}$, substituted alkoxy$_{(C\leq12)}$, cycloalkoxy$_{(C\leq12)}$, or substituted cycloalkoxy$_{(C\leq12)}$;

R₃ is hydrogen, alkyl$_{(C\leq12)}$, cycloalkyl$_{(C\leq12)}$, substituted alkyl$_{(C\leq12)}$, or substituted cycloalkyl$_{(C\leq12)}$; and X₁ is heterocycloalkyl$_{(C\leq12)}$ or substituted heterocycloalkyl$_{(C\leq12)}$.

In another aspect of the present disclosure, there are provided compounds of the formula:

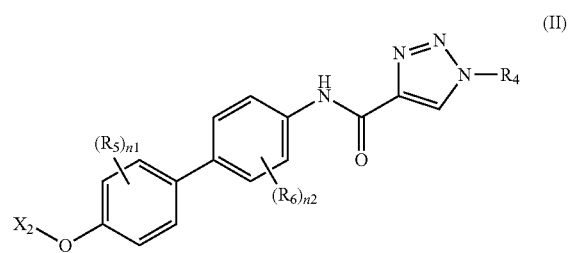

(II)

wherein:
R₄ is alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq8)}$-cycloalkyl$_{(C\leq12)}$, -alkanediyl$_{(C\leq8)}$-cycloalkenyl$_{(C\leq12)}$, or a substituted version of any of these groups;

R₅ and R₆ are each independently:
amino, cyano, halo, hydroxy, nitro, hydroxysulfonyl, or sulfonamide; or
alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, alkoxy$_{(C\leq12)}$, acyl$_{(C\leq12)}$, amido$_{(C\leq12)}$, alkylamino$_{(C\leq12)}$, dialkylamino$_{(C\leq12)}$, alkylsulfonyl$_{(C\leq12)}$, or a substituted version of any of these groups;

n₁ and n₂ are each independently 0, 1, 2, 3, or 4; and
X₂ is heterocycloalkyl$_{(C\leq12)}$ or substituted heterocycloalkyl$_{(C\leq12)}$;
or a pharmaceutically acceptable salt thereof. In some embodiments, the compounds are further defined as:

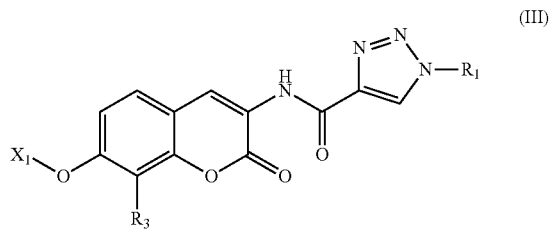

(III)

wherein:
R₁ is alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq8)}$-cycloalkyl$_{(C\leq12)}$, -alkanediyl$_{(C\leq8)}$-cycloalkenyl$_{(C\leq12)}$, or a substituted version of any of these groups;

R₃ is hydrogen, alkyl$_{(C\leq12)}$, or substituted alkyl$_{(C\leq12)}$; and
X₁ is heterocycloalkyl$_{(C\leq12)}$ or substituted heterocycloalkyl$_{(C\leq12)}$;
or a pharmaceutically acceptable salt thereof. In some embodiments, the compounds are further defined as:

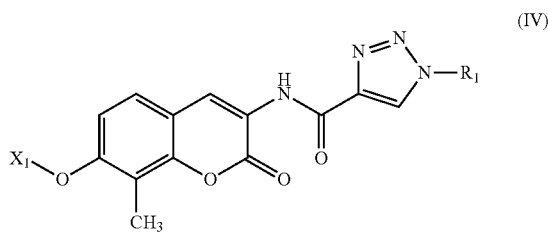

wherein:
R₁ is alkyl$_{(C≤12)}$, cycloalkyl$_{(C≤12)}$, alkenyl$_{(C≤12)}$, cycloalkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, -alkanediyl$_{(C≤8)}$-cycloalkyl$_{(C≤12)}$, -alkanediyl$_{(C≤8)}$-cycloalkenyl$_{(C≤12)}$, or a substituted version of any of these groups; and X₁ is heterocycloalkyl$_{(C≤12)}$ or substituted heterocycloalkyl$_{(C≤12)}$;

or a pharmaceutically acceptable salt thereof. In some embodiments, the compounds are further defined as:

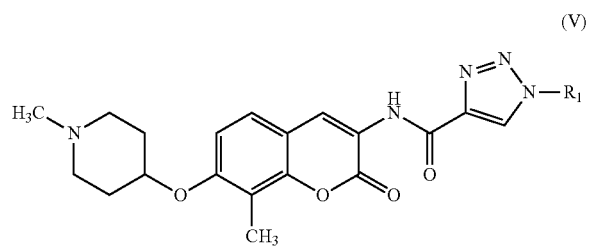

wherein:
R₁ is alkyl$_{(C≤12)}$, cycloalkyl$_{(C≤12)}$, alkenyl$_{(C≤12)}$, cycloalkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, or a substituted version of any of these groups; or -alkanediyl$_{(C≤8)}$-cycloalkyl$_{(C≤12)}$, -alkanediyl$_{(C≤8)}$-cycloalkenyl$_{(C≤12)}$, or a substituted version of this group;

or a pharmaceutically acceptable salt thereof. In other embodiments, the compounds are further defined as:

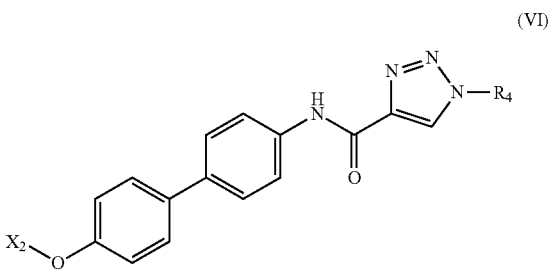

wherein:
R₄ is alkyl$_{(C≤12)}$, cycloalkyl$_{(C≤12)}$, alkenyl$_{(C≤12)}$, cycloalkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, -alkanediyl$_{(C≤8)}$-cycloalkyl$_{(C≤12)}$, -alkanediyl$_{(C≤8)}$-cycloalkenyl$_{(C≤12)}$, or a substituted version of any of these groups; and X₂ is heterocycloalkyl$_{(C≤12)}$ or substituted heterocycloalkyl$_{(C≤12)}$;

or a pharmaceutically acceptable salt thereof. In other embodiments, the compounds are further defined as:

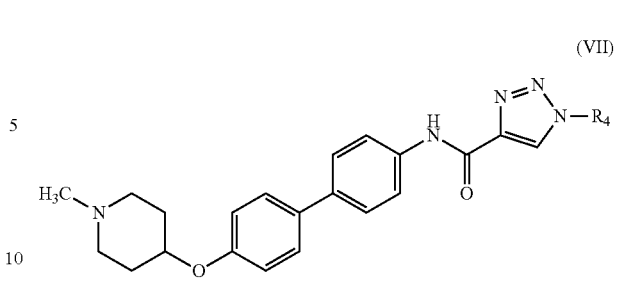

wherein:
R₄ is alkyl$_{(C≤12)}$, cycloalkyl$_{(C≤12)}$, alkenyl$_{(C≤12)}$, cycloalkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, -alkanediyl$_{(C≤8)}$-cycloalkyl$_{(C≤12)}$, -alkanediyl$_{(C≤8)}$-cycloalkenyl$_{(C≤12)}$, or a substituted version of any of these groups;

or a pharmaceutically acceptable salt thereof.

In some embodiments, R₁ is alkyl$_{(C≤12)}$ or substituted alkyl$_{(C≤12)}$. In other embodiments, R₁ is aryl$_{(C≤12)}$ or substituted aryl$_{(C≤12)}$. In some embodiments, R₁ is aryl$_{(C≤12)}$. In some embodiments, R₁ is phenyl or 4-methylphenyl. In other embodiments, R₁ is substituted aryl$_{(C≤12)}$. In some embodiments, R₁ is 3-chlorophenyl, 4-chlorophenyl, or 4-bromophenyl. In other embodiments, R₁ is aralkyl$_{(C≤12)}$ or substituted aralkyl$_{(C≤12)}$. In some embodiments, R₁ is aralkyl$_{(C≤12)}$. In some embodiments, R₁ is benzyl, 4-methylphenylmethyl, 4-t-butylphenylmethyl, 2-phenylethyl, or 3-phenylpropyl. In other embodiments, R₁ is substituted aralkyl$_{(C≤12)}$ In some embodiments, R₁ is 4-fluorophenylmethyl, 4-chlorophenylmethyl, 4-bromophenylmethyl, 4-methoxyphenylmethyl, 4-nitrophenylmethyl, 3-chlorophenylmethyl, 3-methoxyphenylmethyl, or 2-chlorophenylmethyl. In other embodiments, R₁ is -alkanediyl$_{(C≤8)}$-cycloalkyl$_{(C≤12)}$ or a substituted version of this group. In some embodiments, R₁ is —CH₂-cycloalkyl$_{(C≤12)}$. In some embodiments, R₁ is —CH₂C₆H₁₁.

In some embodiments, R₂ is hydrogen. In some embodiments, R₃ is alkyl$_{(C≤12)}$ or substituted alkyl$_{(C≤12)}$. In some embodiments, R₃ is alkyl$_{(C≤12)}$. In some embodiments, R₃ is methyl.

In some embodiments, X₁ is a nitrogen containing heterocycloalkyl$_{(C≤12)}$ or a substituted nitrogen containing heterocycloalkyl$_{(C≤12)}$. In some embodiments, X₁ is heterocycloalkyl$_{(C≤12)}$. In some embodiments, X₁ is:

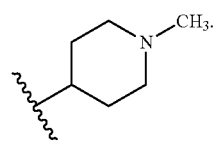 [SMILES: *C1CCN(C)CC1]

In some embodiments, R₄ is alkyl$_{(C≤12)}$ or substituted alkyl$_{(C≤12)}$. In other embodiments, R₄ is aryl$_{(C≤12)}$ or substituted aryl$_{(C≤12)}$. In some embodiments, R₄ is aryl$_{(C≤12)}$. In some embodiments, R₄ is phenyl. In other embodiments, R₄ is substituted aryl$_{(C≤12)}$. In other embodiments, R₄ is aralkyl$_{(C≤12)}$ or substituted aralkyl$_{(C≤12)}$. In some embodiments, R₄ is aralkyl$_{(C≤12)}$. In some embodiments, R₄ is benzyl, 4-methylphenylmethyl, 4-t-butylphenylmethyl, 3-methylphenylmethyl, 2-methylphenylmethyl, or 2-phenylethyl. In other embodiments, R₄ is substituted aralkyl$_{(C≤12)}$. In some embodiments, R₄ is 4-fluorophenylmethyl, 4-chlorophenylmethyl, 4-bromophenylmethyl, 4-methoxyphenylmethyl, 4-nitrophenylmethyl, 3-chlorophenylmethyl, 3-methoxyphenylmethyl, 2-chlorophenylmethyl, 2-chloro-4-methylphenylmethyl, 4-methylcarbamoylphenyl-methyl, methyl 4-carboxyphenylmethyl, 4-acetamidylphenylmethyl, 3-nitrophenylmethyl, 3-methylcarbamoylphenylmethyl, methyl 3-carboxyphenylmethyl, 3-acetamidylphenylmethyl, 2-hydroxyphenylmethyl, 2-methoxyphenylmethyl, 2-nitrophenylmethyl, or 2-methylcarbamoylphenylmethyl. In other embodiments, $R_4$ is -alkanediyl$_{(C \leq 8)}$-cycloalkyl$_{(C \leq 12)}$ or a substituted version of this group. In some embodiments, $R_4$ is —CH$_2$-cycloalkyl$_{(C \leq 12)}$. In some embodiments, $R_4$ is —CH$_2$C$_6$H$_{11}$.

In some embodiments, $n_1$ is 0 or 1. In some embodiments, $n_1$ is 0. In other embodiments, $n_1$ is 1. In some embodiments, $n_2$ is 0 or 1. In some embodiments, $n_2$ is 0. In other embodiments, $n_2$ is 1.

In some embodiments, $R_5$ is amino, cyano, halo, hydroxy, nitro, hydroxysulfonyl, or sulfonamide; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, alkoxy$_{(C \leq 12)}$, acyl$_{(C \leq 12)}$, amido$_{(C \leq 12)}$, alkylamino$_{(C \leq 12)}$, dialkylamino$_{(C \leq 12)}$, alkylsulfonyl$_{(C \leq 12)}$, or a substituted version of any of these groups.

In some embodiments, $R_6$ is amino, cyano, halo, hydroxy, nitro, hydroxysulfonyl, or sulfonamide; or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, alkoxy$_{(C \leq 12)}$, acyl$_{(C \leq 12)}$, amido$_{(C \leq 12)}$, alkylamino$_{(C \leq 12)}$, dialkylamino$_{(C \leq 12)}$, alkylsulfonyl$_{(C \leq 12)}$, or a substituted version of any of these groups.

In some embodiments, $X_2$ is a nitrogen containing heterocycloalkyl$_{(C \leq 12)}$ or a substituted nitrogen containing heterocycloalkyl$_{(C \leq 12)}$. In some embodiments, $X_2$ is heterocycloalkyl$_{(C \leq 12)}$. In some embodiments, $X_2$ is:

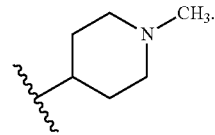 [SMILES: *C1CCN(C)CC1]

In some embodiments, the compound is further defined as:

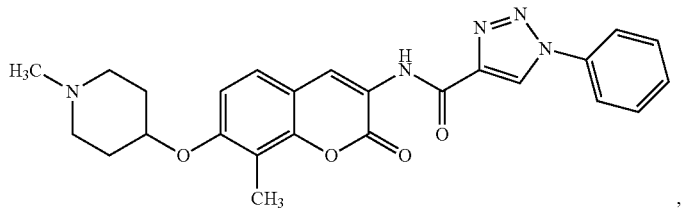

,

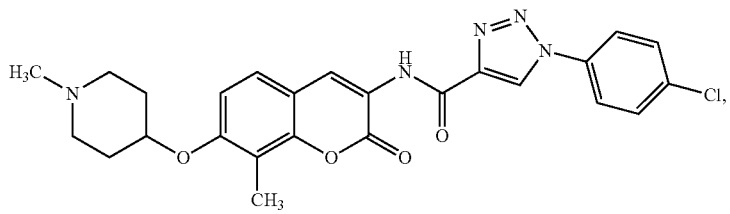

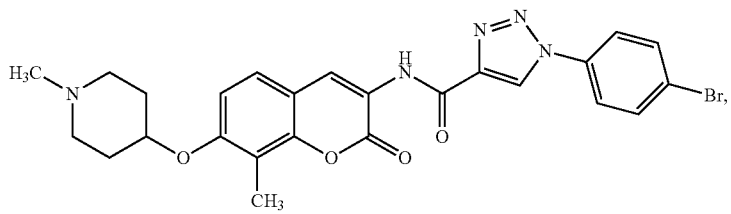

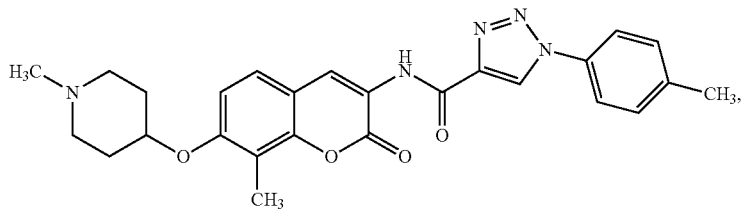

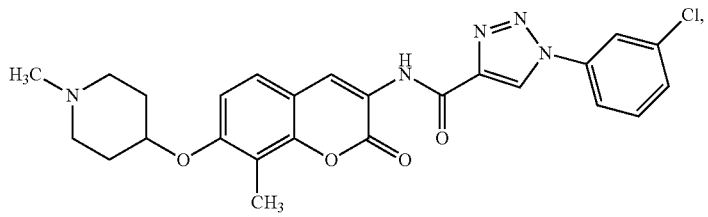

-continued
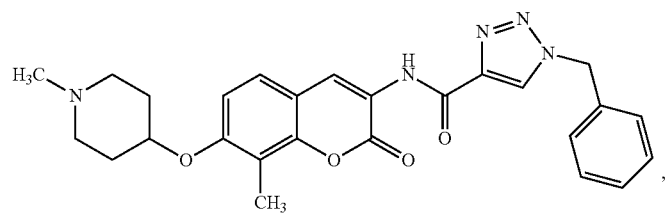
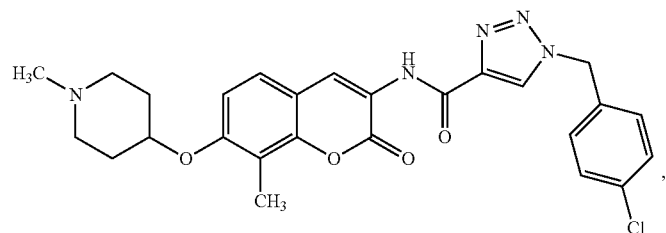
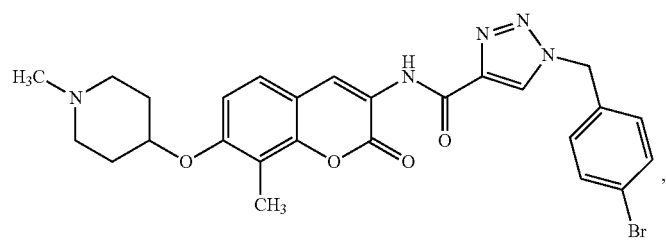
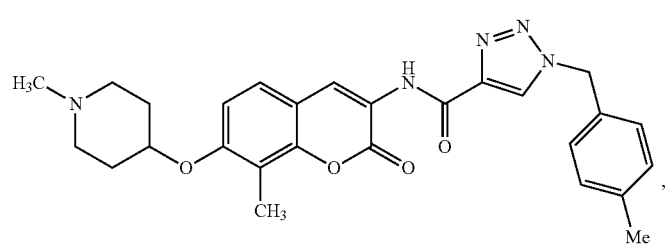
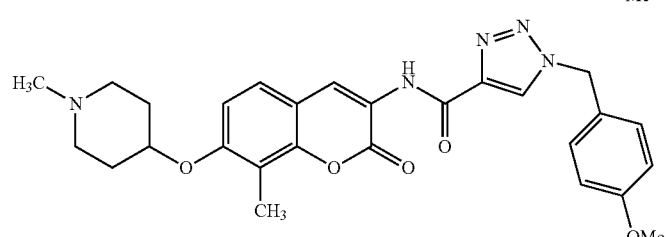
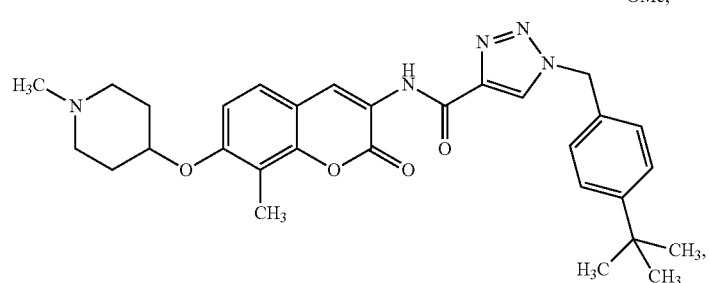
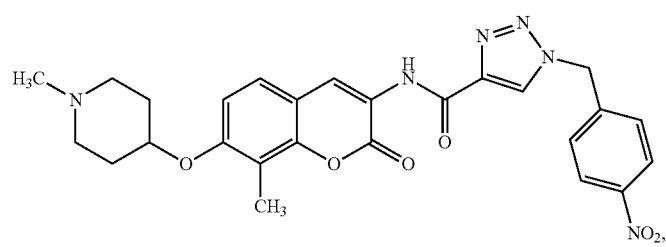

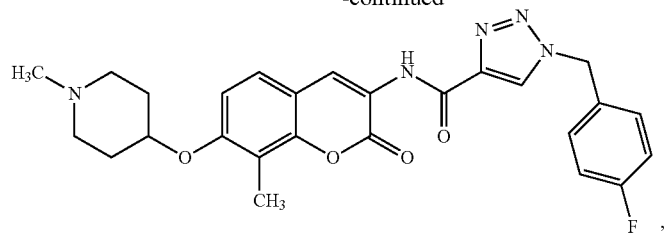
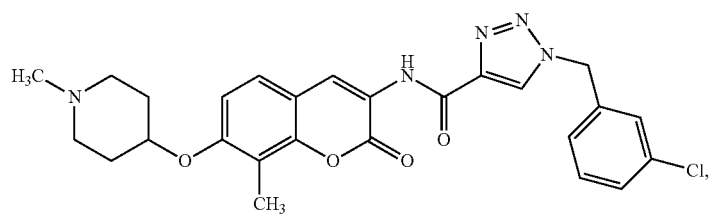
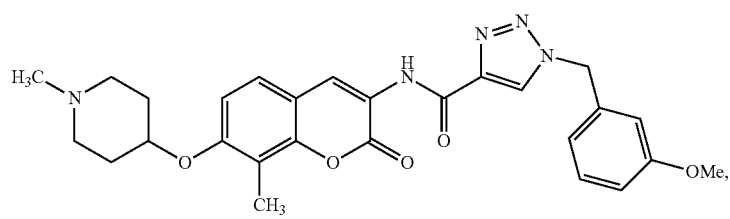
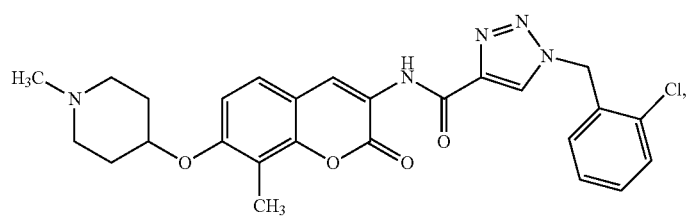
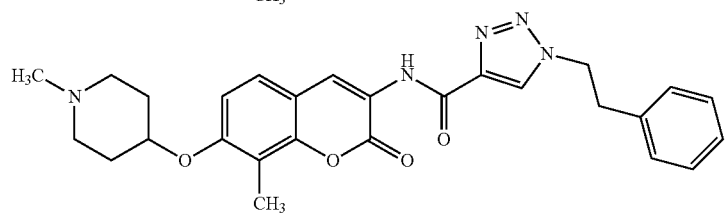
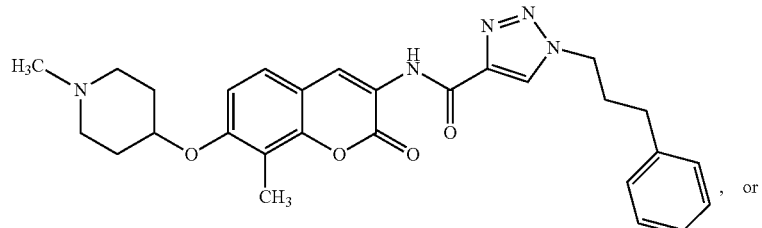
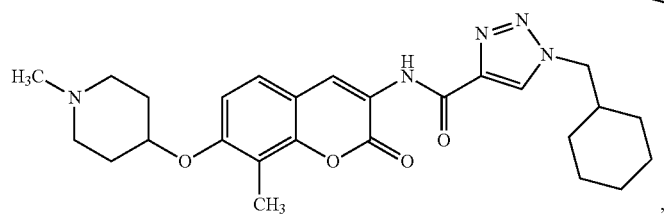
or a pharmaceutically acceptable salt of any of the above formulas.
In other embodiments, the compound is further defined as:

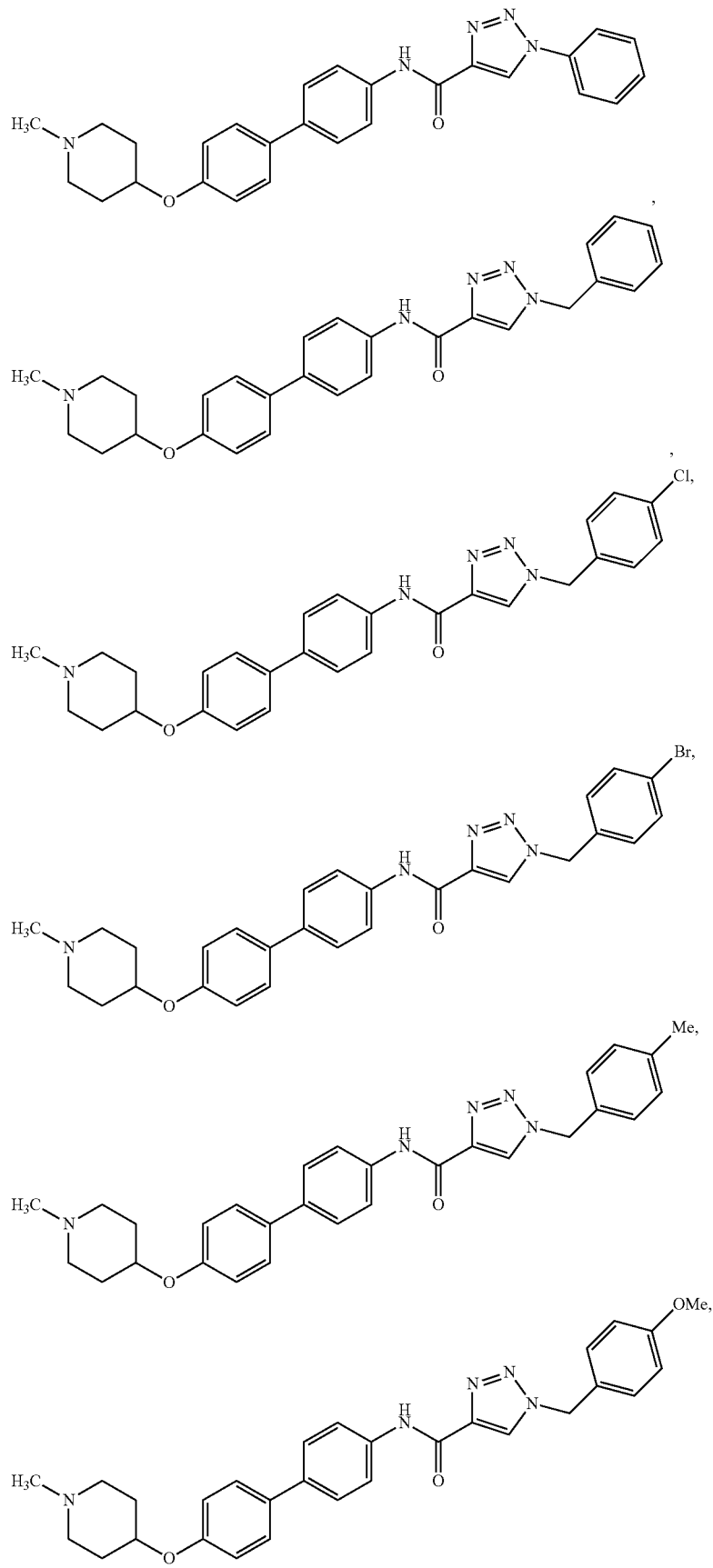 [SMILES: CN1CCC(Oc2ccc(-c3ccc(NC(=O)c4cn(-c5ccccc5)nn4)cc3)cc2)CC1 ; CN1CCC(Oc2ccc(-c3ccc(NC(=O)c4cn(Cc5ccccc5)nn4)cc3)cc2)CC1 ; CN1CCC(Oc2ccc(-c3ccc(NC(=O)c4cn(Cc5ccc(Cl)cc5)nn4)cc3)cc2)CC1 ; CN1CCC(Oc2ccc(-c3ccc(NC(=O)c4cn(Cc5ccc(Br)cc5)nn4)cc3)cc2)CC1 ; Cc1ccc(Cn2cc(C(=O)Nc3ccc(-c4ccc(OC5CCN(C)CC5)cc4)cc3)nn2)cc1 ; COc1ccc(Cn2cc(C(=O)Nc3ccc(-c4ccc(OC5CCN(C)CC5)cc4)cc3)nn2)cc1]

-continued
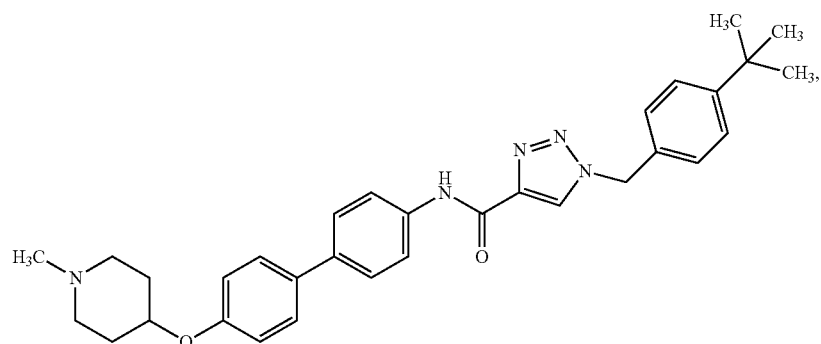
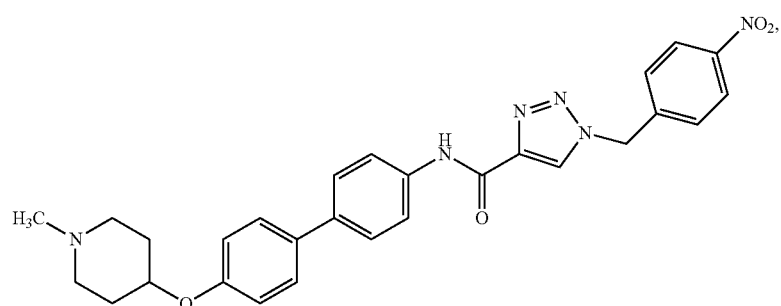
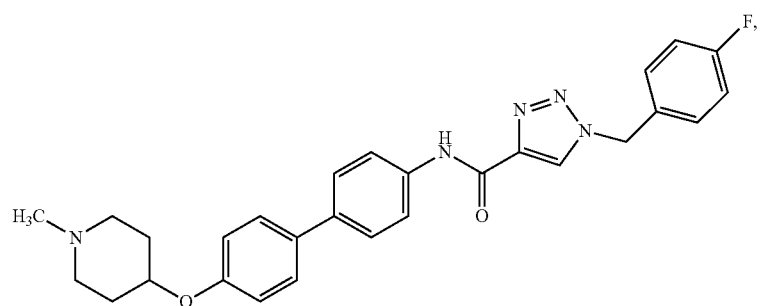
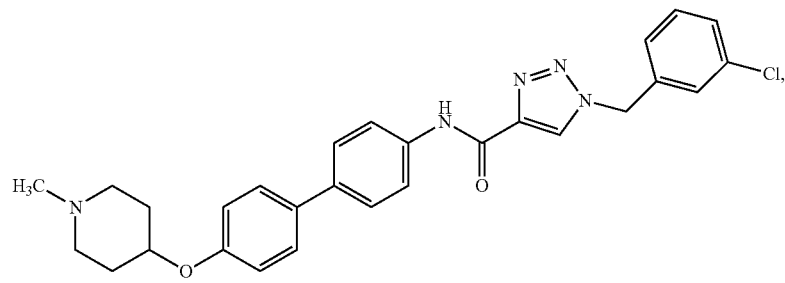
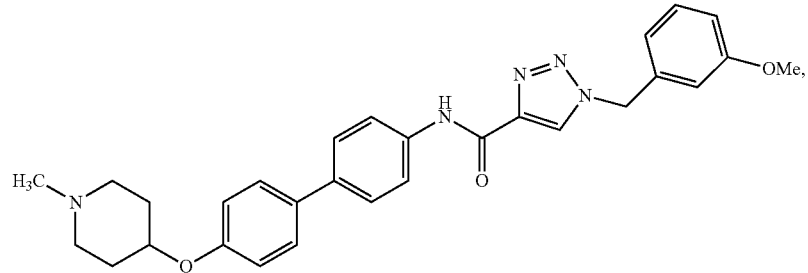

-continued
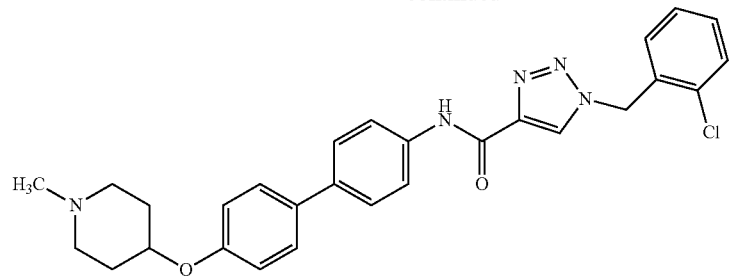
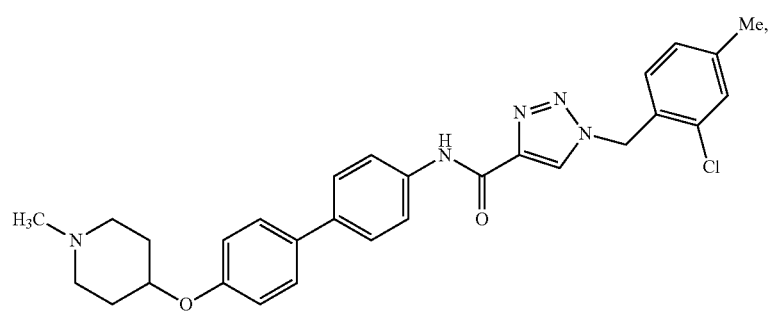
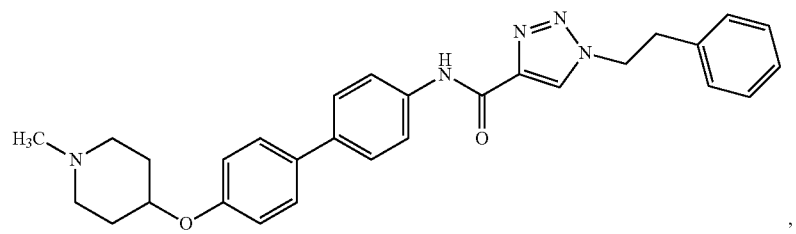
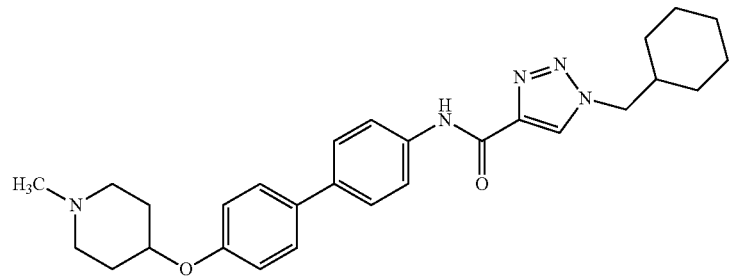
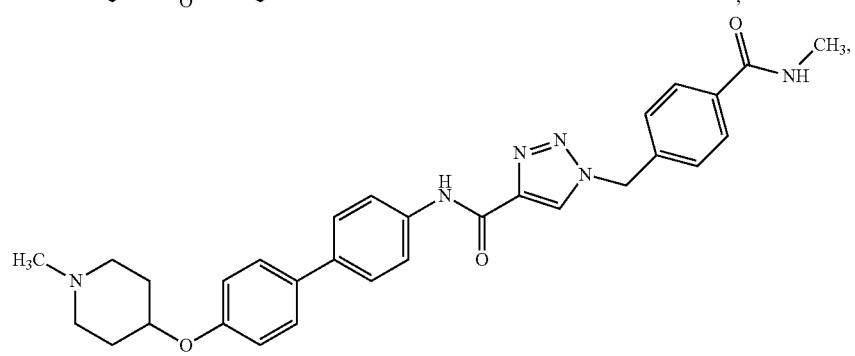

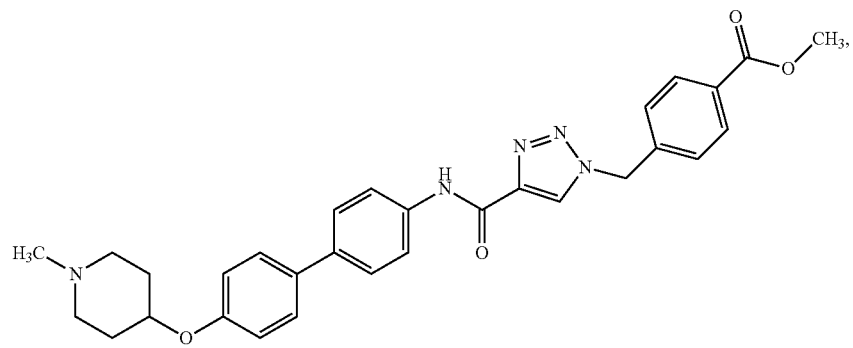
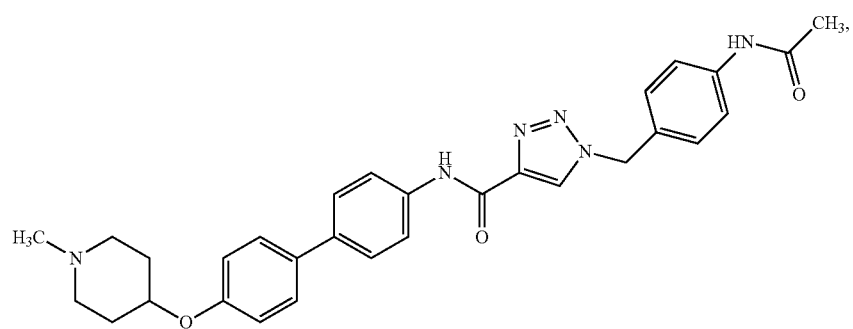
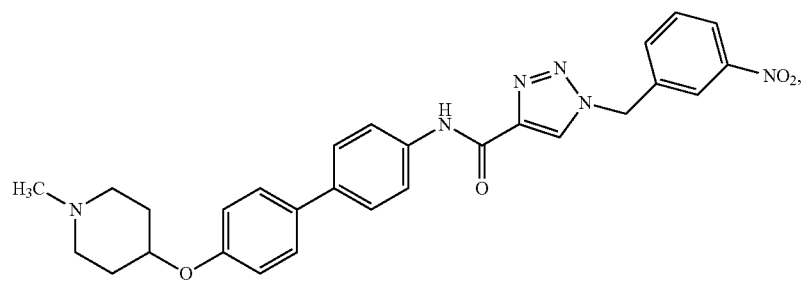
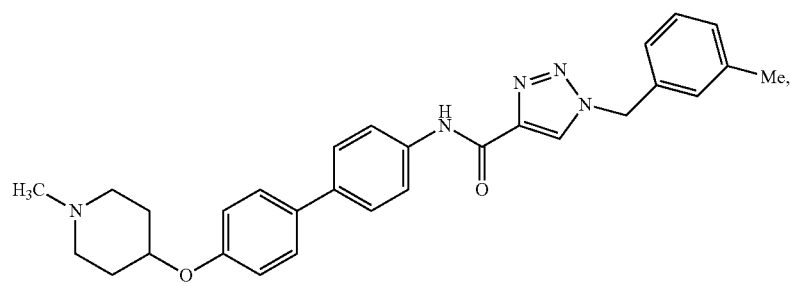
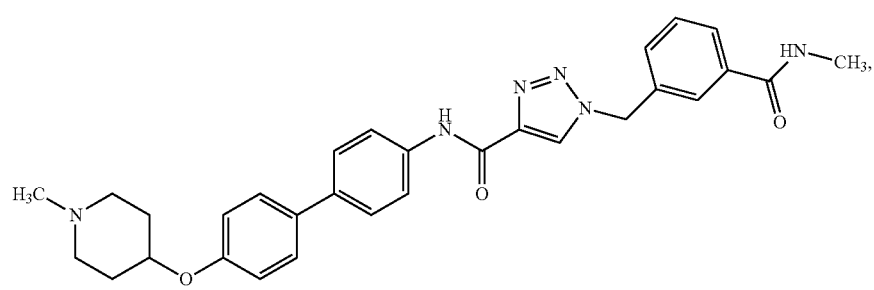

-continued
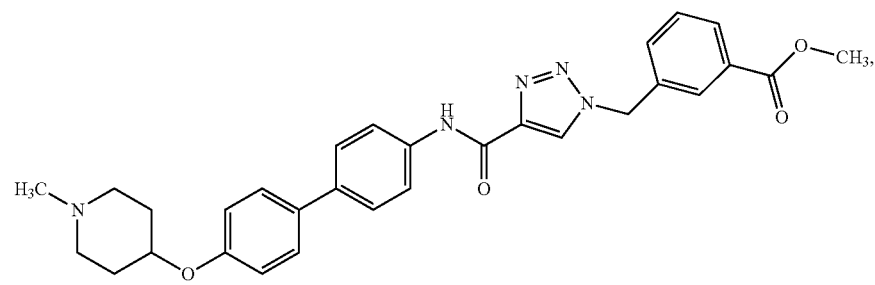
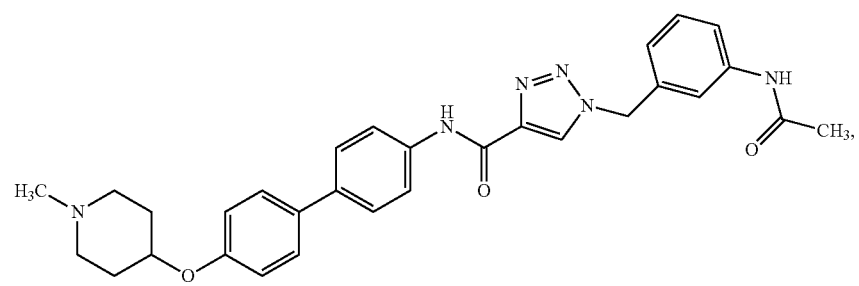
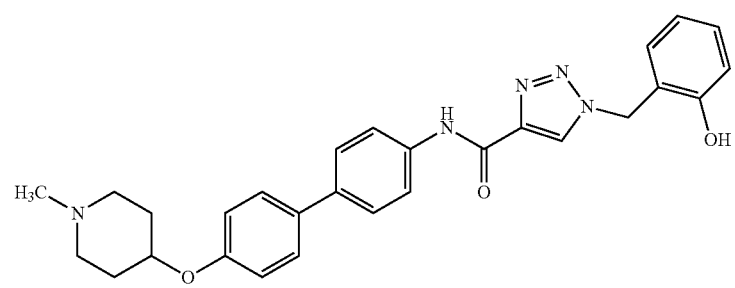
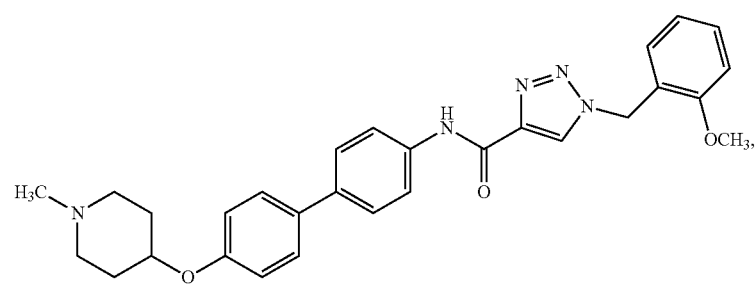
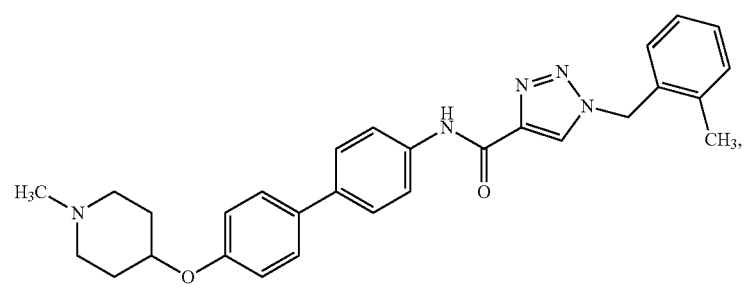
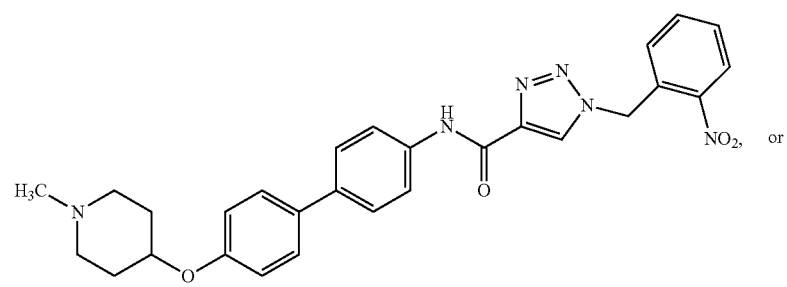

-continued

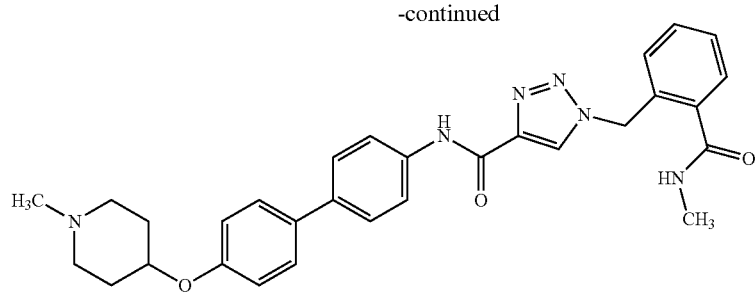

or a pharmaceutically acceptable salt of any of the above formulas.

In yet another aspect, the present disclosure provides pharmaceutical compositions comprising:
(A) a compound of the present disclosure; and
(B) a pharmaceutically acceptable carrier.

In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crmes, in lipid compositions, via a catheter, via a lavage, via continuous infusion, via infusion, via inhalation, via injection, via local delivery, or via localized perfusion. In some embodiments, the pharmaceutical composition is formulated for administration: orally, intraarterially, or intravenously. In some embodiments, the pharmaceutical composition is formulated as a unit dose.

In yet another aspect, the present disclosure provides methods of treating a disease or disorder in a patient comprising administering to the patient a therapeutically effective amount of a compound or composition of the present disclosure. In some embodiments, the disease or disorder is cancer. In some embodiments, the cancer is a carcinoma, sarcoma, lymphoma, leukemia, melanoma, mesothelioma, multiple myeloma, or seminoma. In some embodiments, the cancer is of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is breast cancer, head and neck cancer, or prostate cancer. In some embodiments, the head and neck cancer is a head and neck squamous cell carcinoma. In some embodiments, the methods further comprise administering the compound to the patient once. In other embodiments, the methods further comprise administering the compound to the patient two or more times. In some embodiments, the therapeutically effective amount is sufficient to induce apoptosis in a cancerous cell. In some embodiments, the therapeutically effective amount is sufficient to inhibit the growth of a cancerous cell.

In still yet another aspect, the present disclosure provides methods of inhibiting an Hsp90 protein comprising contacting the protein with a compound or composition of the present disclosure in an amount sufficient to decrease the activity of the protein. In some embodiments, the compound binds to the C-terminus of the Hsp90 protein. In some embodiments, the compound is sufficient to decrease the activity of the Hsp90 protein by more than 50%. In some embodiments, the activity is decreased by more than 80%. In some embodiments, the method is performed in vitro. In other embodiments, the method is performed in vivo.

In still yet another aspect, the present disclosure provides compounds comprising a structure of Formula 1, derivative thereof, prodrug thereof, salt thereof, or stereoisomer thereof, or having any chirality at any chiral center, or tautomer, polymorph, solvate, or combination thereof:

Formula 1

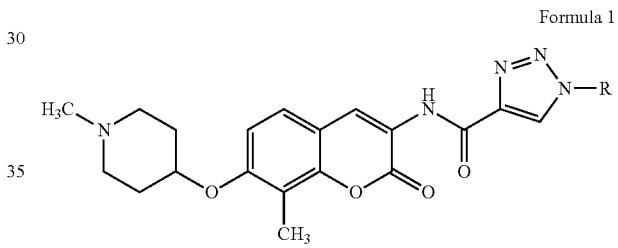

wherein R is any substituent. In some embodiments, the substituent is selected from substituents selected from the group of hydrogen, $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—(CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N⁺≡C⁻), cyanato (—O—C≡N), isocyanato (—O—N⁺≡C⁻), isothiocyanato (—S—C≡N), azido (—N=N⁺=N⁻), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR═N(aryl), where R═hydrogen, alkyl, aryl, alkaryl, etc.), nitro (—NO₂), nitroso (—NO), sulfo (—SO₂—OH), sulfonato (—S₂—O⁻)'C₁-C₂₄ alkylsulfanyl (—S-alkyl; also termed "alkylthio"), arylsulfanyl (—S-aryl; also termed "arylthio"), C₁-C₂₄ alkylsulfinyl (—(SO)-alkyl), C₅-C₂₀ arylsulfinyl (—(SO)-aryl), C₁-C₂₄ alkylsulfonyl (—SO₂-alkyl), C₅-C₂₀ arylsulfonyl (—SO₂-aryl), phosphono (—P(O)(OH)₂), phosphonato (—P(O)(O⁻)₂), phosphinato (—P(O)(O—)), phospho (—PO₂), phosphino (—PH₂), derivatives thereof, and combinations thereof.

In some embodiments, R is:

| | |
|---|---|
| Ph | 4a |
| Bn | 4b |
| 4-ClC₆H₅ | 4c |
| 4-BrC₆H₅ | 4d |
| 4-MeC₆H₅ | 4e |
| 3-ClC₆H₅ | 4f |
| 4-ClBn | 4g |
| 4-BrBn | 4h |
| 4-MeBn | 4i |
| 4-OMeBn | 4j |
| 4-t-BuBn | 4k |
| 4-NO₂Bn | 4l |
| 4-FBn | 4m |
| 3-ClBn | 4n |
| 3-OMeBn | 4o |
| 2-ClBn | 4p |
| CH₂Cy | 4q |
| Ph(CH₂)₂ | 4r |
| Ph(CH₂)₃ | 4s. |

In yet another aspect, the present disclosure provides compounds comprising a structure of Formula 2, derivative thereof, prodrug thereof, salt thereof, or stereoisomer thereof, or having any chirality at any chiral center, or tautomer, polymorph, solvate, or combination thereof:

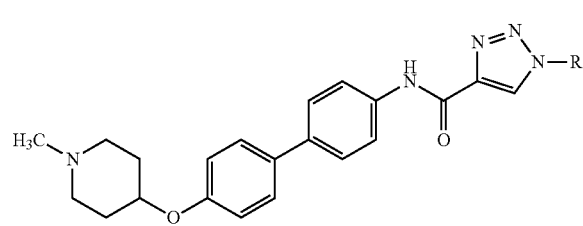

Formula 2 wherein R is any substituent. In some embodiments, the substituent is selected from substituents selected from the group of hydrogen, C₁-C₂₄ alkyl, C₂-C₂₄ alkenyl, C₂-C₂₄ alkynyl, C₅-C₂₀ aryl, C₆-C₂₄ alkaryl, C₆-C₂₄ aralkyl, halo, hydroxyl, sulfhydryl, C₁-C₂₄ alkoxy, C₂-C₂₄ alkenyloxy, C₂-C₂₄ alkynyloxy, C₅-C₂₀ aryloxy, acyl (including C₂-C₂₄ alkylcarbonyl (—CO-alkyl) and C₆-C₂₀ arylcarbonyl (—CO-aryl)), acyloxy (—O-acyl), C₂-C₂₄ alkoxycarbonyl (—(CO)—O-alkyl), C₆-C₂₀ aryloxycarbonyl (—(CO)—O-aryl), halocarbonyl (—(CO)—X where X is halo), C₂-C₂₄ alkylcarbonato (—O—(CO)—O-alkyl), C₆-C₂₀ arylcarbonato (—O—(CO)—O-aryl), carboxy (—COOH), carboxylato (—COO⁻), carbamoyl (—(CO)—NH₂), mono-(C₁-C₂₄ alkyl)-substituted carbamoyl (—(CO)—NH(C₁-C₂₄ alkyl)), di-(C₁-C₂₄ alkyl)-substituted carbamoyl (—(CO)—N(C₁-C₂₄ alkyl)₂), mono-substituted arylcarbamoyl (—(CO)—NH-aryl), thiocarbamoyl (—(CS)—NH₂), carbamido (—NH—(CO)—NH₂), cyano (—C≡N), isocyano (—N⁺≡C⁻), cyanato (—O—C≡N), isocyanato (—O—N⁺≡C⁻), isothiocyanato (—S—C≡N), azido (—N═N⁺═N⁻), formyl (—(CO)—H), thioformyl (—(CS)—H), amino (—NH₂), mono- and di-(C₁-C₂₄ alkyl)-substituted amino, mono- and di-(C₅-C₂₀ aryl)-substituted amino, C₂-C₂₄ alkylamido (—NH—(CO)-alkyl), C₆-C₂₀ arylamido (—NH—(CO)-aryl), imino (—CR═NH where R is hydrogen, C₁-C₂₄ alkyl, C₅-C₂₀ aryl, C₆-C₂₄ alkaryl, C₆-C₂₄ aralkyl, etc.), alkylimino (—CR═N(alkyl), where R═hydrogen, alkyl, aryl, alkaryl, aralkyl, etc.), arylimino (—CR═N(aryl), where R═hydrogen, alkyl, aryl, alkaryl, etc.), nitro (—NO₂), nitroso (—NO), sulfo (—SO₂—OH), sulfonato (—S₂—O⁻) 'C₁-C₂₄ alkylsulfanyl (—S-alkyl; also termed "alkylthio"), arylsulfanyl (—S-aryl; also termed "arylthio"), C₁-C₂₄ alkylsulfinyl (—(SO)-alkyl), C₅-C₂₀ arylsulfinyl (—(SO)-aryl), C₁-C₂₄ alkylsulfonyl (—SO₂-alkyl), C₅-C₂₀ arylsulfonyl (—SO₂-aryl), phosphono (—P(O)(OH)₂), phosphonato (—P(O)(O⁻)₂), phosphinato (—P(O)(O—)), phospho (—PO₂), phosphino (—PH₂), derivatives thereof, and combinations thereof.

In some embodiments, R is:

| | |
|---|---|
| Ph | 5a |
| Bn | 5b |
| (CH₂)₂Ph | 5c |
| 4-ClBn | 5d |
| 4-BrBn | 5e |
| 4-MeBn | 5f |
| 4-OMeBn | 5g |
| 4-t-BuBn | 5h |
| 4-NO₂Bn | 5i |
| 4-FBn | 5j |
| 3-ClBn | 5k |
| 3-MeOBn | 5l |
| 2-ClBn | 5m |
| 2-Cl,4-MeBn | 5n |
| CH₂Cy | 5o. |

In still yet another aspects, the present disclosure provides compounds comprising a structure of Formula 3 or 4, derivative thereof, prodrug thereof, salt thereof, or stereoisomer thereof, or having any chirality at any chiral center, or tautomer, polymorph, solvate, or combination thereof:

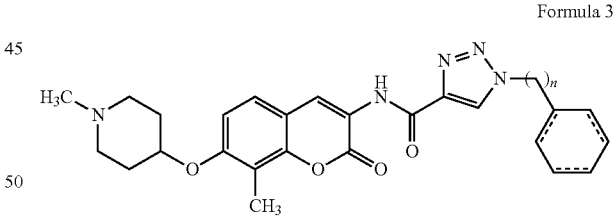

Formula 3

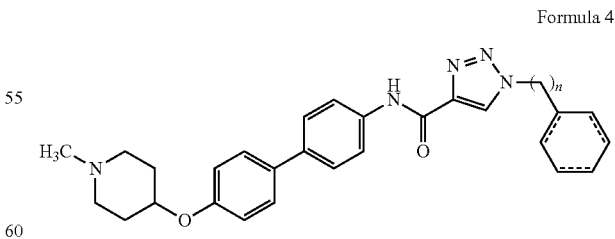

Formula 4 wherein the end ring can have an R substituent as any substituent, and n independently is any integer. In some embodiments, the R substituent is selected from substituents selected from the group of hydrogen, C₁-C₂₄ alkyl, C₂-C₂₄ alkenyl, C₂-C₂₄ alkynyl, C₅-C₂₀ aryl, C₆-C₂₄ alkaryl, C₆-C₂₄ aralkyl, halo, hydroxyl, sulfhydryl, C₁-C₂₄ alkoxy, C₂-C₂₄ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N$^+$≡C$^-$), cyanato (—O—C≡N), isocyanato (—O—N$^+$≡C$^-$), isothiocyanato (—S—C≡N), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—S$_2$—O$^-$)'$C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O—)), phospho (—PO$_2$), phosphino (—PH$_2$), derivatives thereof, and combinations thereof.

In yet another aspect, the present disclosure provides methods of inhibiting HSP90, the method comprising: providing a compound described herein to HSP90 in an amount sufficient to inhibit HSP90. In some embodiments, the compound is a HSP90 C-terminal inhibitor.

In still yet another aspect, the present disclosure provides methods of treating or inhibiting cancer, the method comprising: administering a compound of the present disclosure to a subject in need thereof. In some embodiments, the subject has or is susceptible to cancer. In some embodiments, inhibiting cancer is slowing the growth or propagation of cancer cells.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

(FIG. 2A) L represents a concentration ½ of the anti-proliferative IC$_{50}$ value, while H represents a concentration 5 times the antiproliferative IC$_{50}$ value. Clear degradation of Hsp90 client proteins Her2, Akt and Raf-1 was observed, while actin, which does not rely upon the Hsp90 chaperone machinery, remained constant, indicating that the antiproliferative activities manifested by these compounds resulted from Hsp90 inhibition. (FIG. 2B) Concentrations (in μM) of 5f are indicated above each lane. (FIG. 2C) Concentrations of 5b (in μM) are indicated above each lane. Geldanamycin (G, 500 nM) and DMSO (D) were employed respectively as positive and negative controls. These client proteins Her2, Akt, Raf-1 and CDK6 were also degraded in a concentration-dependent manner upon exposure to the most potent analogue 5f and the representative analogue 5b, against MCF-7 cells, while actin levels remain unchanged.

FIG. 3B shows results of the proteolysis of Hsp90 from TnT reticulocyte lysate incubated under conditions of protein synthesis with vehicle (1% DMSO) 5 mM novobiocin and 1 mM 5f. An antibody specific to the C-terminus of Hsp90 was used to identify the Hsp90 fragments produced in the presence of increasing amounts of trypsin. A 50 kDa band was detected with 5 mM novobiocin and 1 mM 5f that is not detected for the vehicle control.

DESCRIPTION OF ILLUSTRATIVE EMBODIMENTS

Figure 1:
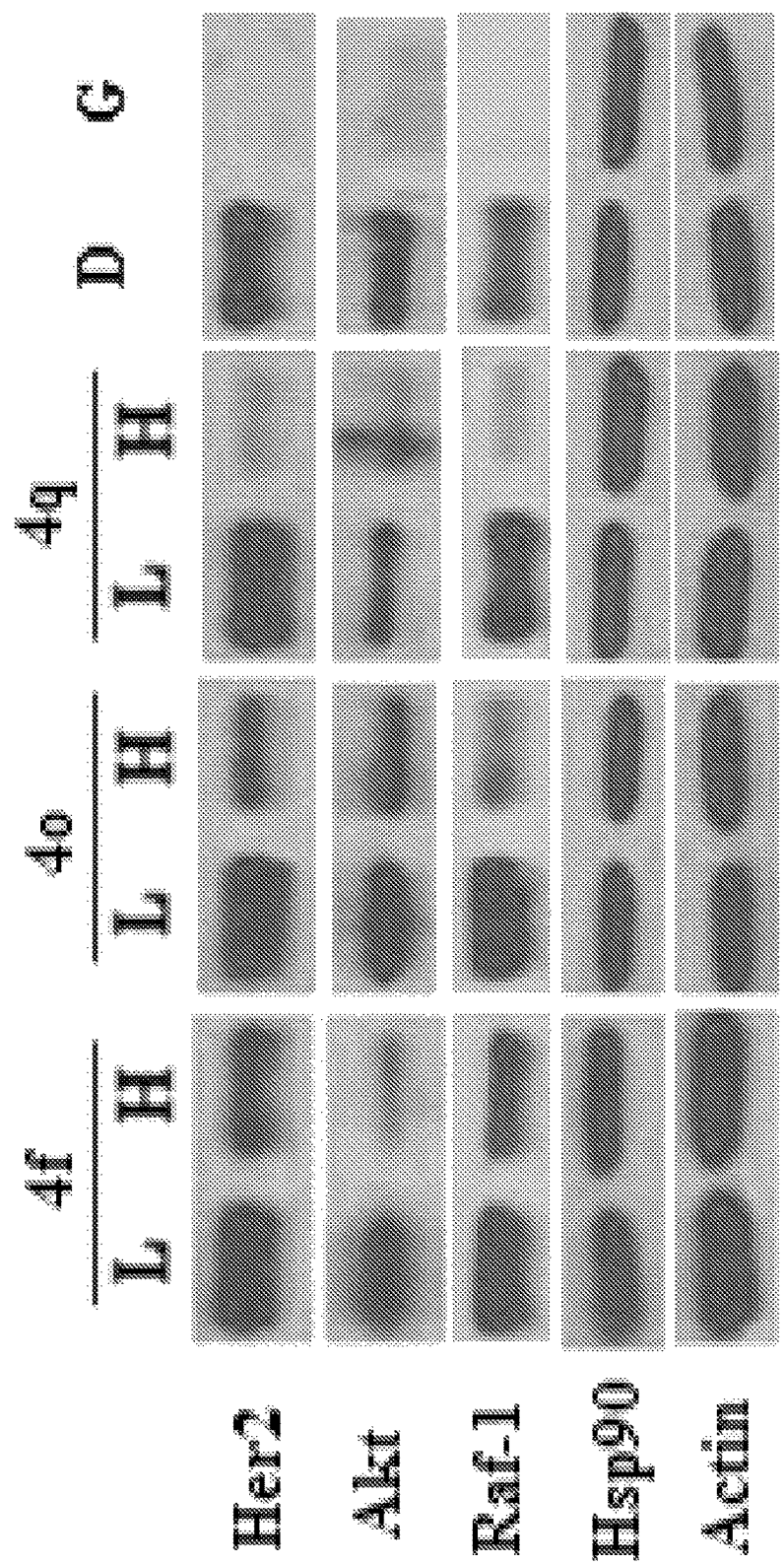
FIG. 1 shows the Western blot analyses of the Hsp90 client protein degradation in MCF-7 breast cancer cells lysis after treatment of triazole analogues. L represents a concentration ½ of the anti-proliferative IC$_{50}$ value, while H represents a concentration 5 times the antiproliferative IC$_{50}$ value. Geldanamycin (G, 500 nM) represents a positive control, while DMSO (D), vehicle, serves as the negative control. Hsp90 client proteins Her2, Akt and Raf-1 were degraded upon exposure of 4f, 4o or 4q at concentrations that mirror their anti-proliferative values, confirming that cell viability is directly linked to Hsp90 inhibition.

The present disclosure provides triazole modified coumarin and biphenyl amide-based Hsp90 inhibitors, including novobiocin analogs with anti-proliferative properties, pharmaceutical compositions thereof, methods for their manufacture, and methods for their use. In some embodiments, the compounds provided herein may be used as inhibitors of the c-terminus of the Hsp90 protein. The Hsp90 protein is associated with a variety of different target cellular processes that are misregulated in proliferative diseases, as well as other disorders. As such the compounds provided herein may be used to treat those proliferative diseases and other disorders. For example, the compounds described herein may be used to treat cancer such as breast cancer, head and neck cancer, and prostate cancer.

I. COMPOUNDS AND SYNTHETIC METHODS

The compounds provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein. In general, the starting materials may be prepared using the following methods:

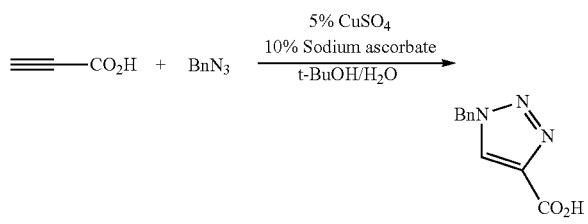

The process that may be used can be adopted from Kolarovic, et al., 2011 or other reports in the literature. In some embodiments, $CuSO_4$ (~0.05 equivalents), sodium ascorbate (~0.1 equivalent) and $H_2O$ was added to a reaction vessel. The mixture was then treated with an azide (~1.0 equivalents) and t-BuOH and then propiolic acid (~1.2 equivalents), the tube was sealed and the mixture was stirred overnight. The mixture was then added saturated $NaHCO_3$ solution, extracted with ether (twice). The organic layer was then discarded, and the aqueous layer was acidified with 1N $H_2SO_4$, and extracted with EtOAc (three times) and dried over $Na_2SO_4$. The solvent was evaporated to afford a triazole acid as a white solid. While in some embodiments, this triazole acid is further purified, in others, the prepared triazole acid is used without further purification. This acid may be then used to connect to the pharmacore of the molecule via any known amide coupling protocol. An exemplary protocol is outlined below and in the example section.

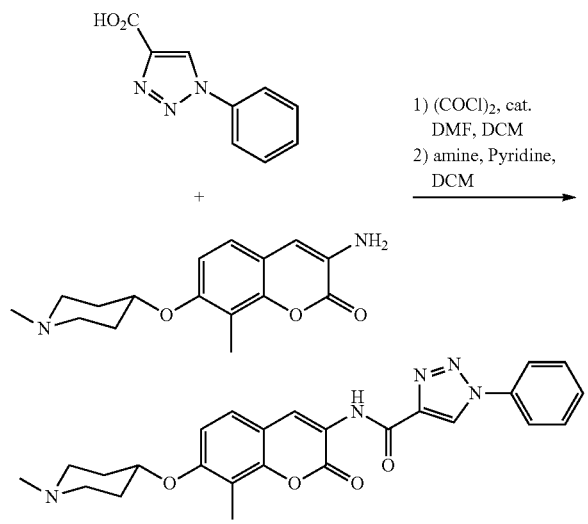

Oxalyl chloride ($(COCl)_2$) (~3 equivalents) and DMF under Ar were sequentially added to a solution of the triazole acid (~1 equivalent) in dry DCM was and the resulting solution was stirred at room temperature overnight to obtain the triazole acid chloride. Then the solvent was removed in vacuo and the residue was put on the high vacuum for 30 min. In a separate vessel, the amine (0.5 equivalents), dry DCM and pyridine (5 equivalents) were added. To the above solution was added a solution of the triazole acid chloride in dry DCM via a syringe dropwise. After addition the solution was stirred at room temperature overnight and purified to obtain the desired final product.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

II. HSP90 PROTEIN AND HYPERPROLIFERATIVE DISEASES

The compound of the present disclosure may be used in the treatment of diseases or disorders with result from the unnatural proliferation of cells. In some aspects, this disease or disorder is cancer. Without being bound by theory, in some embodiments, the compounds of the present disclosure bind to the C terminus of the Hsp90 protein and thus prevent the binding of the natural substrate to the protein. The Hsp90 is a molecular chaperone protein, which in addition to assisting in protein folding, protein degradation, and mitigating heat stress, is implicated in stabilizing a number of proteins associated with cancer. Inhibition of the Hsp90 protein has been shown to lead to apoptosis of the cancerous cells. Without being bound by theory, a number of different molecular pathways are implicated in the Hsp90 protein's role in cancer development and proliferation. For example, the protein is implicated in stabilizing mutant oncogenic proteins such as v-Src, Bcr/Abl, and p53, stabilizing several growth factors and signaling molecules such as EGFR, PI3K, and AKT proteins which leads to growth factor signaling pathway promotion, and promotes the induction of VEGF, nitric oxide synthase, and the matrix metalloproteinase MMP2 which promote angiogenesis and metathesis of the cancerous cells. Many different cancer types and subtypes rely on pathways mediated by the Hsp90 protein for proliferation and tumor development thus inhibitors of the highly conserved Hsp90 protein may be used to treat a wide variety of cancers.

The compound may be used to treat cancer cells according to the embodiments include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

In some embodiments, the compounds provided herein preventing the proliferation and/or causing apoptosis in the cancers associate with the following cell lines: SKBr3, MCF-7, MDA-MB-468LN, MDA1986, JMAR, PC3-MM2, and LNCaP.

SKBr3 is a human derived breast cancer cell. The cell line is an adenocarcinoma which presents with an epithelial morphology and the cell line overexpresses the HER2/c- erb-2 gene product. The SKBr3 cell line is negative for both progesterone and estrogen receptors. MCF-7 (or MCF7) is also a human breast cancer cell which overexpresses both progesterone and estrogen receptors while not overexpressing the HER2 protein. The cell line is adenocarcinoma which presents with an epithelial morphology. Furthermore, this cell line also expresses insulin-like growth factor binding proteins (IGFBP), BP-2, BP-4, and BP-5 as well as the associated proteins. The MCF-7 cell retains the ability to process estradiol via cytoplasmic estrogen receptors and growth of the cell line is known to be inhibited by tumor necrosis factor alpha (TNFα). The MDA-MB-468 cell line and its daughter cell lines are known to be an aggressive cell line. In particular the MDA-MB-468LN cell line originates in a human breast cancer adenocarcinoma cell line originating in the lymph nodes. MDA-MB-468 is also routinely used as model of triple negative breast cancer. As with triple negative breast cancer cell lines, the cell line does not express progesterone receptors, estrogen receptors, or the HER2 protein. The cell line also expresses epidermal growth factor (EGF) and transforming growth factor α (TGFα). More characterization of breast cancer cell lines is included in Lacroix and Leclercq, 2004, Neve, et al., 2006; Chavez, et al., 2010; and ATCC product description of these cell lines, which are all incorporated herein by reference.

The MDA1986 cell line originates as a cervical nodal metastasis of tongue cancer. The JMAR cell line (a TU167 cell line derivative) is derived from an invasive oral squamous cell carcinoma which has been modified to generate a cell line which is resistant to anoikis. The cell line also displays aggressive local growth and has been shown in animal models to metastasize to the cervical lymph nodes. The JMAR cell line expresses both the PTEN/MMAC1 and the HER-2/neu gene products but does not exhibit autocrine EFG/transforming growth factor α stimulation. Both of these cell lines have been extensively characterized and this characterization is reported in Lansford, et al., 1999, which is incorporated herein by reference.

The LNCaP and PC3-MM2 cell lines are both prostate cell lines which are derived from metastatic sites in the lymph nodes and bone of a prostate adenocarcinoma, respectively. The LNCaP cell line is androgen and estrogen sensitive expressing both androgen and estrogen receptors. The cells also express the prostate specific antigen resulting in increased expression of the prostate-specific membrane antigen. These cells are also known to be less prone to metastasis than other prostate cell lines. More characterization of the LNCaP cell line can be found in Horoszewicz, et al., 1983. On the other hand, the PC3-MM2 cell line has a high metastatic potential and is known for its propensity to metastasize to the bones. PC3-MM2 is also androgen and estrogen insensitive resulting in low activity from testosterone-5-alpha reductase and acidic phosphatase activity and low expression of androgen and estrogen receptors. The cell line also does not express the prostate specific antigen and is negative for the prostate specific membrane antigen. Additionally, this cell line often results from cells that are nearly triploid with 62 chromosomes. This cell line also does not express the PTEN gene. The PC3 cell line has been characterized and the characterization can be found in Kaighn, et al., 2012, and Sobel and Sadar, 2005, both of which are incorporated herein by reference.

III. PHARMACEUTICAL FORMULATIONS AND ROUTES OF ADMINISTRATION

The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compounds by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compounds into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compounds may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, the effective dosing amount that may be used is an amount sufficient to cause greater than 10% reduction in number of cancerous cells. In other embodiments, an effective dosing amount is sufficient to reduce the tumor volume by greater than 10% over a given time period compared to the volume before administration of the compound. In other embodiments, the effective amount is measured based upon the treatment with the compound and one or more different pharmaceutical agents or modalities.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.01% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

IV. COMBINATION THERAPY

In addition to being used as a monotherapy, the compounds of the present disclosure may also be used in combination therapies. In some embodiments, effective combination therapy is achieved with a single composition or pharmacological formulation that includes both agents, or with two distinct compositions or formulations, administered at the same time, wherein one composition includes a compound of this invention, and the other includes the second agent(s). Alternatively, in other embodiments, the therapy precedes or follows the other agent treatment by intervals ranging from minutes to months.

A wide range of second therapies may be used in conjunction with the compounds of the present disclosure. Such second therapies include, but are not limited to, surgery, immunotherapy, radiotherapy, or a second chemotherapeutic agent. In some embodiments, the second chemotherapeutic agent is a N-terminus Hsp90 inhibitor such as geldanamycin, radicicol, the geldanamycin derivative 17AAG, NVP-AUY922, or gamitrinib. A variety of different Hsp90 inhibitors which may be used in combination with compounds provided herein are described in Jhaveri, et al., 2012, which is incorporated herein by reference.

V. DEFINITIONS

The definitions below supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

1. Chemical Groups

When used in the context of a chemical group: "hydrogen" means —H; "hydroxy" means —OH; "oxo" means =O; "carbonyl" means —C(=O)—; "carboxy" means —C(=O)OH (also written as —COOH or —CO₂H); "halo" and "halogen" means independently —F, —Cl, —Br or —I; "amino" means —NH₂; "hydroxyamino" means —NHOH; "nitro" means —NO₂; imino means =NH; "cyano" means —CN; "isocyanate" means —N=C=O; "azido" means —N₃; in a monovalent context "phosphate" means —OP(O)(OH)₂ or a deprotonated form thereof; in a divalent context "phosphate" means —OP(O)(OH)O— or a deprotonated form thereof; "mercapto" means —SH; and "thio" means =S; "sulfonyl" means —S(O)₂—; "hydroxysulfonyl" means —S(O)₂OH; "sulfonamide" means —S(O)₂NH₂; and "sulfinyl" means —S(O)—.

In the context of chemical formulas, the symbol "-" means a single bond, "=" means a double bond, and "≡" means triple bond. The symbol "----" represents an optional bond, which if present is either single or double. The symbol "====" represents a single bond or a double bond. Thus, for example, the formula

includes

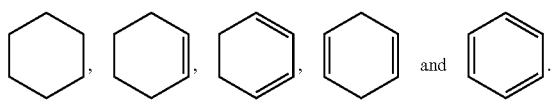

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "〜〜", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◄━" means a single bond where the group attached to the thick end of the wedge is "out of the page." The symbol "⫿⫿⫿" means a single bond where the group attached to the thick end of the wedge is "into the page". The symbol "〜〜" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

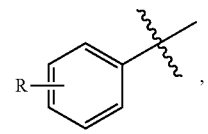

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

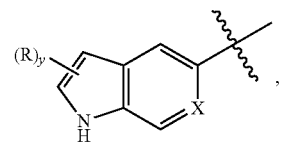

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C \le 8)}$" or the class "alkene$_{(C \le 8)}$" is two. Compare with "alkoxy$_{(C \le 10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group atom means the compound or chemical group contains a planar unsaturated ring of atoms that is stabilized by an interaction of the bonds forming the ring.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$-(methylene), —CH$_2$CH$_2$—, —CH$_2$C(CH$_3$)$_2$CH$_2$—, and —CH$_2$CH$_2$CH$_2$— are non-limiting examples of alkanediyl groups. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "cycloalkenyl" when used without the "substituted" modifier refers to a monovalent unsaturated aliphatic group with a carbon atom as the point of attachment, a linear or branched cyclo or cyclic structure, at least one non-aromatic carbon-carbon double bond, no carbon-carbon triple bonds, and no atoms other than carbon and hydrogen. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples are: pyridinylmethyl and 2-furylmethyl. When the term aralkyl is used with the "substituted" modifier one or more hydrogen atom from the alkanediyl and/or the heteroaryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted heteroaralkyls are: 3-(2-chloropyridinyl)methyl and 2-(3-hydroxyquinonyl)-methyl.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. The term "nitrogen containing heterocycloalkyl" refers to a heterocycloalkyl group as that term is defined herein wherein at least one of the ring atoms is a nitrogen atom. The term nitrogen containing heterocycloalkyl does not preclude other heteroatoms as a ring atom provided at least one of the heteroatoms is a nitrogen atom. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

The term "alkylsulfonyl" when used without the "substituted" modifier refers to the groups —S(O)$_2$R in which R is an alkyl, as that term is defined above. The terms "cycloalkylsulfonyl", "alkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

2. Chemical Group Terms Used in Original PCT Claims 74-86

The definitions in this section are applicable only to original PCT claims 74-86 and continue to apply to only those claims as they may be renumbered or amended during the prosecution of this application.

The term "hydrocarbyl" refers to univalent hydrocarbyl radicals containing 1 to about 30 carbon atoms, or 1 to about 24 carbon atoms, or 1 to about 18 carbon atoms, or about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

The term "cyclic" refers to alicyclic or aromatic substituents that may or may not be substituted and/or heteroatom containing, and that may be monocyclic, bicyclic, or polycyclic.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, heteroatom-containing alkenyl, and heteroatom-containing aryl."

The term "alkyl" or "aliphatic" refer to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, or 1 to about 12 carbon atoms. The term "lower alkyl" intends an alkyl group of 1 to 6 carbon atoms. Substituents identified as "$C_1$-$C_6$ alkyl" or "lower alkyl" contains 1 to 3 carbon atoms, and such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "alkenyl" may be used herein to refer to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, or 2 to 12 carbon atoms. The term "lower alkenyl" intends an alkenyl group of 2 to 6 carbon atoms, and the specific term "cycloalkenyl" intends a cyclic alkenyl group, or having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" may be used herein to refer to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, or 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "aryl" may be used herein, and unless otherwise specified, to refer to an aromatic substituent containing a single aromatic ring or multiple aromatic rings that are fused together, directly linked, or indirectly linked (such that the different aromatic rings are bound to a common group such as a methylene or ethylene moiety). Examples of aryl groups contain 5 to 20 carbon atoms, and aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "alkaryl" refers to an aryl group with an alkyl substituent, and the term "aralkyl" may be used to refer to an alkyl group with an aryl substituent, wherein "aryl" and "alkyl" are as defined above. Examples of aralkyl groups contain 6 to 24 carbon atoms, and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzyl-cyclohexylmethyl, and the like. Alkaryl groups include, for example, p-methylphenyl, 2,4-dimethylphenyl, p-cyclohex-ylphenyl, 2,7-dimethyinaphthyl, 7-cyclooctylnaphthyl, 3-ethyl-cyclopenta-1,4-diene, and the like.

The term "alkoxy" may be used herein to refer to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein contain 1 to 3 carbon atoms, and such substituents contain 1 or 2 carbon atoms (i.e., methoxy and ethoxy). Analogously, the term "aryloxy" as used herein refers to an aryl group bound through a single, terminal ether linkage, wherein "aryl" is as defined above. An "aryloxy" group may be represented as —O-aryl where aryl is as defined above. Examples of aryloxy groups contain 5 to 20 carbon atoms, and aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

3. Other Definitions

The use of the word "a" or "an," when used in conjunction with the term "comprising" in the claims and/or the specification may mean "one," but it is also consistent with the meaning of "one or more," "at least one," and "one or more than one." Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiary-butylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon atoms), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Other abbreviations used herein are as follows: DMSO, dimethyl sulfoxide.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Methods and Materials a) MTS/PMS Cell Viability Assay (SKBr3 and MCF-7 Cells)

Cells were maintained in a 1:1 mixture of Advanced DMEM/F12 (Gibco) supplemented with non-essential amino acids, L-glutamine (2 mM), streptomycin (500 μg/mL), penicillin (100 units/mL), and 10% FBS. Cells were grown to confluence in a humidified atmosphere (37° C., 5% $CO_2$), seeded (2000/well, 100 μL) in 96-well plates, and allowed to attach overnight. Compound at varying concentrations in DMSO (1% DMSO final concentration) was added, and cells were returned to the incubator for 72 hr. At 72 hr, the number of viable cells was determined using an MTS/PMS cell proliferation kit (Promega) per the manufacturer's instructions. Cells incubated in 1% DMSO were used at 100% proliferation, and values were adjusted accordingly. $IC_{50}$ values were calculated from separate experiments performed in triplicate using GraphPad Prism.

b) Promega CellTiter-Glo (CTG) Luminescent Assay

Antiproliferative activities against MDA-MB-468LN, MDA1986 and JMAR cell lines were performed with 384-well white plates with the Promega CellTiter-Glo (CTG) luminescent assay with 72 hr compound treatment. Data analysis was performed using GraphPad Prism. Selected data were further checked with MTS/PMS cell viability assay with 96-well plates, which correlated well with Promega CellTiter-Glo luminescent assay.

c) Sulforhodamine B Assay

The sulforhodamine B assay is used to measure drug-induced cytotoxicity and cell proliferation for large-scale drug-screening applications. Its principle is based on the ability of the protein dye sulforhodamine B to bind electrostatically on pH dependent protein basic amino acid residues of trichloroacetic acid-fixed cells. The aim is to evaluate samples showing selective growth inhibition or cell killing of particular tumor cell lines.

The SRB assay is performed by treating cells using a 10 point dose-response curve. The cells are fixed with trichloroacetic acid solution and stained with sulforhodamine B dye. The stained cells are then solubilized with 10 mM Tris buffer and read for absorbance at 565 nm.

Percentage growth is calculated at each of the drug concentration levels using the absorbance raw data.

Percentage growth inhibition is calculated as:

$$[(T_i-T_z)/(C-T_z)] \times 100 \text{ for concentrations for which } T_i \geq T_z.$$

$$[(T_i-T_z)/(T_z)] \times 100 \text{ for concentrations for which } T_i < T_z.$$

$T_i$=Absorbance of wells at a given drug concentration level.
$T_z$=Absorbance time zero wells
C=Absorbance of untreated wells (media and cells only)

After growth inhibition values have been calculated, the data is plotted on Graphpad Prism software. Data is entered and plotted on a sigmoidal dose-response curve using non-linear regression.

d) Western Blot Analyses

MCF-7 cells were cultured as described above and treated with various concentrations of drug, Geldanamycin (GDA or G) in DMSO (1% DMSO final concentration), or vehicle (DMSO) for 24 hr. Cells were harvested in cold PBS and lysed in RIPA lysis buffer containing 1 mM PMSF, 2 mM sodium orthovanadate, and protease inhibitors on ice for 1 hr. Lysates were clarified at 14000 g for 10 min at 4° C. Protein concentrations were determined using the Pierce BCA protein assay kit per the manufacturer's instructions. Equal amounts of protein (15 μg) were electrophoresed under reducing conditions, transferred to a PVDF membrane, and immunoblotted with the corresponding specific antibodies. Membranes were incubated with an appropriate horseradish peroxidase-labeled secondary antibody, developed with a chemiluminescent substrate, and visualized.

e) Proteolytic Fingerprinting Assay

Rabbit reticulocyte (Green Hectares) incubated under conditions of protein synthesis at 30° C. in the presence of compound or vehicle (1% DMSO) for 10 minutes. Each reaction mixture contained 66.6% rabbit reticulocyte and 33.3% ATP regenerating system (10 mM creatine phosphate and 20 μg mL$^{-1}$ creatine phosphokinase) and a final concentration of 75 mM KCl. Each reaction mixture contained the indicated amount of compound. After incubating, the samples were immediately placed on ice and the indicated amount of TPCK-treated trypsin (Worthington) was added to each sample. The samples digested on ice for an additional 6 minutes and the reactions were quenched by the addition of Laemmli sample buffer followed by immediate boiling. Equal amounts of each sample were electrophoresed under reducing conditions (12% acrylamide gels), transferred to PVDF, and immunoblotted with an antibody specific to the Hsp90 C-terminus. Membranes were incubated with an appropriate horseradish peroxidase-labeled secondary antibody, developed with a chemiluminescent substrate, and visualized.

Example 1: Compound Activity in Cancer Cell Lines

The cellular activity manifested by 4a and 4b was evaluated against a panel of cancer lines, including SKBr3 (estrogen receptor negative, Her2 over-expressing) lymphatic metastatic MDA-MB-468LN (estrogen receptor negative, Ah receptor-positive) and MCF-7 (estrogen receptor positive) breast cancer cell lines, head and neck squamous cell carcinoma (HNSCC) MDA1986 and JMAR cell lines, as well as prostate cancer cell lines PC3-MM2 and LNCaP. Both compounds manifested activity at low micromolar concentrations against all cell lines tested. Encouraged by these studies, substitutions on the phenyl and benzyl side chains were explored to determine structure-activity relationships for this series of compounds. The inhibitory activity of the compounds is shown in Table 1. Both 4-chloro (4c) and 3-chloro (4f) substitutions showed improved inhibitory activity against SKBr3 cell lines. Electron-donating groups such as 4-methyl (4i) and 4-methoxy (4j) as well as 4-chloro analogues (4g) manifested similar potencies compared to the unsubstituted analogue, 4b. However, the 4-NO$_2$ substituent (4l) exhibited improved activity against all cancer cell lines tested, manifesting an IC$_{50}$ of 0.38 and 0.64 μM against SKBr3 and MCF-7 cell lines, respectively. In general, sterically bulky groups such as 4-tert-butyl (4k) were found favorable. When a hydrophobic cyclohexylmethyl group was installed as the appendage (4q), improved inhibitory activities against SKBr3, MDA1986 and JMAR cells were observed, indicating the existence of a hydrophobic region in this area of the binding pocket. The observed inhibitory activities manifested by these triazole-containing analogues indicate that hydrogen bonding interactions on the side chain are favorable for Hsp90 C-terminal inhibition, which might result from either direct hydrogen bonding interactions or conformational rigidity on the side chain which might direct hydrophobic substituent into the hydrophobic pocket. The compounds in Table 1 are represented by the formula:

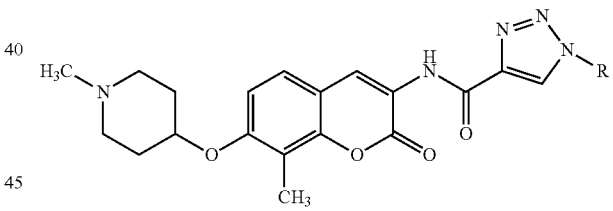

wherein: R is as defined in the table.

TABLE 1

Antiproliferative Activity of Coumarin-based Triazole Derivatives[a]

| R (IC$_{50}$, μM) | SKBr3[b] | MCF-7[b] | MDA-MB-468LN[c] | MDA1986[c] | JMAR[c] | PC3-MM2[d] | LNCaP[d] |
|---|---|---|---|---|---|---|---|
| Ph (4a) | 0.94 ± 0.02[a] | 1.33 ± 0.13[a] | 1.10 ± 0.21 | 1.50 ± 3.40 | 2.30 ± 0.40 | 2.69 | 4.72 ± 0.71 |
| Bn (4b) | 0.99 ± 0.08 | 1.08 ± 0.00 | 2.40 | 1.60 ± 0.21 | 2.10 ± 0.12 | 9.8 ± 13.5 | 15.5 ± 8.75 |
| 4-ClC$_6$H$_5$ (4c) | 0.58 ± 0.03 | 2.04 ± 0.25 | 0.81 ± 0.15 | 0.18 ± 0.11 | 0.43 ± 0.38 | 2.79 ± 0.49 | 2.45 ± 0.47 |
| 4-BrC$_6$H$_5$ (4d) | 1.38 ± 0.05 | 5.07 ± 1.86 | 2.80 ± 0.50 | 2.90 ± 0.33 | 3.60 ± 0.63 | 3.81 ± 4.99 | 15.2 ± 9.19 |
| 4-MeC$_6$H$_5$ (4e) | 1.08 ± 0.05 | 1.38 ± 0.07 | 4.00 ± 1.92 | 0.29 | 3.64 | >100 | >100 |
| 3-ClC$_6$H$_5$ (4f) | 0.71 ± 0.14 | 1.14 ± 0.18 | 4.60 | 6.40 | 6.40 | 3.90 ± 5.11 | 13.3 ± 11.9 |
| 4-ClBn (4g) | 1.14 ± 0.19 | 1.44 ± 0.31 | 2.20 ± 0.30 | 1.70 ± 0.52 | 1.70 ± 0.20 | 3.67 ± 1.38 | 4.65 ± 0.71 |
| 4-BrBn (4h) | 0.73 ± 0.01 | 1.36 ± 0.08 | 2.10 ± 0.60 | 2.00 ± 0.50 | 1.60 ± 0.31 | 3.80 ± 1.42 | 4.96 ± 0.67 |
| 4-MeBn (4i) | 1.21 ± 0.07 | 1.50 ± 0.19 | 2.40 ± 0.25 | 1.50 ± 0.20 | 1.80 ± 0.95 | 7.32 ± 5.44 | 7.24 ± 1.02 |
| 4-MeOBn (4j) | 1.31 ± 0.20 | 1.42 ± 0.14 | 3.40 ± 1.27 | 2.60 ± 0.30 | 6.70 | 7.85 ± 0.42 | >100 |
| 4-t-BuBn (4k) | 0.45 ± 0.03 | 1.22 ± 0.07 | 0.74 ± 0.22 | 0.34 ± 0.09 | 0.58 ± 0.14 | 2.37 ± 0.00 | 1.84 ± 0.00 |
| 4-NO$_2$Bn (4l) | 0.38 ± 0.13 | 0.64 ± 0.01 | 0.81 ± 0.23 | 0.18 ± 0.22 | 0.26 ± 0.34 | 2.49 ± 0.32 | 1.28 ± 0.71 |
| 4-FBn (4m) | 1.08 ± 0.01 | 1.34 ± 0.19 | 2.60 ± 6.12 | 1.77 ± 4.10 | 2.38 ± 5.38 | 8.82 ± 1.14 | 3.31 ± 0.00 |

TABLE 1-continued

Antiproliferative Activity of Coumarin-based Triazole Derivatives[a]

| R (IC$_{50}$, μM) | SKBr3[b] | MCF-7[b] | MDA-MB-468LN[c] | MDA1986[c] | JMAR[c] | PC3-MM2[d] | LNCaP[d] |
|---|---|---|---|---|---|---|---|
| 3-ClBn (4n) | 1.06 ± 0.01 | 1.68 ± 0.01 | 1.14 ± 1.17 | 0.23 ± 0.22 | 0.19 ± 0.10 | 6.00 ± 1.13 | 3.03 ± 0.05 |
| 3-MeOBn (4o) | 1.15 ± 0.19 | 1.61 ± 0.06 | 2.69 ± 1.33 | 1.34 ± 0.31 | 1.49 ± 0.31 | 7.20 ± 0.15 | 3.49 ± 0.30 |
| 2-ClBn (4p) | 1.30 ± 0.07 | 0.99 ± 0.08 | 2.10 ± 0.52 | 3.20 ± 1.37 | 3.70 ± 0.85 | 6.66 ± 5.44 | >100 |
| CH$_2$C$_6$H$_{13}$ (4q) | 0.61 ± 0.00 | 1.29 ± 0.16 | 0.99 ± 0.24 | 0.24 ± 0.32 | 0.30 ± 0.26 | 3.13 ± 0.14 | 1.20 ± 0.06 |
| Ph(CH$_2$)$_2$ (4r) | 0.13 ± 0.01 | 0.55 ± 0.01 | 0.99 ± 0.10 | 0.11 ± 0.30 | 0.74 ± 0.86 | 1.40 ± 0.04 | 2.36 ± 0.53 |
| Ph(CH$_2$)$_3$ (4s) | 1.73 ± 0.05 | 1.65 ± 0.03 | NT | NT | NT | NT | NT |

[a]Values represent mean ± standard deviation for at least two separate experiments performed in triplicate.
[b]Cellular activities were determined with MTS/PMS cell viability assay.
[c]Cellular activities were determined with Promega CellTiter-Glo (CTG) luminescent assay.
[d]Cellular activities were determined with Sulforhodamine B Assay.

Increasing flexibility between the triazole side chain and the terminal phenyl ring was sought to determine whether improved inhibitory activity could be achieved. Therefore, compounds bearing two (4r) or three carbons (4s) were synthesized by an amide coupling reaction between the corresponding triazolylic acids (7r and 7s) and amine 6 as described in Example 2. The antiproliferative activities manifested by these compounds were then determined. A comparison of the data shown for 4a-b and 4r-s (Table 1) illustrates that compound 4r, which contains a two carbon linker, exhibited the most improved activity amongst the four analogues evaluated, exhibiting IC$_{50}$s of 130 nM against SKBr3 cell line and about 110 nM against MDA1986 cell line.

To confirm that the observed antiproliferative activities were resulting from Hsp90 inhibition, western blot analyses of Hsp90 client proteins in MCF-7 cell lysates were performed. Actin, whose maturation does not require the Hsp90 machinery, was used as a control. As shown in FIG. 1, Hsp90 client proteins Her2, Akt and Raf-1 were degraded upon exposure of 4f, 4o or 4q at concentrations that mirror their anti-proliferative values, confirming that cell viability is directly linked to Hsp90 inhibition.

The antiproliferation activities manifested by the biphenyl amide compounds are reported in Table 2. In contrast to the coumarin-based analogues 4a and 4b, which showed similar anti-proliferative activity, the phenyl and benzyl analogues 5a and 5b displayed very different activities, with the latter being about 2.5-8 times more potent against all the cell lines evaluated, manifesting IC$_{50}$s of 170 and 500 nM against SKBr3 and MCF-7 cell lines, respectively. A compound that contains the two carbon linker (5c) was found to exhibit activity similar to those of the benzyl analogue, 5b. Subsequent studies were then aimed to modify the benzylic ring. As can be seen in Table 2, halogens at the 4-position were in general detrimental to inhibitory activity (5d-e); while electron-donating groups such as 4-methyl (5f) and 4-methoxy (5g) retained potencies against SKBr3 and MDA-MB-468LN cells, but manifested increased inhibitory activities against the MCF-7 cell line (120 and 270 nM, respectively) and the prostate cancer cell lines. 3-Chloro (5k), 3-methoxy (5l), and 2-chloro (5m) produced decreased activity against SKBr3 cells, but increased activities against MCF-7 and MDA-MB-468LN cells. Combination of 2-chloro and 4-methyl substitution (5n) retained activity against SKBr3 cells, but did not improve activity against MCF-7 cells compared to the 4-methyl substituted analogue, 5f. However, this combination indeed improved activities against MDA-MB-468LN, MDA1986 and LNCaP cell lines. The 4-tert-butyl substituted analogue, 5h, manifested decreased antiproliferative activity against all cell lines tested compared to the 4-methyl analogue, 5f, which is in contrast to the coumarin derivatives 4i and 4k, indicating a smaller hydrophobic pocket exists when the biaryl scaffold is present. Similar to the coumarin scaffold, replacement of the benzyl group with a cyclohexylmethyl substituent resulted in compounds that manifested good inhibitory activities. Differences in the structure-activity relationships for the two scaffolds suggest the biphenyl ring system presents the side chain through different binding interactions. The compounds in Table 2 are represented by the formula:

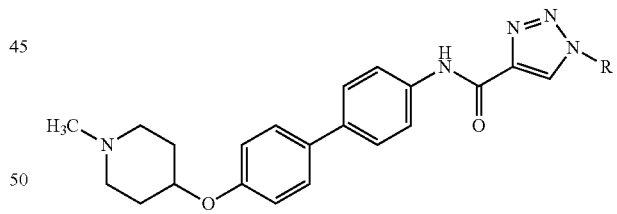

wherein: R is as defined in the table.

TABLE 2

Antiproliferative Activity of Biphenyl Triazole Analogues 5[a]

| R (5, IC$_{50}$, μM) | SKBr3[b] | MCF-7[b] | MDA-MB-468LN[c] | MDA1986[c] | JMAR[c] | PC3-MM2[d] | LNCaP[d] |
|---|---|---|---|---|---|---|---|
| Ph (5a) | 1.14 ± 0.10[a] | 1.44 ± 0.18[a] | 0.83 ± 0.16 | 1.30 ± 0.09 | 2.20 ± 0.24 | 4.26 ± 5.59 | 3.89 ± 1.09 |
| Bn (5b) | 0.17 ± 0.02 | 0.50 ± 0.02 | 0.34 ± 0.07 | 0.28 ± 0.10 | 0.50 ± 0.06 | 0.55 ± 0.46 | 0.65 ± 0.54 |
| CH$_2$Bn (5c) | 0.19 ± 0.02 | 0.38 ± 0.10 | 0.36 ± 0.04 | 0.10 ± 0.23 | 0.58 ± 0.46 | 0.83 ± 0.34 | 0.43 ± 0.22 |
| 4-ClBn (5d) | 0.32 ± 0.10 | 0.44 ± 0.04 | 0.74 ± 0.19 | 1.30 ± 0.37 | 2.30 ± 0.82 | 0.66 ± 0.21 | 1.59 ± 0.78 |
| 4-BrBn (5e) | 0.49 ± 0.03 | 0.56 ± 0.04 | 2.80 ± 0.61 | 3.10 ± 0.87 | 7.80 | 19.9 ± 27.9 | 0.54 ± 0.12 |
| 4-MeBn (5f) | 0.17 ± 0.03 | 0.12 ± 0.01 | 0.41 ± 0.26 | 0.36 ± 0.05 | 0.42 ± 0.07 | 0.36 ± 0.04 | 0.20 ± 0.04 |

TABLE 2-continued

Antiproliferative Activity of Biphenyl Triazole Analogues 5[a]

| R (5, IC$_{50}$, μM) | SKBr3[b] | MCF-7[b] | MDA-MB-468LN[c] | MDA1986[c] | JMAR[c] | PC3-MM2[d] | LNCaP[d] |
|---|---|---|---|---|---|---|---|
| 4-MeOBn (5g) | 0.16 ± 0.02 | 0.27 ± 0.06 | 0.17 | 0.48 ± 0.09 | 0.61 ± 0.09 | 0.44 ± 0.19 | 0.24 ± 0.07 |
| 4-t-BuBn (5h) | 3.72 ± 0.68 | 10.48 ± 0.40 | 2.61 ± 0.76 | 2.34 ± 1.81 | 3.49 ± 2.05 | >100 | 1.01 ± 1.39 |
| 4-NO$_2$ (5i) | 0.45 ± 0.04 | 0.55 ± 0.01 | 0.56 ± 0.25 | 0.19 ± 0.17 | 0.21 ± 0.35 | 1.03 ± 0.16 | 0.60 ± 0.34 |
| 4-FBn (5j) | 0.72 ± 0.18 | 1.04 ± 0.08 | 1.09 ± 0.23 | 0.93 ± 0.34 | 1.39 ± 0.52 | 2.81 ± 1.82 | 1.64 ± 0.97 |
| 3-ClBn (5k) | 0.39 ± 0.01 | 0.34 ± 0.02 | 0.17 ± 0.02 | 0.17 ± 0.12 | 0.27 ± 0.04 | 0.35 ± 0.14 | 0.12 ± 0.10 |
| 3-MeOBn (5l) | 0.32 ± 0.02 | 0.16 ± 0.02 | 0.19 ± 0.05 | 0.28 ± 0.09 | 0.21 ± 0.12 | 0.55 ± 0.37 | 0.16 |
| 2-ClBn (5m) | 0.34 ± 0.04 | 0.38 ± 0.03 | 0.22 ± 0.03 | 0.81 ± 0.05 | 0.65 | 1.04 ± 0.51 | 0.61 ± 0.34 |
| 2-Cl,4-MeBn (5n) | 0.16 ± 0.01 | 0.20 ± 0.05 | 0.15 ± 0.02 | 0.15 ± 0.06 | 0.43 ± 0.25 | 0.35 ± 0.12 | 0.05 ± 0.04 |
| CH$_2$C$_6$H$_{13}$ (5o) | 0.20 ± 0.02 | 0.31 ± 0.04 | 0.24 ± 0.06 | 0.38 ± 0.14 | 0.26 ± 0.45 | 5.12 ± 6.54 | 0.48 ± 0.68 |

[a]Values represent mean ± standard deviation for at least two separate experiments performed in triplicate.
[b]Cellular activities were determined with MTS/PMS cell viability assay.
[c]Cellular activities were determined with Promega CellTiter-Glo (CTG) luminescent assay.
[d]Cellular activities were determined with Sulforhodamine B Assay.

Figure 2:
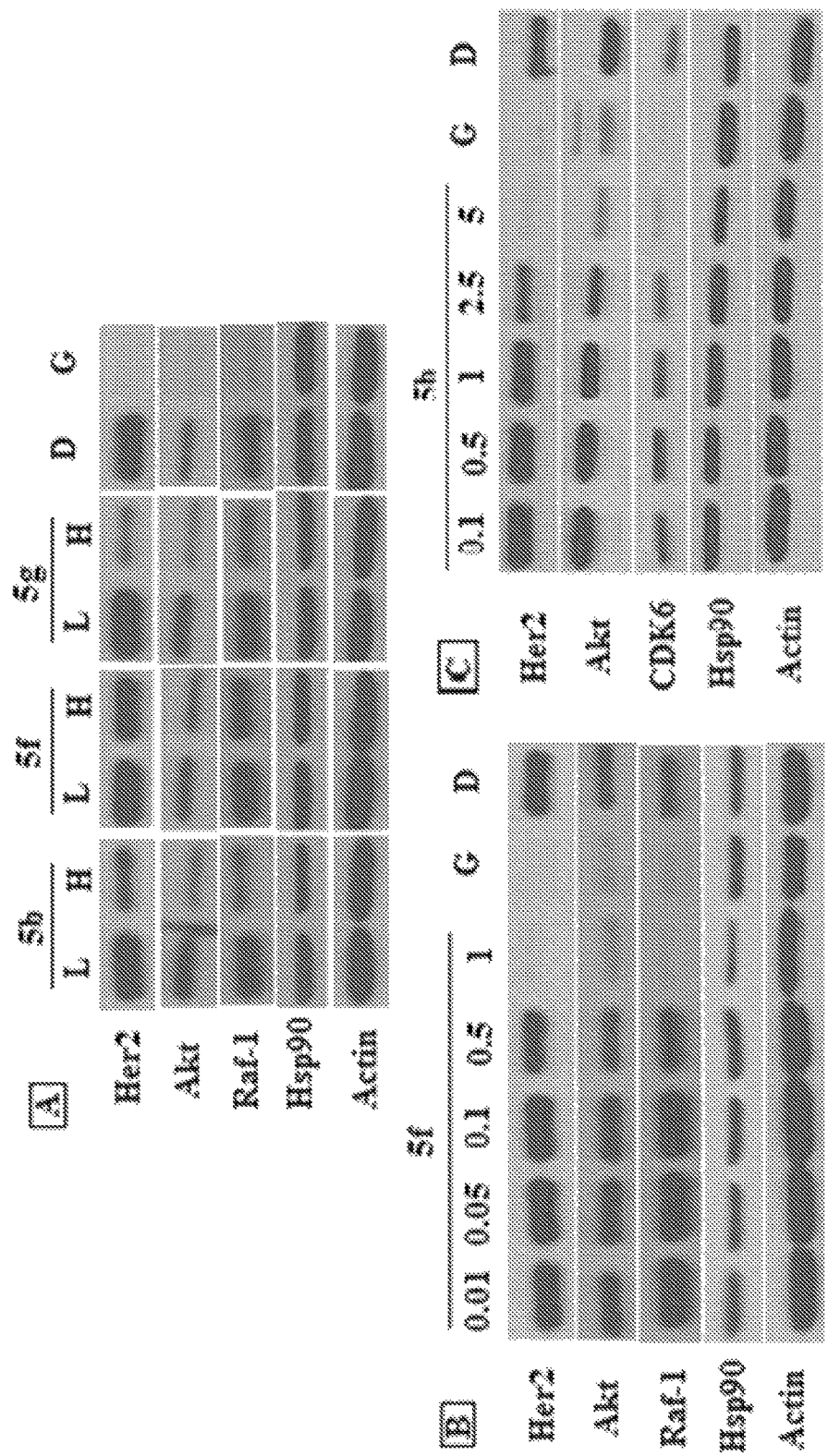
FIGS. 2A-2C show the Western blot analyses of the Hsp90 client protein degradation in MCF-7 breast cancer cells lysis 24 h after treatment of biphenyl triazole analogues 5b, 5f and 5g.

The cellular activity manifested by these biphenyl analogues was shown to result from Hsp90 inhibition by performing western blot analyses of MCF-7 cell lysates treated with such compounds (FIG. 2). Hsp90-dependent client proteins were decreased upon exposure to 5b, 5f and 5g at concentrations that mirror their antiproliferative IC$_{50}$s. Clear degradation of Hsp90 client proteins Her2, Akt and Raf-1 was observed, while actin, which does not rely upon the Hsp90 chaperone machinery, remained constant, indicating that the antiproliferative activities manifested by these compounds resulted from Hsp90 inhibition (FIG. 2A). These client proteins Her2, Akt, Raf-1 and CDK6 were also degraded in a concentration-dependent manner upon exposure to the most potent analogue 5f and the representative analogue 5b, against MCF-7 cells (FIGS. 2B & 2C), while actin levels remain unchanged. Examination of Hsp90 expression when exposed to these compounds have shown that while GDA, the positive control, induced Hsp90 upregulation due to induced heat shock response, Hsp90 levels were constant or even decreased upon treatment of these compounds (FIGS. 2A-2C), consistent with the observations manifested by many Hsp90 C-terminal inhibitors, (Burlison, et al., 2006; Zhao, et al., 2010; Zhao and Blagg, 2013; Zhao, et al., 2014; Kusuma, et al., 2014) indicating that these compounds exhibited Hsp90 inhibitory activity through C-terminal inhibition. At a concentration as low as 1 μM, 5f was able to deplete Hsp90 client proteins as well as Geldanamycin at 500 nM, demonstrating the remarkable activity exhibited by this compound for Hsp90 inhibition.

Figures 3A, 3B:
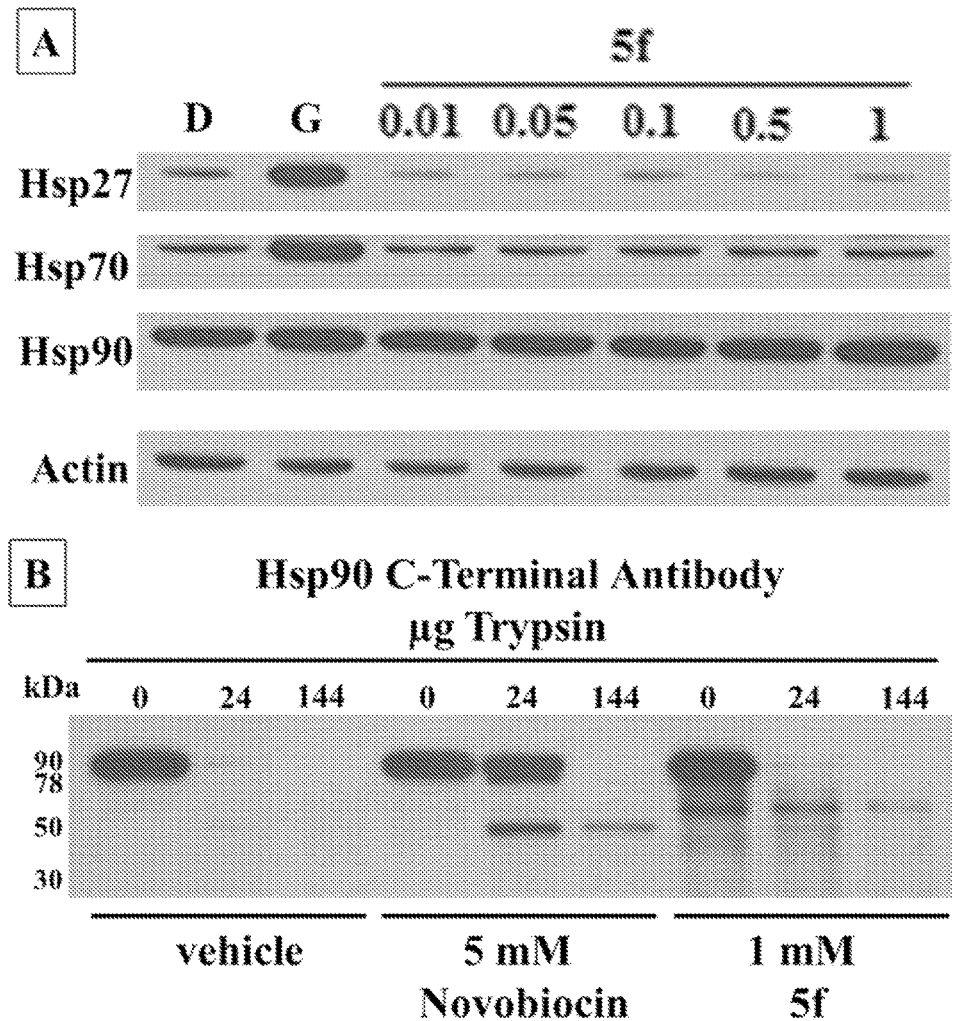
FIGS. 3A & 3B shows Western blot analyses (FIG. 3A) of the heat shock proteins Hsp27, Hsp70 and Hsp90 in MCF-7 breast cancer cells lysis 24 h after treatment with 5f. Concentrations (in μM) of 5f are indicated above each lane. Geldanamycin (G, 500 nM) and DMSO (D) are positive and negative controls. No increase in heat shock proteins Hsp27, Hsp70, or Hsp90 was observed with increasing concentrations of 5f.

Furthermore, no increase in heat shock proteins Hsp27, Hsp70, or Hsp90 was observed with increasing concentrations of 5f (FIG. 3A). Depletion of client proteins without increased levels of heat shock proteins is a hallmark of Hsp90 C-terminal inhibition. To determine whether 5f binds the Hsp90 C-terminus, proteolytic fingerprinting of Hsp90 from TnT rabbit reticulocyte in the presence of 5f was performed. Novobiocin locks Hsp90 in the "open conformation" when bound to the C-terminus (Matts, et al., 2011; Yun, et al., 2004). In this conformation, amino acids Lys615 and Arg620 are not solvent exposed and are "protected" from cleavage by trypsin. This results in bands that differ in molecular weight from vehicle control. The C-terminal Hsp90 antibody AC88 detects the emergence of a 50 kDa band in the presence of novobiocin and other C-terminal inhibitors. A 50 kDa band was detected with 5 mM novobiocin and 1 mM 5f that is not detected for the vehicle control (FIG. 3B). Together, these data further support that 5f was bound to and inhibited the Hsp90 C-terminus, which leads to client protein degradation without induction of the heat shock response.

Example 2: Compounds and Synthesis

A. General Procedure for the Synthesis of Triazolyl Acids

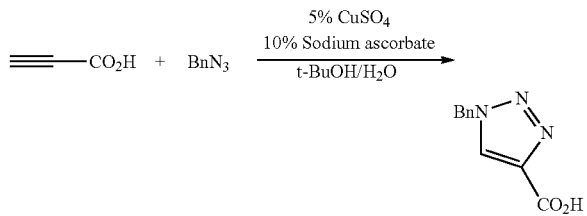

1-benzyl-1H-1,2,3-triazole-4-carboxylic acid (7b)

The triazolyl acids 7 were synthesized using methods based upon a literature procedure (Kolarovic, et al., 2011). To a 100 mL sealed tube was added CuSO$_4$ (16 mg, 0.1 mmol), sodium ascorbate (40 mg, 0.2 mmol) and H$_2$O (2 mL). The mixture was then treated with azide (266 mg, 2.0 mmol) and t-BuOH (2 mL) and then propiolic acid (168 mg, 2.4 mmol), the tube was sealed and the mixture was stirred overnight. The mixture was then added saturated NaHCO$_3$ solution, extracted with ether (10 mL×2). The organic layer was then discarded, and the aqueous layer was acidified with 1N H$_2$SO$_4$, and extracted with EtOAc (15 mL×3) and dried over Na$_2$SO$_4$. The solvent was evaporated to afford the title triazole acid (334 mg, 82% yield) as a white solid which is usually pure enough to be used in the next step. $^1$H NMR (400 MHz, CDCl$_3$) δ 8.04 (s, 1H), 7.44-7.40 (m, 3H), 7.34-7.28 (m, 2H), 5.60 (s, 2H). The $^1$H NMR is consistent with the literature.[1]

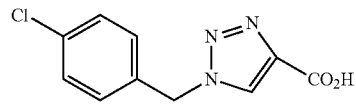 [SMILES: O=C(O)c1cn(Cc2ccc(Cl)cc2)nn1]

1-(4-Chlorobenzyl)-1H-1,2,3-triazole-4-carboxylic acid (7g)

The reaction of 4-chlorobenzyl azide (1.64 g, 6.9 mmol), $CuSO_4$ (56 mg, 0.35 mmol), sodium ascorbate (140 mg, 0.7 mmol), and propiolic acid (590 mg, 8.4 mmol) in t-BuOH (8 mL) and $H_2O$ (8 mL) afforded the title triazole acid (987 mg, 60% yield) as a white solid. $^1$H NMR (400 MHz, DMSO-$d_6$) δ 13.14 (s, 1H), 8.79 (s, 1H), 7.49-743 (m, 2H), 7.40-7.35 (m, 2H), 5.66 (s, 2H); $^{13}$C NMR (125 MHz, DMSO-$d_6$) δ 161.6, 139.9, 134.6, 133.0, 130.0, 129.1, 128.8, 52.2; HRMS (TOF-ESI) calcd for $C_{10}H_8ClN_3O_2Na[M+Na]^+$: 260.0203, found: 260.0200.

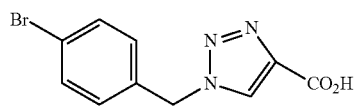

1-(4-Bromobenzyl)-1H-1,2,3-triazole-4-carboxylic acid (7h)

The reaction of 4-bromobenzyl azide (1.06 g, 5 mmol), $CuSO_4$ (40 mg, 0.25 mmol), sodium ascorbate (100 mg, 0.5 mmol), and propiolic acid (420 mg, 6 mmol) in t-BuOH (6 mL) and $H_2O$ (6 mL) afforded the title triazole acid (575 mg, 40% yield) as a white solid. $^1$H NMR (400 MHz, DMSO-$d_6$) δ 8.74 (s, 1H), 7.61-7.57 (m, 2H), 7.33-7.28 (m, 2H), 5.63 (s, 2H); $^{13}$C NMR (125 MHz, DMSO-$d_6$) δ 161.7, 140.3, 135.0, 131.7, 130.3, 128.9, 121.6, 52.2; HRMS (TOF-ESI) calcd for $C_{10}H_8BrN_3O_2Na[M+Na]^+$: 303.9698, found: 303.9705.

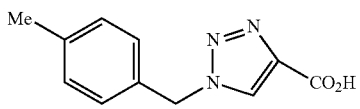 [SMILES: Cc1ccc(Cn2cc(C(=O)O)nn2)cc1]

1-(4-Methylbenzyl)-1H-1,2,3-triazole-4-carboxylic acid (7i)

The reaction of 4-methylbenzyl azide (636 mg, 4.32 mmol), $CuSO_4$ (35 mg, 0.22 mmol), sodium ascorbate (86 mg, 0.43 mmol), and propiolic acid (364 mg, 5.2 mmol) in t-BuOH (6 mL) and $H_2O$ (6 mL) afforded the title triazole acid (712 mg, 76% yield) as a white solid. $^1$H NMR (400 MHz, DMSO-$d_6$) δ 8.74 (s, 1H), 7.25 (d, J=8.0 Hz, 2H), 7.19 (d, J=8.0 Hz, 2H), 5.59 (s, 2H); $^{13}$C NMR (125 MHz, DMSO-$d_6$) δ 161.6, 139.8, 137.6, 132.6, 129.3, 128.9, 128.0, 52.8, 20.7; HRMS (TOF-ESI) calcd for $C_{11}H_{11}N_3O_2Na[M+Na]^+$: 240.0749; found: 240.0742.

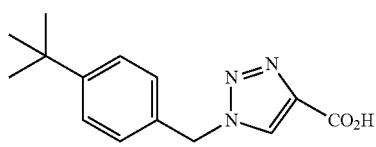 [SMILES: CC(C)(C)c1ccc(Cn2cc(C(=O)O)nn2)cc1]

1-(4-t-Butylbenzyl)-1H-1,2,3-triazole-4-carboxylic acid (7k)

The reaction of 4-t-butylbenzyl azide (886 mg, 4.68 mmol), $CuSO_4$ (37 mg, 0.23 mmol), sodium ascorbate (93 mg, 0.47 mmol), and propiolic acid (328 mg, 4.68 mmol) in t-BuOH (8 mL) and $H_2O$ (8 mL) afforded the title triazole acid (750 mg, 62% yield) as a white solid. $^1$H NMR (400 MHz, DMSO-$d_6$) δ 8.77 (s, 1H), 7.43-7.36 (m, 2H), 7.31-7.25 (m, 2H), 5.60 (s, 2H), 1.26 (s, 9H); $^{13}$C NMR (125 MHz, DMSO-$d_6$) δ 161.6, 150.8, 139.8, 132.7, 128.9, 127.8, 125.6, 52.7, 34.3, 31.0; HRMS (TOF-ESI) calcd for $C_{14}H_{17}N_3O_2Na[M+Na]^+$; 282.1218; found: 282.1215.

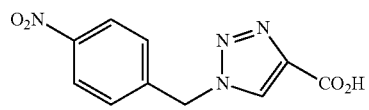 [SMILES: O=C(O)c1cn(Cc2ccc([N+](=O)[O-])cc2)nn1]

1-(4-Nitrobenzyl)-1H-1, 2, 3-triazole-4-carboxylic acid (7l)

The reaction of 4-nitrobenzyl azide (777 mg, 4.36 mmol), $CuSO_4$ (35 mg, 0.22 mmol), sodium ascorbate (86 mg, 0.436 mmol), and propiolic acid (305 mg, 4.36 mmol) in t-BuOH (10 mL) and $H_2O$ (10 mL) afforded the title triazole acid (940 mg, 87% yield) as a yellow solid. $^1$H NMR (400 MHz, DMSO-$d_6$) δ 13.18 (s, 1H), 8.86 (s, 1H), 8.25 (d, J=8.8 Hz, 2H), 7.57 (d, J=8.8 Hz, 2H), 5.84 (s, 2H); $^{13}$C NMR (125 MHz, DMSO-$d_6$) δ 161.5, 147.3, 142.9, 140.0, 129.5, 129.1, 124.0, 52.1; HRMS (TOF-ESI) calcd for $C_{10}H_8N_4O_4Na[M+Na]^+$: 271.0443, found: 277.0436.

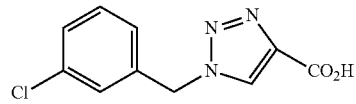 [SMILES: O=C(O)c1cn(Cc2cccc(Cl)c2)nn1]

1-(3-Chlorobenzyl)-1H-1,2,3-triazole-4-carboxylic acid (7n)

The reaction of 3-chlorobenzyl azide (309 mg, 1.84 mmol), propiolic acid (126 mg, 1.8 mmol), $CuSO_4$ (15 mg, 0.092 mmol), sodium ascorbate (37 mg, 0.184 mmol) in t-BuOH (10 mL) and $H_2O$ (10 mL) afforded the title compound (280 mg, 66% yield) as an off-white solid. $^1$H NMR (400 MHz, DMSO-$d_6$) δ 13.14 (bs, 1H), 8.83 (s, 1H), 7.49-7.45 (m, 1H), 7.44-7.40 (m, 2H), 7.34-7.27 (m, 1H), 5.67 (s, 2H); $^{13}$C NMR (125 MHz, DMSO-$d_6$) δ 161.6, 139.9, 137.9, 133.3, 130.7, 129.2, 128.3, 128.0, 126.8, 52.2; HRMS (TOF-ESI) calcd for $C_{10}H_8ClN_3O_2Na[M+Na]^+$: 260.0203, found: 260.0210.

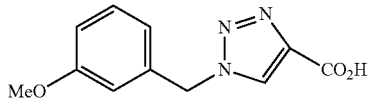 [SMILES: COc1cccc(Cn2cc(C(=O)O)nn2)c1]

1-(3-Methoxybenzyl)-1H-1,2,3-triazole-4-carboxylic acid (7o)

The reaction of 3-methoxybenzyl azide (734 mg, 4.5 mmol), CuSO$_4$ (36 mg, 0.225 mmol), sodium ascorbate (89 mg, 0.45 mmol), and propiolic acid (280 mg, 4.0 mmol) in t-BuOH (10 mL) and H$_2$O (10 mL) afforded the title triazole acid (690 mg, 74% yield) as a white solid. $^1$H NMR (400 MHz, DMSO-d$_6$) δ 13.12 (s, 1H), 8.78 (s, 1H), 7.30 (t, J=8.0 Hz, 1H), 6.96-6.87 (s, 3H), 5.61 (s, 2H), 3.75 (s, 3H); $^{13}$C NMR (125 MHz, DMSO-d$_6$) δ 161.6, 159.4, 139.8, 137.0, 130.0, 129.0, 120.1, 113.8, 113.7, 55.1, 52.9; HRMS (TOF-ESI) calcd for C$_{11}$H$_{11}$N$_3$O$_3$Na[M+Na]$^+$: 256.0698, found: 256.0694.

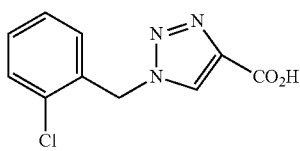 [SMILES: O=C(O)c1cn(Cc2ccccc2Cl)nn1]

1-(2-Chlorobenzyl)-1H-1,2,3-triazole-4-carboxylic acid (7p)

The reaction of 2-chlorobenzyl azide (816 mg, 4.87 mmol), CuSO$_4$ (40 mg, 0.25 mmol), sodium ascorbate (99 mg, 0.5 mmol), and propiolic acid (420 mg, 6.0 mmol) in t-BuOH (8 mL) and H$_2$O (8 mL) afforded the title triazole acid (817 mg, 71% yield) as a white solid. $^1$H NMR (400 MHz, DMSO-d$_6$) δ 13.15 (bs, 1H), 8.74 (s, 1H), 7.56-7.51 (m, 1H), 7.45-7.35 (m, 2H), 7.28-7.23 (m, 1H), 5.77 (s, 2H); $^{13}$C NMR (125 MHz, DMSO-d$_6$) δ 161.6, 139.7, 132.8, 132.6, 130.5, 130.4, 129.6, 129.5, 127.8, 50.8; HRMS (TOF-ESI) calcd for C$_{10}$H$_8$ClN$_3$O$_2$Na[M+Na]$^+$: 260.0203, found: 260.0201.

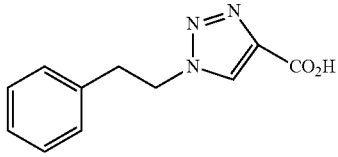 [SMILES: O=C(O)c1cn(CCc2ccccc2)nn1]

1-Phenethyl-1H-1,2,3-triazole-4-carboxylic acid (7r)

The reaction of 2-phenylethylazide (721 mg, 4.9 mmol), propiolic acid (274 mg, 3.92 mmol), CuSO$_4$ (40 mg, 0.25 mmol) and sodium ascorbate (100 mg, 0.50 mmol) in t-BuOH/H$_2$O (10 mL/10 mL) afforded the title acid (635 mg, 75% yield) as a white solid. $^1$H NMR (400 MHz, DMSO-d$_6$) δ 13.05 (s, 1H), 8.59 (s, 1H), 7.32-7.24 (m, 2H), 7.24-7.15 (m, 3H), 4.67 (t, J=7.2 Hz, 2H), 3.20 (t, J=7.2 Hz, 2H); $^{13}$C NMR (125 MHz, DMSO-d$_6$) δ 161.7, 139.4, 137.3, 128.9, 128.7, 128.4, 126.6, 50.6, 35.4; HRMS (TOF-ESI) calcd for C$_{11}$H$_{11}$N$_3$O$_2$Na[M+Na]$^+$: 240.0749, found: 240.0746.

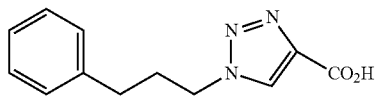 [SMILES: O=C(O)c1cn(CCCc2ccccc2)nn1]

1-(3-Phenylpropyl)-1H-1, 2, 3-triazole-4-carboxylic acid (7s)

The reaction of 3-phenylpropylazide (604 mg, 3.75 mmol), propiolic acid (224 mg, 3.2 mmol), CuSO$_4$ (25.6 mg, 0.16 mmol, 5 mol %) and sodium ascorbate (63 mg, 0.32 mmol, 10 mol %) in t-BuOH/H$_2$O (10 mL/10 mL) afforded the title acid (631 mg, 85% yield) as a white solid. $^1$H NMR (400 MHz, DMSO-d$_6$) δ 13.06 (bs, 1H), 8.74 (s, 1H), 7.33-7.26 (m, 2H), 7.24-7.16 (m, 3H), 4.42 (t, J=7.2 Hz, 2H), 2.57 (t, J=7.2 Hz, 2H), 2.17 (pent, J=7.2 Hz, 2H); $^{13}$C NMR (125 MHz, DMSO-d$_6$) δ 161.7, 140.6, 128.8, 128.4, 128.3, 126.0, 49.2, 31.8, 31.0; HRMS (TOF-ESI) calcd for C$_{12}$H$_{14}$N$_3$O$_2$ [M+H]$^+$: 232.1086, found: 232.1075.

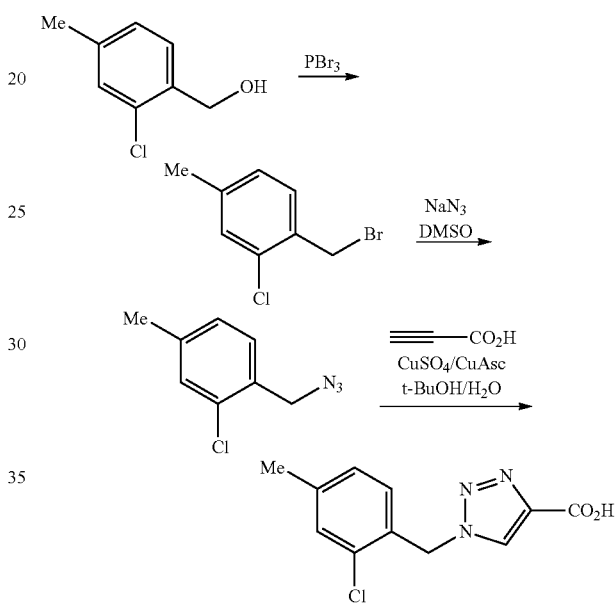

1-(2-Chloro-4-methylbenzyl)-1H-1,2,3-triazole-4-carboxylic acid (7t)

To a solution of 2-chloro-4-methylbenzyl alcohol (626 mg, 4 mmol) in dry DCM (10 mL) was added PBr$_3$ (4.4 mmol) dropwise at 0° C. The solution was stirred for 30 min at 0° C. and quenched with NaHCO$_3$ solution. The organic phase was separated and the aqueous phase extracted with DCM (10 mL×3). The combined organic phase was washed with brine, dried over Na$_2$SO$_4$ and evaporated to dryness. The residue was dissolved in dry DMSO (10 mL), treated with NaN$_3$ (390 mg, 6 mmol) and the mixture was stirred at 50° C. overnight. Then the reaction mixture was poured into water, extracted with ether (15 mL×3), dried over Na$_2$SO$_4$ and evaporated to get the azide (283 mg). The azide was then dissolved in t-BuOH (8 mL) and to the solution was added CuSO$_4$ (13 mg, 0.078 mmol), sodium ascorbate (31 mg, 0.156 mmol), H$_2$O (8 mL) and propiolic acid (109 mg, 1.56 mmol) and the mixture was sealed and stirred at room temperature overnight. The resulting suspension was poured into NaHCO$_3$ solution, and extracted with ether (15 mL×2) and the ethereal solution was discarded. The aqueous phase was acidified with 1N H$_2$SO$_4$ and extracted with EtOAc (15 mL×3), and the combined organic phase dried over Na$_2$SO$_4$ and evaporated to dryness to obtain the final acid (217 mg, 55% yield) as a white solid. $^1$H NMR (400 MHz, DMSO-d$_6$) δ 13.13 (bs, 1H), 8.69 (s, 1H), 7.36 (s, 1H), 7.20 (s, 2H), 5.71 (s, 2H), 2.30 (s, 3H); $^{13}$C NMR (125 MHz, DMSO-d$_6$) δ 161.6, 140.5, 139.6, 132.4, 130.6, 129.9, 129.7, 129.3, 128.4, 50.6, 20.3; HRMS (TOF-ESI) calcd for C$_{11}$H$_{10}$ClN$_3$O$_2$Na[M+Na]$^+$: 274.0359, found: 274.0354.

B. General Procedure for the Amide Coupling Reaction

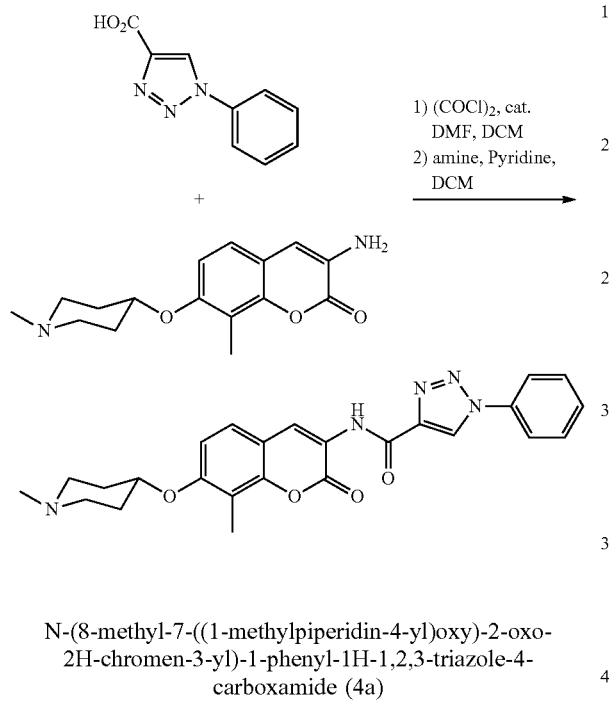

N-(8-methyl-7-((1-methylpiperidin-4-yl)oxy)-2-oxo-2H-chromen-3-yl)-1-phenyl-1H-1,2,3-triazole-4-carboxamide (4a)

To a solution of the triazole acid (0.13 mmol) in dry DCM (3 mL) was added sequentially (COCl)$_2$ (0.40 mmol) and DMF (5 μL) under Ar and the resulting solution was stirred at room temperature overnight. Then the solvent was removed in vacuo and the residue was put on the high vacuum for 30 min. To another oven-dried RBF was added the amine (0.067 mmol), dry DCM (3 mL) and pyridine (0.6 mmol). To the above solution was added a solution of the acid chloride in dry DCM (4 mL) via a syringe dropwise. After addition the solution was stirred at room temperature overnight. Then the mixture was directly loaded on a silica gel column and eluded with 5% MeOH in DCM to afford the title product (13 mg, 43% yield). $^1$H NMR (500 MHz, DMSO-d$_6$) δ 9.64 (s, 1H), 9.59 (s, 1H), 8.65 (s, 1H), 8.06-8.01 (m, 2H), 7.68-7.62 (m, 3H), 7.60-7.54 (m, 1H), 7.20-7.15 (m, 1H), 4.80-4.60 (m, 1H), 3.05-2.80 (m, 2H), 2.60-2.40 (m, 2H), 2.70 (s, 3H), 2.12-1.98 (m, 2H), 1.94-1.74 (m, 2H); One methyl group overlays with solvent residue peaks. $^{13}$C NMR (125 MHz, DMSO-d$_6$) δ 158.2, 157.9, 156.4, 149.2, 142.5, 136.1, 130.0, 129.4, 126.2, 125.6, 125.1, 120.8, 120.6, 113.6, 112.8, 110.8, 51.1, 44.4, 29.0, 8.2; HRMS (TOF-ESI) calcd for C$_{25}$H$_{26}$N$_5$O$_4$ [M+H]$^+$: 460.1985, found: 460.1971.

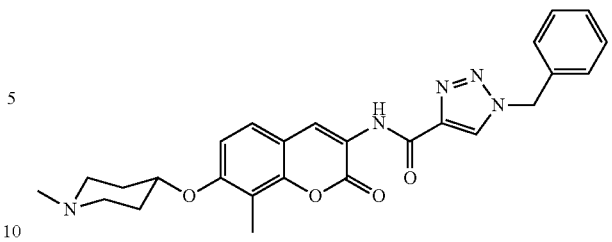

1-Benzyl-N-(8-methyl-7-((1-methylpiperidin-4-yl)oxy)-2-oxo-2H-chromen-3-yl)-1H-1,2,3-triazole-4-carboxamide (4b)

Following the general procedure, the title compound was obtained as a white solid (15 mg, 47% yield). $^1$H NMR (400 MHz, CDCl$_3$) δ 9.65 (s, 1H), 8.69 (s, 1H), 8.05 (s, 1H), 7.50-7.22 (m, 6H), 6.90-6.83 (m, 1H), 5.62 (s, 2H), 4.48 (bs, 1H), 2.74-2.56 (m, 2H), 2.50-2.24 (m, 8H), 2.12-1.98 (m, 2H), 1.98-1.83 (m, 2H); $^{13}$C NMR (125 MHz, CDCl$_3$) δ 158.71, 158.68, 157.0, 149.7, 143.1, 133.6, 129.3, 129.2, 128.3, 125.6, 125.4, 124.7, 121.0, 115.3, 113.1, 110.3, 72.3, 54.6, 52.2, 46.2, 30.7, 8.3; HRMS (TOF-ESI) calcd for C$_{26}$H$_{28}$N$_5$O$_4$ [M+H]$^+$: 474.2152; found: 474.2141.

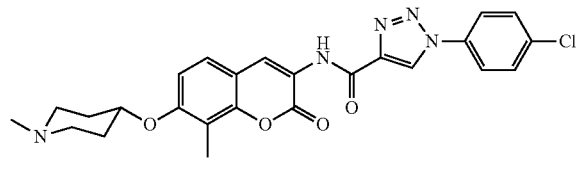 [SMILES: Cc1c(OC2CCN(C)CC2)ccc2cc(NC(=O)c3cn(-c4ccc(Cl)cc4)nn3)c(=O)oc12]

1-(4-chlorophenyl)-N-(8-methyl-7-((1-methylpiperidin-4-yl)oxy)-2-oxo-2H-chromen-3-yl)-1H-1,2,3-triazole-4-carboxamide (4c)

Following the general procedure, the title compound was obtained as light yellow solid (19 mg, 58% yield). $^1$H NMR (400 MHz, CDCl$_3$) δ 9.71 (s, 1H), 8.76 (s, 1H), 8.58, s, 1H), 7.82-7.73 (m, 2H), 7.63-7.54 (m, 2H), 7.35 (d, J=8.4 Hz, 1H), 6.89 (d, J=8.4 Hz, 1H), 4.56-4.46 (m, 1H), 2.78-2.63 (m, 2H), 2.55-2.40 (m, 2H), 2.38 (s, 3H), 2.37 (s, 3H), 2.16-2.03 (m, 2H), 2.02-1.89 (m, 2H); $^{13}$C NMR (125 MHz, CDCl$_3$ with minor CD$_3$OD) δ 158.7, 158.4, 156.8, 149.5, 143.0, 135.3, 134.6, 130.0, 125.6, 125.3, 124.0, 121.8, 120.6, 115.0, 112.9, 110.1, 70.8, 51.4, 45.4, 29.4, 29.1, 8.0; HRMS (TOF-ESI) calcd for C$_{25}$H$_{25}$ClN$_5$O$_4$ [M+H]$^+$: 494.1595; found: 494.1614.

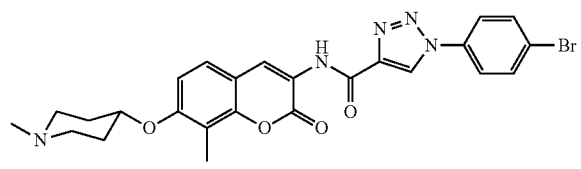 [SMILES: Cc1c(OC2CCN(C)CC2)ccc2cc(NC(=O)c3cn(-c4ccc(Br)cc4)nn3)c(=O)oc12]

1-(4-Bromophenyl)-N-(8-methyl-7-((1-m ethylpiperidin-4-yl)oxy)-2-oxo-2H-chromen-3-yl)-1H-1,2,3-triazole-4-carboxamide (4d)

Following the general procedure, title compound was obtained as light yellow solid (23 mg, 72% yield). $^1$H NMR (400 MHz, CDCl$_3$) δ 9.71 (s, 1H), 8.77 (s, 1H), 8.58 (s, 1H), 7.78-7.67 (m, 3H), 7.36 (d, J=8.4 Hz, 1H), 6.90 (d, J=8.4 Hz, 1H), 4.63-4.42 (m, 1H), 2.84-2.70 (m, 2H), 2.55-2.40 (m, 2H), 2.43 (s, 3H), 2.38 (s, 3H), 2.15 (m, 2H), 2.00 (m, 2H); $^{13}$C NMR (125 MHz, CDCl$_3$) δ 157.7, 157.4, 148.8, 142.6, 134.3, 131.2, 124.7, 123.9, 122.6, 122.5, 121.2, 120.1, 114.3, 112.2, 109.2, 50.8, 44.7, 29.0, 7.4; HRMS (TOF-ESI) calcd for C$_{25}$H$_{25}$$^{79}$BrN$_5$O$_4$ [M+H]$^+$: 538.1090; found: 538.1089.

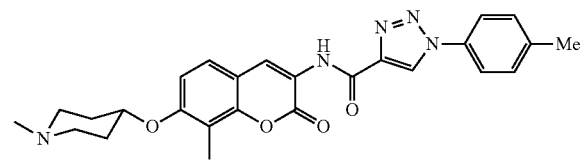 [SMILES: Cc1ccc(-n2cc(C(=O)Nc3cc4ccc(OC5CCN(C)CC5)c(C)c4oc3=O)nn2)cc1]

1-(4-methylphenyl)-N-(8-methyl-7-((1-methylpiperidin-4-yl)oxy)-2-oxo-2H-chromen-3-yl)-1H-1,2,3-triazole-4-carboxamide (4e)

Following the general procedure, the title compound was obtained as a white solid (17 mg, 53% yield). $^1$H NMR (400 MHz, CDCl$_3$) δ 9.71 (s, 1H), 8.75 (s, 1H), 8.55 (s, 1H), 7.64-7.70 (m, 2H), 7.41-7.36 (m, 2H), 7.34 (d, J=8.8 Hz, 1H), 6.89 (d, J=8.8 Hz, 1H), 4.54-4.41 (m, 1H), 2.75-2.58 (m, 2H), 2.46 (s, 3H), 2.44-2.31 (m, 8H), 2.10-1.99 (m, 2H), 1.99-1.87 (m, 2H); $^{13}$C NMR (125 MHz, CDCl$_3$) δ 158.7, 158.6, 157.1, 149.7, 143.2, 139.8, 134.1, 130.4, 125.5, 124.8, 123.7, 121.0, 120.6, 115.3, 113.0, 110.3, 52.3, 46.2, 30.7, 21.1, 8.3; HRMS (TOF-ESI) calcd for C$_{26}$H$_{28}$N$_5$O$_4$ [M+H]$^+$: 474.2141; found: 474.2143.

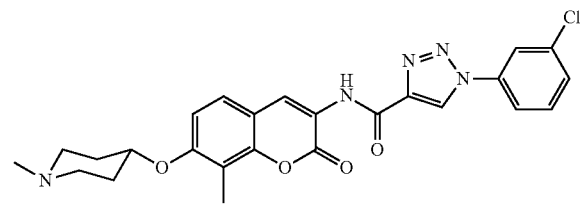 [SMILES: Cc1c(OC2CCN(C)CC2)ccc2cc(NC(=O)c3cn(-c4cccc(Cl)c4)nn3)c(=O)oc12]

1-(3-Chlorophenyl)-N-(8-methyl-7-((1-methylpiperidin-4-yl)oxy)-2-oxo-2H-chromen-3-yl)-1H-1,2,3-triazole-4-carboxamide (4f)

Following the general procedure, the title compound was obtained as an off-white solid (20 mg, 67% yield). $^1$H NMR (400 MHz, CDCl$_3$) δ 9.69 (s, 1H), 8.75 (s, 1H), 8.60 (s, 1H), 7.86 (s, 1H), 7.75-7.66 (m, 1H), 7.60-7.51 (m, 2H), 7.34 (d, J=8.4 Hz, 1H), 6.89 (d, J=8.4 Hz, 1H), 4.55-4.42 (m, 1H), 2.78-2.60 (m, 2H), 2.5-2.36 (m, 2H), 2.36 (s, 6H), 2.15-2.00 (m, 2H), 2.00-1.80 (m, 2H); $^{13}$C NMR (125 MHz, CDCl$_3$) δ 158.1, 157.7, 156.7, 149.2, 142.6, 137.1, 134.2, 131.6, 129.2, 126.2, 125.8, 125.3, 120.6, 120.4, 119.2, 113.5, 112.6, 110.9, 71.8, 51.7, 45.6, 30.1, 8.1; HRMS (TOF-ESI) calcd for C$_{25}$H$_{25}$$^{35}$ClN$_5$O$_4$ [M+H]$^+$: 494.1595; found: 494.1584.

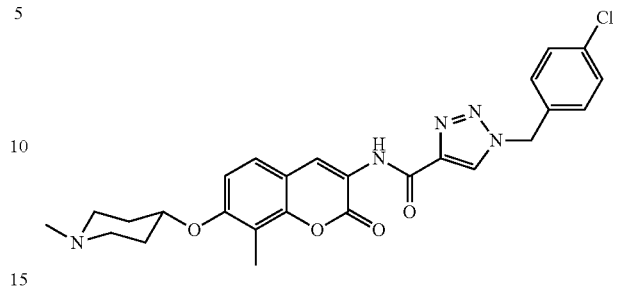

1-(4-Chlorobenzyl)-N-(8-methyl-7-((1-methylpiperidin-4-yl)oxy)-2-oxo-2H-chromen-3-yl)-1H-1,2,3-triazole-4-carboxamide (4g)

Following the general procedure, the 4-chlorobenzyl analogue was obtained as a white solid (24 mg, 79% yield). $^1$H NMR (400 MHz, CDCl$_3$) δ 9.65 (s, 1H), 8.71 (s, 1H), 8.06 (s, 1H), 7.43-7.39 (m, 2H), 7.33 (d, J=8.4 Hz, 1H), 7.30-7.25 (m, 2H), 6.88 (d, J=8.4 Hz, 1H), 5.60 (s, 2H), 4.60-4.48 (m, 1H), 2.85-2.66 (m, 2H), 2.65-2.55 (m, 2H), 2.42 (s, 3H), 2.36 (s, 3H), 2.23-2.08 (m, 2H), 2.05-1.92 (m, 2H); $^{13}$C NMR (125 MHz, CDCl$_3$) δ 158.8, 158.6, 156.9, 149.8, 143.3, 135.4, 132.2, 129.6, 125.6, 124.8, 121.1, 115.3, 113.2, 110.3, 53.9, 51.9, 46.0, 31.0, 30.2, 8.4; HRMS (TOF-ESI) calcd for C$_{26}$H$_{27}$ClN$_5$O$_4$ [M+H]$^+$: 508.1752; found: 508.1740.

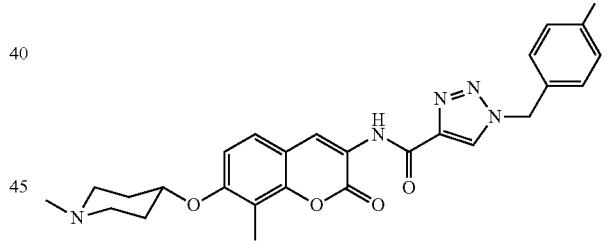

1-(4-Bromobenzyl)-N-(8-methyl-7-((1-methylpiperidin-4-yl)oxy)-2-oxo-2H-chromen-3-yl)-1H-1,2,3-triazole-4-carboxamide (4h)

Following the general procedure, the 4-bromobenzyl analogue was obtained as a white solid (24 mg, 73% yield). $^1$H NMR (400 MHz, CDCl$_3$) δ 9.65 (s, 1H), 8.70 (s, 1H), 8.07 (s, 1H), 7.60-7.54 (m, 2H), 7.33 (d, J=8.4 Hz, 1H), 7.24-7.19 (m, 2H), 6.88 (d, J=8.4 Hz, 1H), 5.58 (s, 2H), 4.51 (bs, 1H), 2.80-2.61 (m, 2H), 2.55-2.40 (m, 2H), 2.37 (s, 3H), 2.36 (s, 3H), 2.14-2.02 (m, 2H), 2.01-1.88 (m, 2H); $^{13}$C NMR (125 MHz, CDCl$_3$) δ 158.7, 158.6, 157.0, 149.7, 143.3, 132.7, 132.5, 129.8, 125.6, 125.5, 124.9, 123.4, 121.0, 115.3, 113.1, 110.3, 53.9, 52.1, 46.1, 30.9, 30.5, 8.4; HRMS (TOF-ESI) calcd for C$_{26}$H$_{27}$$^{79}$BrN$_5$O$_4$ [M+H]$^+$: 552.1246; found: 552.1235.

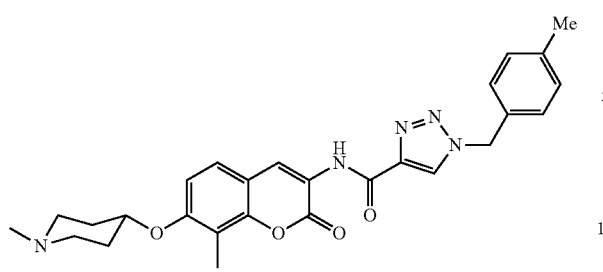

1-(4-Methylbenzyl)-N-(8-methyl-7-((1-methylpiperidin-4-yl)oxy)-2-oxo-2H-chromen-3-yl)-1H-1,2,3-triazole-4-carboxamide (4i)

Following the general procedure, the 4-methylbenzyl analogue was obtained as a white solid (17 mg, 59% yield). $^1$H NMR (400 MHz, CDCl$_3$) δ 9.65 (s, 1H), 8.70 (s, 1H), 8.02 (s, 1H), 7.33 (d, J=8.8 Hz, 1H), 7.23 (s, 4H), 6.87 (d, J=8.8 Hz, 1H), 5.57 (s, 2H), 4.56 (bs, 1H), 2.82-2.70 (m, 2H), 2.70-2.52 (m, 2H), 2.45 (bs, 3H), 2.39 (s, 3H), 2.36 (s, 3H), 2.26-2.11 (m, 2H), 2.08-1.93 (m, 2H); $^{13}$C NMR (125 MHz, CDCl$_3$) δ 158.8, 158.7, 156.7, 149.7, 143.0, 139.2, 130.6, 130.0, 128.4, 125.5, 124.6, 121.2, 115.2, 113.3, 110.2, 54.5, 51.8, 45.8, 30.9, 30.0, 21.2, 8.4; HRMS (TOF-ESI) calcd for C$_{27}$H$_{30}$N$_5$O$_4$ [M+H]$^+$: 488.2298; found: 488.2293.

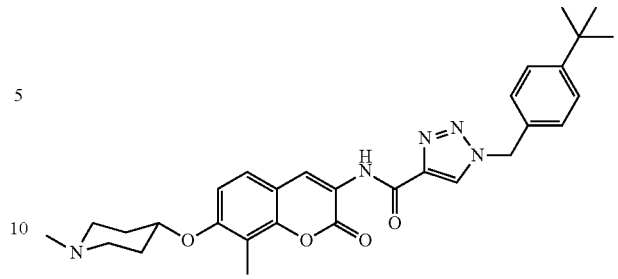

1-(4-tert-Butylbenzyl)-N-(8-methyl-7-((1-methylpiperidin-4-yl)oxy)-2-oxo-2H-chromen-3-yl)-1H-1,2,3-triazole-4-carboxamide (4k)

Following the general procedure, the title compound was obtained as a white solid (25 mg, 71% yield). $^1$H NMR (400 MHz, CDCl$_3$) δ 9.63 (s, 1H), 8.68 (s, 1H), 8.01 (s, 1H), 7.45-7.39 (m, 2H), 7.33-7.28 (m, 1H), 7.28-7.23 (m, 1H), 6.85 (d, J=8.4 Hz, 1H), 5.56 (s, 2H), 2.80-2.60 (m, 2H), 2.55-2.35 (m, 2H), 2.36 (s, 3H), 2.34 (s, 3H), 2.16-2.00 (m, 2H), 2.00-1.87 (m, 2H), 1.32 (s, 9H); $^{13}$C NMR (125 MHz, CDCl$_3$) δ 158.8, 158.7, 156.9, 152.5, 149.7, 143.0, 130.5, 128.2, 126.3, 125.6, 125.5, 124.7, 121.1, 115.3, 113.2, 110.3, 54.4, 52.0, 46.1, 34.7, 31.2, 30.5, 8.4; HRMS (TOF-ESI) calcd for C$_{30}$H$_{36}$N$_5$O$_4$ [M+H]$^+$: 530.2767; found: 530.2773.

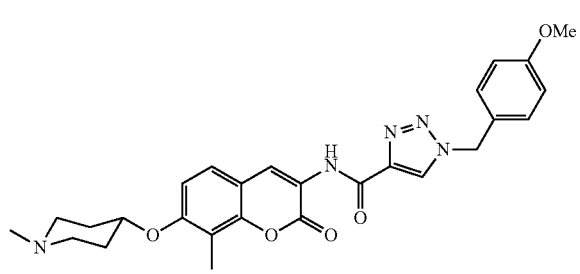 [SMILES: COc1ccc(Cn2cc(C(=O)Nc3cc4ccc(OC5CCN(C)CC5)c(C)c4oc3=O)nn2)cc1]

1-(4-Methoxybenzyl)-N-(8-methyl-7-((1-methylpiperidin-4-yl)oxy)-2-oxo-2H-chromen-3-yl)-1H-1,2,3-triazole-4-carboxamide (4j)

Following the general procedure, the 4-methoxybenzyl analogue was obtained as a white solid (20 mg, 67% yield). $^1$H NMR (400 MHz, CDCl$_3$) δ 9.64 (s, 1H), 8.70 (s, 1H), 8.01 (s, 1H), 7.35-7.28 (m, 2H), 6.97-6.92 (m, 2H), 6.87 (d, J=8.4 Hz, 1H), 5.55 (s, 2H), 4.53 (bs, 1H), 3.84 (s, 3H), 2.82-2.67 (m, 2H), 2.65-2.45 (m, 2H), 2.41 (bs, 3H), 2.35 (s, 3H), 2.19-2.07 (m, 2H), 2.04-1.90 (m, 2H); $^{13}$C NMR (125 MHz, CDCl$_3$) δ 160.2, 158.8, 158.7, 156.8, 149.7, 143.0, 129.9, 125.5, 125.4, 124.7, 121.2, 115.3, 114.7, 113.2, 110.3, 55.4, 54.2, 51.9, 45.9, 30.9, 30.2, 8.4; HRMS (TOF-ESI) calcd for C$_{27}$H$_{30}$N$_5$O$_5$ [M+H]$^+$: 504.2247; found: 504.2249.

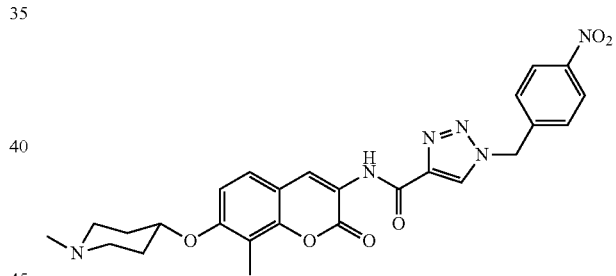

1-(4-Nitrobenzyl)-N-(8-methyl-7-((1-methylpiperidin-4-yl)oxy)-2-oxo-2H-chromen-3-yl)-1H-1,2,3-triazole-4-carboxamide (4l)

Following the general procedure, the title compound was obtained as a yellow solid (17 mg, 55% yield). $^1$H NMR (400 MHz, CDCl$_3$) δ 9.65 (s, 1H), 8.69 (s, 1H), 8.27 (d, J=8.4 Hz, 2H), 8.20 (s, 1H), 7.48 (d, J=8.4 Hz, 2H), 7.34 (d, J=8.4 Hz, 1H), 6.86 (d, J=8.4 Hz, 1H), 5.75 (s, 2H), 4.73 (bs, 1H), 3.20-2.93 (m, 2H), 2.80-2.60 (m, 2H), 2.60-2.40 (m, 2H), 2.35 (s, 3H), 2.23-2.10 (m, 2H); $^{13}$C NMR (125 MHz, CDCl$_3$) δ 158.5, 158.4, 156.0, 149.7, 148.3, 143.5, 140.6, 128.5, 126.0, 125.9, 124.54, 124.50, 121.4, 115.0, 113.6, 109.9, 53.6, 50.0, 44.5, 29.7, 28.0, 8.4; HRMS (TOF-ESI) calcd for C$_{26}$H$_{27}$N$_6$O$_6$ [M+H]$^+$: 519.1992; found: 519.2000.

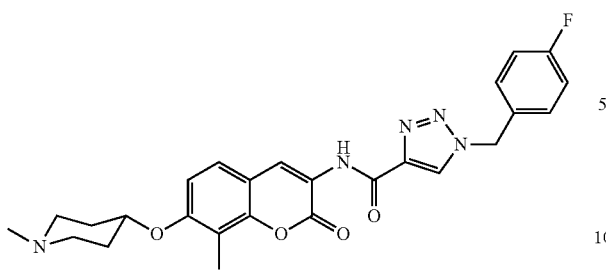

1-(4-Fluorobenzyl)-N-(8-methyl-7-((1-methylpiperidin-4-yl)oxy)-2-oxo-2H-chromen-3-yl)-1H-1,2,3-triazole-4-carboxamide (4m)

Following the general procedure, the title compound was obtained as a white solid (19 mg, 58% yield). $^1$H NMR (400 MHz, CDCl$_3$) δ 9.61 (s, 1H), 8.66 (s, 1H), 8.04 (s, 1H), 7.36-7.28 (m, 3H), 7.13-7.05 (m, 2H), 6.84 (d, J=8.4 Hz, 1H), 5.57 (s, 2H), 4.51-4.40 (m, 1H), 2.75-2.57 (m, 2H), 2.50-2.35 (m, 2H), 2.33 (s, 3H), 2.32 (s, 3H), 2.10-1.97 (m, 2H), 1.96-1.85 (m, 2H); $^{13}$C NMR (125 MHz, CDCl$_3$) δ 164.0, 162.0, 158.6, 157.9 (d, $J_{C-F}$=211.3 Hz), 149.7, 143.2, 130.23, 130.17, 129.5 (d, $J_{C-F}$=3.6 Hz), 125.5 (d, $J_{C-F}$=5.5 Hz), 124.8, 121.0, 116.4, 116.3, 115.3, 113.0, 110.3, 53.8, 52.2, 46.1, 30.6, 29.6, 8.3; $^{19}$F NMR (MHz, CDCl$_3$) δ (−111.6)-(−111.9); HRMS (TOF-ESI) calcd for C$_{26}$H$_{27}$FN$_5$O$_4$ [M+H]$^+$: 492.2047; found: 492.2035.

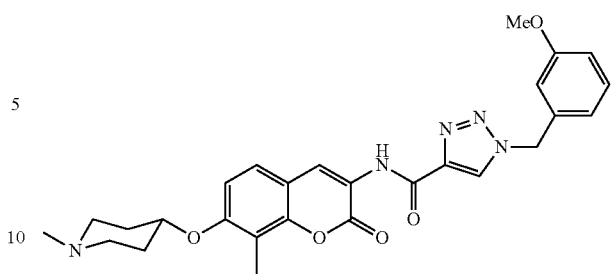

1-(3-Methoxybenzyl)-N-(8-methyl-7-((1-methylpiperidin-4-yl)oxy)-2-oxo-2H-chromen-3-yl)-1H-1,2,3-triazole-4-carboxamide (4o)

Following the general procedure, the title compound was obtained as a light yellow solid (21 mg, 62% yield). $^1$H NMR (400 MHz, CDCl$_3$) δ 9.63 (s, 1H), 8.68 (s, 1H), 8.04 (s, 1H), 7.35-7.29 (m, 2H), 6.95-6.80 (m, 4H), 5.56 (s, 2H), 4.54 (bs, 1H), 3.80 (s, 3H), 2.85-2.70 (m, 2H), 2.70-2.50 (m, 2H), 2.43 (s, 3H), 2.34 (s, 3H), 2.25-2.05 (m, 2H), 2.05-1.90 (m, 2H); $^{13}$C NMR (125 MHz, CDCl$_3$) δ 160.2, 158.73, 158.68, 158.67, 149.7, 143.1, 135.0, 134.0, 125.7, 125.6, 124.6, 121.2, 120.4, 115.2, 114.6, 113.9, 113.3, 110.2, 53.3, 54.6, 51.7, 45.7, 29.8, 8.4; HRMS (TOF-ESI) calcd for C$_{27}$H$_{30}$N$_5$O$_5$ [M+H]$^+$: 504.2247; found: 504.2242.

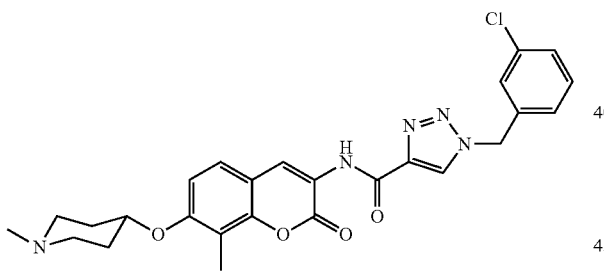 [SMILES: Cc1c(OC2CCN(C)CC2)ccc2cc(NC(=O)c3cn(Cc4ccc([N+](=O)[O-])cc4)nn3)c(=O)oc12]

1-(3-Chlorobenzyl)-N-(8-methyl-7-((1-methylpiperidin-4-yl)oxy)-2-oxo-2H-chromen-3-yl)-1H-1,2,3-triazole-4-carboxamide (4n)

Following the general procedure, the 3-chlorobenzyl analogue was obtained as a white solid (15 mg, 44% yield). $^1$H NMR (400 MHz, CDCl$_3$) δ 9.65 (s, 1H), 8.70 (s, 1H), 8.09 (s, 1H), 7.42-7.30 (m, 4H), 7.23-7.19 (m, 1H), 6.90-6.85 (d, J=8.4 Hz, 1H), 5.60 (s, 2H), 4.56-4.44 (m, 1H), 2.75-2.62 (m, 2H), 2.50-2.35 (m, 2H), 2.36 (s, 6H), 2.18-2.00 (m, 2H), 2.00-1.87 (m, 2H); $^{13}$C NMR (125 MHz, CDCl$_3$) δ 158.7, 158.5, 157.1, 149.7, 143.3, 135.5, 135.3, 130.6, 129.4, 128.3, 126.2, 125.7, 125.5, 124.9, 121.0, 115.3, 113.1, 110.3, 72.1, 53.9, 52.2, 46.2, 30.6, 29.7, 8.4; HRMS (TOF-ESI) calcd for C$_{26}$H$_{27}$ClN$_5$O$_4$ [M+H]$^+$: 508.1752, found: 508.1749.

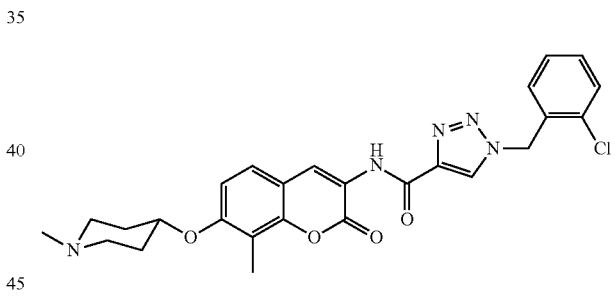

1-(2-Chlorobenzyl)-N-(8-methyl-7-((1-methylpiperidin-4-yl)oxy)-2-oxo-2H-chromen-3-yl)-1H-1,2,3-triazole-4-carboxamide (4p)

Following the general procedure, the 2-chlorobenzyl analogue was obtained as a white solid (30 mg, 98% yield). $^1$H NMR (400 MHz, CDCl$_3$) δ 9.66 (s, 1H), 8.71 (s, 1H), 8.15 (s, 1H), 7.51-7.47 (m, 1H), 7.42-7.35 (m, 1H), 7.35-7.31 (m, 3H), 6.88 (d, J=8.4 Hz, 1H), 5.76 (s, 2H), 4.53 (bs, 1H), 2.80-2.68 (m, 2H), 2.62-2.46 (m, 2H), 2.42 (bs, 3H), 2.36 (s, 3H), 2.22-2.06 (m, 2H), 2.04-1.90 (m, 2H); $^{13}$C NMR (125 MHz, CDCl$_3$) δ 158.7, 156.8, 149.7, 143.0, 133.8, 131.5, 130.79, 130.77, 130.2, 127.8, 125.9, 125.5, 124.7, 121.1, 115.3, 113.2, 110.3, 52.0 (two peaks overlapped), 45.9, 30.9, 30.2, 8.4; HRMS (TOF-ESI) calcd for C$_{26}$H$_{27}$ClN$_5$O$_4$ [M+H]$^+$: 508.1752; found: 508.1739.

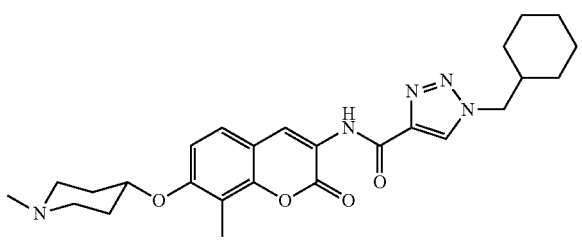 [SMILES: Cc1c(OC2CCN(C)CC2)ccc2cc(NC(=O)c3cn(CC4CCCCC4)nn3)c(=O)oc12]

1-(Cyclohexylmethyl)-N-(8-methyl-7-((1-methylpiperidin-4-yl)oxy)-2-oxo-2H-chromen-3-yl)-1H-1,2,3-triazole-4-carboxamide (4q)

Following the general procedure, the title compound was obtained as an off-white solid (25 mg, 78% yield). $^1$H NMR (400 MHz, CDCl$_3$) δ 9.66 (s, 1H), 8.73 (s, 1H), 8.11 (s, 1H), 7.34 (d, J=8.4 Hz, 1H), 6.88 (d, J=8.4 Hz, 1H), 4.58-4.46 (m, 1H), 4.29 (d, J=7.2 Hz, 1H), 2.78-2.66 (m, 2H), 2.58-2.42 (m, 2H), 2.40 (s, 3H), 2.36 (s, 3H), 2.20-2.05 (m, 2H), 2.05-1.86 (m, 3H), 1.85-1.60 (m, 5H), 1.35-1.15 (m, 3H), 1.12-0.97 (m, 2H); $^{13}$C NMR (125 MHz, CDCl$_3$) δ 159.0, 158.7, 156.9, 149.7, 142.6, 126.0, 125.5, 124.7, 121.2, 115.3, 113.2, 110.3, 56.9, 52.0, 46.0, 38.7, 30.4, 25.9, 25.4, 8.4; HRMS (TOF-ESI) calcd for C$_{26}$H$_{33}$N$_5$O$_4$Na[M+Na]$^+$: 502.2430; found: 502.2425.

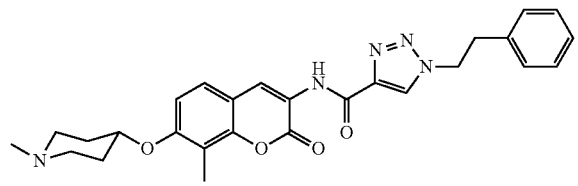 [SMILES: Cc1c(OC2CCN(C)CC2)ccc2cc(NC(=O)c3cn(CCc4ccccc4)nn3)c(=O)oc12]

N-(8-methyl-7-((1-methylpiperidin-4-yl)oxy)-2-oxo-2H-chromen-3-yl)-1-phenethyl-1H-1,2,3-triazole-4-carboxamide (4r)

Following the general procedure, the title compound was obtained as a light yellow solid (10 mg, 30% yield). $^1$H NMR (400 MHz, CDCl$_3$) δ 9.64 (s, 1H), 8.70 (s, 1H), 7.85 (s, 1H), 7.36-7.25 (m, 4H), 7.15-7.09 (m, 2H), 6.90-6.85 (m, 1H), 4.70 (t, J=7.2 Hz, 2H), 4.55-4.40 (m, 1H), 3.28 (t, J=7.2 Hz, 2H), 2.76-2.60 (m, 2H), 2.50-2.35 (m, 2H), 2.36 (s, 6H), 2.12-2.00 (m, 2H), 1.98-1.86 (m, 2H); $^{13}$C NMR (125 MHz, CDCl$_3$) δ 158.75, 158.74, 157.0, 149.7, 142.5, 136.3, 129.0, 128.6, 127.4, 125.9, 125.4, 124.7, 121.1, 115.3, 113.1, 110.3, 72.2 (b), 52.3 (b), 52.1, 46.2, 36.5, 30.7, 8.4; HRMS (TOF-ESI) calcd for C$_{27}$H$_{30}$N$_5$O$_4$ [M+H]$^+$: 488.2298; found: 488.2298.

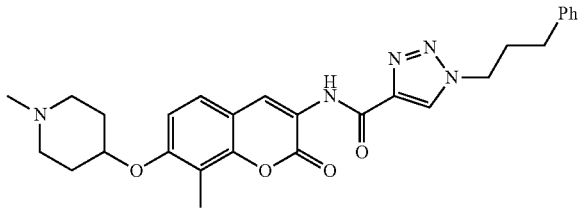 [SMILES: Cc1c(OC2CCN(C)CC2)ccc2cc(NC(=O)c3cn(CCCc4ccccc4)nn3)c(=O)oc12]

N-(8-methyl-7-((1-methylpiperidin-4-yl)oxy)-2-oxo-2H-chromen-3-yl)-1-(3-phenylpropyl)-1H-1,2,3-triazole-4-carboxamide (4s)

Following the general procedure, the title compound was obtained as a white solid (14 mg, 41% yield). $^1$H NMR (400 MHz, CDCl$_3$) δ 9.66 (s, 1H), 8.73 (s, 1H), 8.12 (s, 1H), 7.37-7.31 (m, 1H), 7.28-7.22 (m, 1H), 7.22-7.18 (m, 2H), 6.90-6.85 (m, 1H), 4.62-4.52 (m, 1H), 4.46 (t, J=7.2 Hz, 2H), 2.90-2.75 (m, 2H), 2.71 (t, J=7.2 Hz, 2H), 2.68-2.52 (m, 2H), 2.46 (s, 3H), 2.63 (s, 3H), 2.34 (pent, J=7.2 Hz, 2H), 2.28-2.12 (m, 2H), 2.08-1.95 (m, 2H); $^{13}$C NMR (125 MHz, CDCl$_3$) δ 158.9, 158.7, 156.7, 149.8, 142.8, 139.7, 128.8, 128.5, 126.6, 125.7, 125.6, 124.7, 121.3, 115.3, 113.4, 110.2, 51.7, 50.0, 45.7, 32.4, 31.5, 29.9, 8.4; HRMS (TOF-ESI) calcd for C$_{28}$H$_{32}$N$_5$O$_4$ [M+H]$^+$: 502.2454; found: 502.2436.

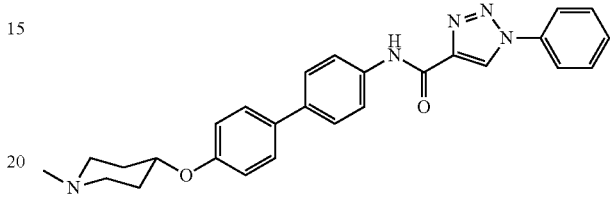

N-(4'-((1-methylpiperidin-4-yl)oxy)-[1,1'-biphenyl]-4-yl)-1-phenyl-1H-1,2,3-triazole-4-carboxamide (5a)

Following the general procedure, the title compound was obtained as a white solid (21 mg, 70% yield). $^1$H NMR (400 MHz, CDCl$_3$) δ 9.07 (s, 1H), 8.64 (s, 1H), 7.84-7.77 (m, 4H), 7.64-7.57 (m, 4H), 7.57-7.50 (m, 3H), 7.02-6.98 (m, 2H), 4.43-4.33 (m, 1H), 2.80-2.65 (m, 2H), 2.38-2.25 (m, 5H), 2.11-2.00 (m, 2H), 1.97-1.82 (m, 2H); $^{13}$C NMR (125 MHz, CDCl$_3$) δ 157.8, 156.6, 143.8, 137.1, 136.3, 135.9, 133.1, 129.9, 129.5, 127.8, 127.1, 124.2, 120.7, 120.3, 116.3, 71.3, 52.2, 45.8, 30.2; HRMS (TOF-ESI) calcd for C$_{27}$H$_{28}$N$_5$O$_2$ [M+H]$^+$: 454.2243; found: 454.2238.

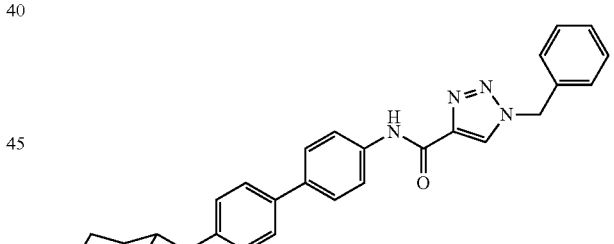

1-Benzyl-N-(4'-((1-methylpiperidin-4-yl)oxy)-[1,1'-biphenyl]-4-yl)-1H-1,2,3-triazole-4-carboxamide (5b)

Following the general procedure, the benzyl analogue was obtained as a white solid (17 mg, 55% yield). $^1$H NMR (400 MHz, CDCl$_3$) δ 8.99 (s, 1H), 8.08 (s, 1H), 7.76-7.72 (m, 2H), 7.60-7.50 (m, 4H), 7.46-7.40 (m, 3H), 7.36-7.31 (m, 2H), 7.03-6.97 (m, 2H), 5.62 (s, 2H), 4.44-4.33 (1H), 2.80-2.65 (m, 2H), 2.40-2.22 (m, 5H), 2.10-1.98 (m, 2H), 1.97-1.82 (m, 2H); $^{13}$C NMR (125 MHz, CDCl$_3$) δ 157.7, 156.6, 143.8, 137.0, 136.1, 133.6, 133.1, 129.4, 129.2, 128.3, 127.9, 127.2, 125.7, 120.1, 116.3, 72.1, 54.7, 52.7, 46.2, 30.9; HRMS (TOF-ESI) calcd for C$_{28}$H$_{30}$N$_5$O$_2$ [M+H]$^+$: 468.2400; found: 468.2407.

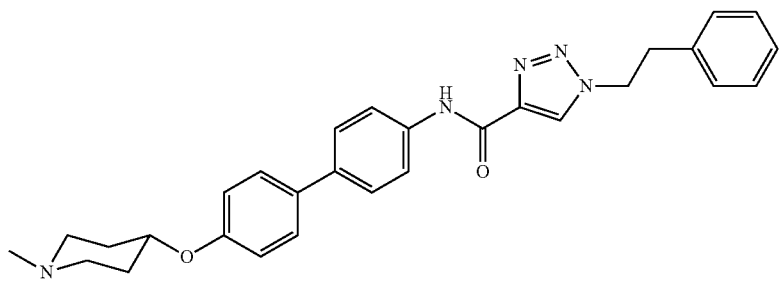 [SMILES: CN1CCC(Oc2ccc(-c3ccc(NC(=O)c4cn(CCc5ccccc5)nn4)cc3)cc2)CC1]

N-(4'-((1-methylpiperidin-4-yl)oxy)-[1,1'-biphenyl]-4-yl)-11-phenethyl-1H-1,2,3-triazole-4-carboxamide (5c)

Following the general procedure, the title compound was obtained as a white solid (18 mg, 56% yield). $^1$H NMR (400 MHz, CDCl$_3$) δ 8.99 (s, 1H), 7.92 (s, 1H), 7.78-7.73 (m, 2H), 7.60-7.50 (m, 4H), 7.37-7.26 (m, 3H), 7.16-7.11 (m, 2H), 7.02-6.98 (m, 2H), 4.70 (t, J=7.2 Hz, 2H), 4.48-4.40 (m, 1H), 3.28 (t, J=7.2 Hz, 2H), 2.90-2.74 (m, 2H), 2.60-2.45 (m, 2H), 2.40 (s, 3H), 2.17-2.06 (m, 2H), 2.01-1.89 (m, 2H); $^{13}$C NMR (125 MHz, CDCl$_3$) δ 157.7, 156.7, 143.2, 136.9, 136.3, 136.2, 133.3, 129.0, 128.6, 127.9, 127.4, 127.2, 125.9, 120.1, 116.3, 52.1, 51.9, 45.6, 36.5, 30.1, 22.6; HRMS (TOF-ESI) calcd for C$_{29}$H$_{32}$N$_5$O$_2$ [M+H]$^+$: 482.2556; found: 482.2556.

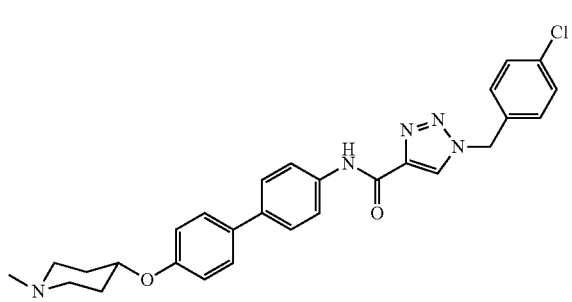 [SMILES: CN1CCC(Oc2ccc(-c3ccc(NC(=O)c4cn(Cc5ccc(Cl)cc5)nn4)cc3)cc2)CC1]

1-(4-Chlorobenzyl)-N-(4'-((1-methylpiperidin-4-yl)oxy)-[1, 1'-biphenyl]-4-yl)-1H-1,2,3-triazole-4-carboxamide (5d)

Following the general procedure, the 4-chlorobenzyl analogue was obtained (12 mg, 35% yield) as a white solid. $^1$H NMR (400 MHz, CDCl$_3$) δ 8.17 (s, 1H), 7.74-7.66 (m, 2H), 7.56-7.44 (m, 4H), 7.39-7.32 (m, 2H), 7.27-7.22 (m, 2H), 6.98-6.90 (m, 2H), 5.55 (s, 2H), 4.44-4.32 (m, 1H), 2.79-2.61 (m, 2H), 2.43-2.25 (m, 5H), 2.10-1.95 (m, 2H), 1.95-1.80 (m, 2H); $^{13}$C NMR (125 MHz, CD$_3$OD with minor CDCl$_3$, ref CDCl$_3$) δ 156.2, 154.5, 141.2, 135.4, 133.2, 132.6, 131.1, 130.2, 128.0, 126.9, 125.6, 125.5, 124.2, 118.7, 114.2, 50.4, 43.7, 28.5; HRMS (TOF-ESI) calcd for C$_{28}$H$_{29}$ClN$_5$O$_2$ [M+H]$^+$: 502.2010, found: 502.2006.

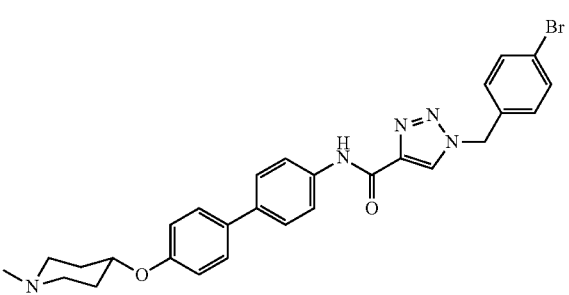 [SMILES: CN1CCC(Oc2ccc(-c3ccc(NC(=O)c4cn(Cc5ccc(Br)cc5)nn4)cc3)cc2)CC1]

1-(4-Bromobenzyl)-N-(4'-((1-methylpiperidin-4-yl)oxy)-[1,1'-biphenyl]-4-yl)-1H-1,2,3-triazole-4-carboxamide (5e)

Following the general procedure, the 4-bromobenzyl analogue was obtained as a white solid (21 mg, 57% yield). $^1$H NMR (400 MHz, DMSO-d$_6$) δ 10.53 (s, 1H), 8.85 (s, 1H), 7.91-7.86 (m, 2H), 7.65-7.55 (m, 6H), 7.37-7.32 (m, 2H), 7.06-7.00 (m, 2H), 5.70 (s, 2H), 4.43 (bs, 1H), 2.80-2.62 (m, 2H), 2.37-2.15 (m, 5H), 2.02-1.91 (m, 2H), 1.74-1.62 (m, 2H); $^{13}$C NMR (125 MHz, DMSO-d$_6$) δ 158.2, 156.4, 143.1, 137.3, 135.2, 135.0, 132.2, 131.8, 130.3, 127.6, 127.4, 126.2, 121.6, 120.7, 116.2, 71.6, 52.4, 52.2, 45.5, 30.3; HRMS (TOF-ESI) calcd for C$_{28}$H$_{29}$$^{79}$BrN$_5$O$_2$ [M+H]$^+$: 546.1505, found: 546.1494.

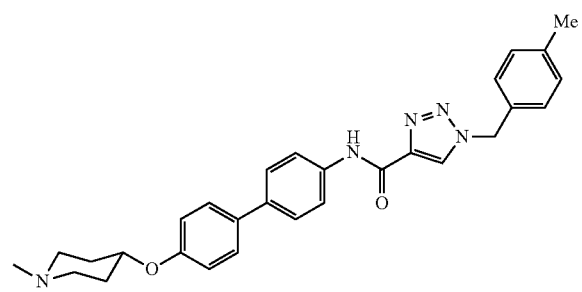 [SMILES: Cc1ccc(Cn2cc(C(=O)Nc3ccc(-c4ccc(OC5CCN(C)CC5)cc4)cc3)nn2)cc1]

1-(4-Methylbenzyl)-N-(4'-((1-methylpiperidin-4-yl)oxy)-[1,1'-biphenyl]-4-yl)-1H-1,2,3-triazole-4-carboxamide (5f)

Following the general procedure, the 4-methylbenzyl analogue was obtained (20 mg, 63% yield) as a white solid. $^1$H NMR (400 MHz, CDCl$_3$) δ 9.01 (s, 1H), 7.77-7.72 (m, 2H), 7.59-7.50 (m, 4H), 7.23 (s, 4H), 7.01-6.97 (m, 2H), 5.56 (s, 2H), 4.43 (bs, 1H), 2.86-2.73 (m, 2H), 2.60-2.42 (m, 2H), 2.40 (s, 3H), 2.39 (s, 3H), 2.17-2.05 (m, 2H), 2.00-1.87 (m, 2H); $^{13}$C NMR (125 MHz, CDCl$_3$) δ 158.2, 156.4, 143.0, 137.7, 137.4, 135.1, 132.6, 132.0, 129.4, 128.1, 127.4, 127.3, 126.2, 120.7, 116.2, 71.4, 53.0, 52.1, 45.3, 30.1, 20.7; HRMS (TOF-ESI) calcd for C$_{29}$H$_{32}$N$_5$O$_2$ [M+H]$^+$: 482.2556; found: 482.2545.

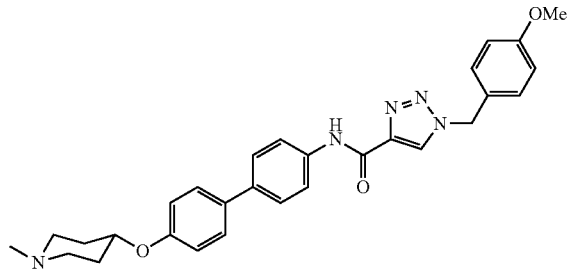 [SMILES: COc1ccc(Cn2cc(C(=O)Nc3ccc(-c4ccc(OC5CCN(C)CC5)cc4)cc3)nn2)cc1]

1-(4-Methoxybenzyl)-N-(4'-((1-methylpiperidin-4-yl)oxy)-[1,1'-biphenyl]-4-yl)-1H-1,2,3-triazole-4-carboxamide (5g)

Following the general procedure, the 4-methoxybenzyl analogue was obtained as an off-white solid (14 mg, 42% yield). $^1$H NMR (400 MHz, CDCl$_3$) δ 8.97 (s, 1H), 8.02 (s, 1H), 7.75-7.69 (m, 2H), 7.57-7.47 (m, 4H), 7.29-7.27 (m, 1H), 7.00-6.90 (m, 4H), 5.52 (s, 2H), 4.40 (bs, 1H), 3.82 (s, 3H), 2.82-2.70 (m, 2H), 2.58-2.35 (m, 2H). 2.37 (s, 3H), 2.15-2.03 (m, 2H), 1.97-1.85 (m, 2H); $^{13}$C NMR (125 MHz, CDCl$_3$ and minor CD$_3$OD) δ 160.1, 157.8, 156.5, 143.5, 136.9, 136.0, 133.3, 129.8, 127.9, 127.1, 125.7, 125.5, 120.1, 116.3, 114.6, 55.3, 54.2, 51.8, 45.5, 30.8; HRMS (TOF-ESI) calcd for C$_{29}$H$_{32}$N$_5$O$_3$ [M+H]$^+$: 498.2505; found: 498.2499.

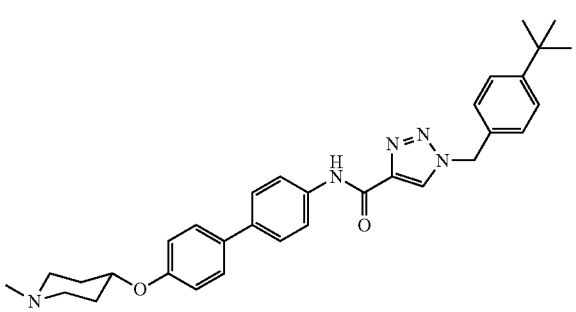 [SMILES: CN1CCC(Oc2ccc(-c3ccc(NC(=O)c4cn(Cc5ccc(C(C)(C)C)cc5)nn4)cc3)cc2)CC1]

1-(4-tert-Butylbenzyl)-N-(4'-((1-methylpiperidin-4-yl)oxy)-[1,1'-biphenyl]-4-yl)-1H-1,2,3-triazole-4-carboxamide (5h)

Following the general procedure, the title compound was obtained as a white solid (16 mg, 46% yield). $^1$H NMR (400 MHz, CDCl$_3$) δ 8.97 (s, 1H), 8.03 (s, 1H), 7.72 (d, J=8.4 Hz, 2H), 7.54 (d, J=8.4 Hz, 2H), 7.51 (d, J=8.4 Hz, 2H), 7.43 (d, J=8.4 Hz, 2H), 7.29-7.24 (m, 2H), 6.97 (d, J=8.4 Hz, 2H), 5.56 (s, 2H), 4.44 (bs, 1H), 2.95-2.75 (m, 2H), 2.45 (s, 3H), 2.30-2.05 (m, 2H), 2.05-1.90 (m, 2H), 1.32 (s, 9H); $^{13}$C NMR (125 MHz, CD$_3$OD) δ 158.2, 156.2, 150.8, 143.1, 137.4, 135.1, 132.7, 127.8, 127.5, 127.3, 126.2, 125.6, 120.7, 116.3, 52.9, 34.3, 31.0, 30.7; HRMS (TOF-ESI) calcd for C$_{32}$H$_{38}$N$_5$O$_2$ [M+H]$^+$: 524.3026; found: 524.3029.

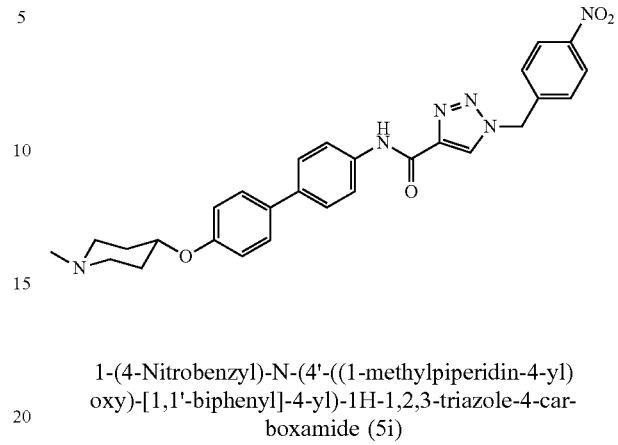

1-(4-Nitrobenzyl)-N-(4'-((1-methylpiperidin-4-yl)oxy)-[1,1'-biphenyl]-4-yl)-1H-1,2,3-triazole-4-carboxamide (5i)

Following the general procedure the title compound was obtained as a yellow solid (20 mg, 59% yield). $^1$H NMR (400 MHz, CDCl$_3$) δ 8.97 (s, 1H), 8.27 (d, J=8.4 Hz, 2H), 8.18 (s, 2H), 7.73 (d, J=8.4 Hz, 1H), 7.56 (d, J=8.4 Hz, 2H), 7.51 (d, J=8.4 Hz, 2H), 7.47 (d, J=8.4 Hz, 2H), 6.97 (d, J=8.4 Hz, 2H), 5.73 (s, 2H), 4.48 (bs, 1H), 2.95-2.80 (m, 2H), 2.75-2.55 (m, 2H), 2.47 (s, 3H), 2.30-2.12 (m, 2H), 2.10-1.86 (m, 2H); $^{13}$C NMR (125 MHz, CDCl$_3$) δ 157.3, 156.9, 148.4, 144.3, 140.6, 137.2, 136.0, 133.2, 128.8, 128.0, 127.3, 126.0, 124.6, 120.2, 116.4, 53.6, 53.5, 52.5, 46.0, 30.5; HRMS (TOF-ESI) calcd for C$_{28}$H$_{29}$N$_6$O$_4$ [M+H]$^+$: 513.2250; found: 513.2270.

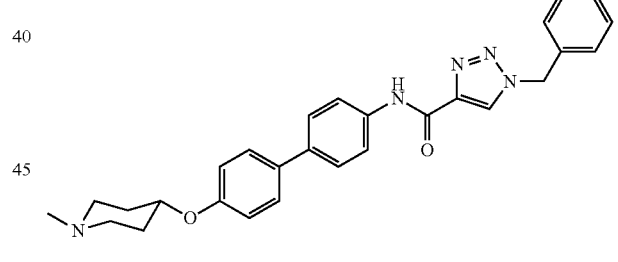

1-(4-Fluorobenzyl)-N-(4'-((1-methylpiperidin-4-yl)oxy)-[1,1'-biphenyl]-4-yl)-1H-1,2,3-triazole-4-carboxamide (5j)

Following the general procedure, the title compound was obtained as a white solid (17 mg, 53% yield). $^1$H NMR (400 MHz, CDCl$_3$) δ 8.97 (s, 1H), 8.10-8.06 (m, 1H), 7.80-7.70 (m, 2H), 7.60-7.49 (m, 4H), 7.38-7.31 (m, 2H), 7.18-7.08 (m, 2H), 7.04-6.96 (m, 2H), 5.59 (s, 2H), 4.45-4.30 (m, 1H), 2.81-2.68 (m, 2H), 2.45-2.25 (m, 5H), 2.13-2.00 (m, 2H), 1.98-1.85 (m, 2H); $^{13}$C NMR (125 MHz, CDCl$_3$) δ 163.1 (d, J$_{C-F}$=247.4 Hz), 157.6, 156.9, 143.9, 137.1, 136.1, 133.1, 130.3 (d, J$_{C-F}$=8.1 Hz), 129.5 (d, J$_{C-F}$=2.5 Hz), 127.9, 127.3, 125.6, 120.2, 116.5, 116.4, 72.1, 54.0, 54.7, 46.2, 30.9; HRMS (TOF-ESI) calcd for C$_{28}$H$_{29}$FN$_5$O$_2$ [M+H]$^+$: 486.2305; found: 486.2305.

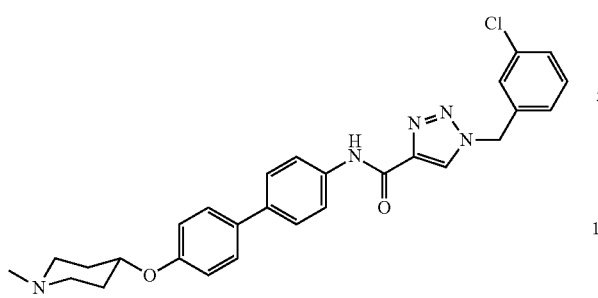 [SMILES: CN1CCC(Oc2ccc(-c3ccc(NC(=O)c4cn(Cc5ccc([N+](=O)[O-])cc5)nn4)cc3)cc2)CC1]

1-(3-Chlorobenzyl)-N-(4'-((1-methylpiperidin-4-yl)oxy)-[1,1'-biphenyl]-4-yl)-1H-1,2,3-triazole-4-carboxamide (5k)

Following the general procedure, the title compound was obtained as a white solid (12 mg, 36% yield). $^1$H NMR (400 MHz, CDCl$_3$) δ 8.98 (s, 1H), 8.12 (s, 1H), 7.79-7.70 (m, 2H), 7.61-7.48 (m, 4H), 7.43-7.30 (m, 3H), 7.25-7.16 (m, 2H), 7.04-6.96 (m, 2H), 5.59 (s, 2H), 4.45-4.30 (m, 1H), 2.85-2.66 (m, 2H), 2.45-2.24 (m, 5H), 2.11-2.00 (m, 2H), 1.96-1.83 (m, 2H); $^{13}$C NMR (125 MHz, CDCl$_3$) δ 157.5, 156.9, 144.0, 137.1, 136.0, 135.5, 135.3, 133.1, 130.6, 129.4, 128.3, 127.9, 127.2, 126.2, 125.7, 120.2, 116.3, 72.1, 53.9, 52.6, 46.2, 30.8; HRMS (TOF-ESI) calcd for C$_{28}$H$_{29}$ClN$_5$O$_2$ [M+H]$^+$: 502.2010; found: 502.2005.

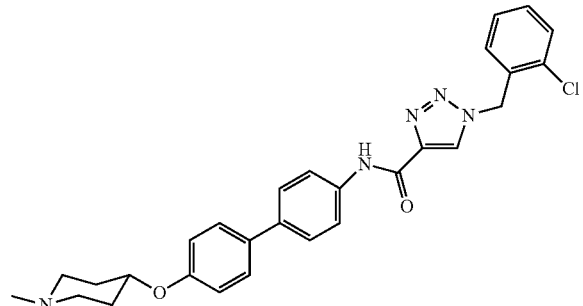

1-(2-Chlorobenzyl)-N-(4'-((1-methylpiperidin-4-yl)oxy)-[1,1'-biphenyl]-4-yl)-1H-1,2,3-triazole-4-carboxamide (5m)

Following the general procedure, the 2-chlorobenzyl analogue was obtained (12 mg, 35% yield) as a white solid. $^1$H NMR (400 MHz, DMSO-d$_6$) δ 10.54 (s, 1H), 8.78 (s, 1H), 7.89 (d, J=8.4 Hz, 2H), 7.62-7.50 (m, 5H), 7.47-7.35 (m, 2H), 7.34-7.25 (m, 1H), 7.03 (d, J=8.4 Hz, 2H), 5.83 (s, 2H), 4.44 (bs, 1H), 2.80-2.62 (m, 2H), 2.40-2.15 (m, 5H), 2.05-1.90 (m, 2H), 1.80-1.60 (m, 2H); $^{13}$C NMR (125 MHz, DMSO-d$_6$) δ 158.1, 156.4, 142.9, 137.3, 135.2, 132.9, 132.6, 132.2, 130.6, 130.4, 129.7, 127.8, 127.4, 126.2, 120.7, 116.2, 71.5, 52.2, 51.0, 45.5, 30.2; HRMS (TOF-ESI) calcd for C$_{28}$H$_{29}$ClN$_5$O$_2$ [M+H]$^+$: 502.2010; found: 502.2008.

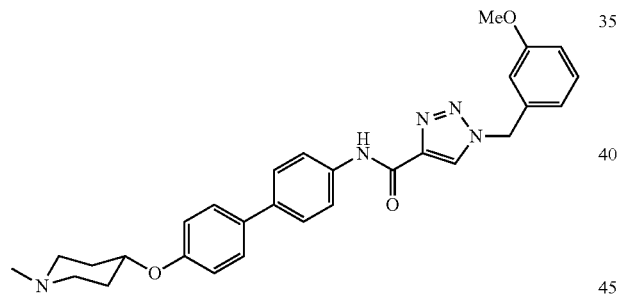

1-(3-Methoxybenzyl)-N-(4'-((1-methylpiperidin-4-yl)oxy)-[1,1'-biphenyl]-4-yl)-1H-1,2,3-triazole-4-carboxamide (5l)

Following the general procedure, the title compound was obtained as a white solid (14 mg, 42% yield). $^1$H NMR (400 MHz, CDCl$_3$ with MeOD) δ 8.12 (s, 1H), 7.70-7.65 (m, 2H), 7.51-7.43 (m, 4H), 7.28-7.23 (m, 2H), 6.94-6.88 (m, 2H), 6.88-6.81 (m, 2H), 6.79-6.76 (m, 1H); 5.50 (s, 2H), 4.62-4.50 (m, 1H), 3.74 (s, 3H), 3.10-2.94 (m, 2H), 2.62 (s, 3H), 2.36-2.18 (m, 2H), 2.14-2.00 (m, 2H); $^{13}$C NMR (125 MHz, CDCl$_3$) δ 160.2, 157.7, 156.8, 143.7, 137.0, 136.1, 134.9, 133.2, 130.5, 127.9, 127.2, 125.7, 120.4, 120.1, 116.3, 114.5, 114.0, 71.9, 55.3, 54.6, 52.5, 46.1, 30.7; HRMS (TOF-ESI) calcd for C$_{29}$H$_{32}$N$_5$O$_3$ [M+Na]$^+$: 498.2505, found: 498.2510.

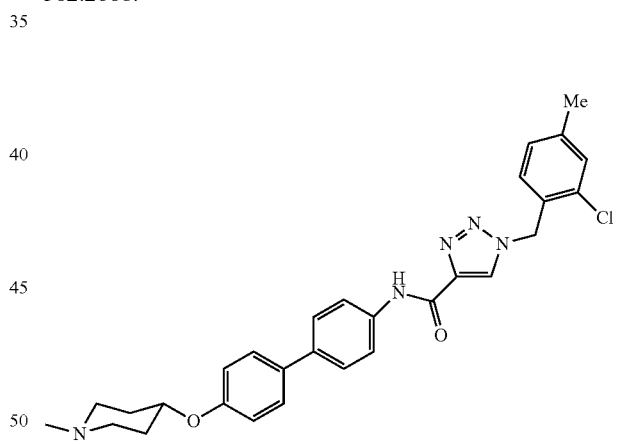

1-(2-Chloro-4-methylbenzyl)-N-(4'-((1-methylpiperidin-4-yl)oxy)-[1,1'-biphenyl]-4-yl)-1H-1,2,3-triazole-4-carboxamide (5n)

Following the general procedure, the title compound was obtained as a white solid (17 mg, 49% yield). $^1$H NMR (400 MHz, CDCl$_3$) δ 8.98 (s, 1H), 8.13 (s, 1H), 7.78-7.72 (m, 2H), 7.60-7.49 (m, 4H), 7.32-7.30 (m, 1H), 7.25-7.21 (m, 1H), 7.16-7.10 (m, 1H), 7.02-6.96 (m, 2H), 5.70 (s, 2H), 7.44-7.34 (m, 1H), 2.85-2.67 (m, 2H), 2.38 (s, 3H), 2.35 (s, 3H), 2.40-2.28 (m, 2H); $^{13}$C NMR (125 MHz, CDCl$_3$) δ 157.7, 156.9, 143.5, 141.5, 137.0, 136.1, 133.7, 133.1, 130.71, 130.65, 128.5, 128.3, 127.9, 127.2, 125.8, 120.1, 116.3, 72.1, 52.6, 51.8, 46.2, 30.8, 21.0; HRMS (TOF-ESI) calcd for $C_{29}H_{31}ClN_5O_2$ [M+H]$^+$: 516.2166; found: 516.2160.

1-(Cyclohexylmethyl)-N-(4'-((1-methylpiperidin-4-yl)oxy)-[1,1'-biphenyl]-4-yl)-1H-1,2,3-triazole-4-carboxamide (5o)

Following the general procedure, the title compound was obtained as a white solid (19 mg, 59% yield). $^1$H NMR (400 MHz, CDCl$_3$) δ 8.98 (s, 1H), 8.11 (s, 1H), 7.74 (d, J=8.8 Hz, 2H), 7.56 (d, J=8.4 Hz, 2H), 7.51 (d, J=8.4 Hz, 2H), 6.98 (d, J=8.8 Hz, 2H), 4.50-4.34 (m, 1H), 4.27 (d, J=7.2 Hz, 2H), 2.83-2.67 (m, 2H), 2.48-2.30 (m, 5H), 2.05-2.00 (m, 2H), 2.00-1.80 (m, 2H), 1.80-1.58 (m, 6H), 1.34-1.10 (m, 4H), 1.10-0.95 (m, 2H); $^{13}$C NMR (125 MHz, CDCl$_3$) δ 157.9, 156.8, 143.3, 137.0, 136.2, 133.3, 127.9, 127.2, 126.0, 120.1, 116.3, 57.0, 52.2, 45.8, 38.7, 30.4, 26.0, 25.4; HRMS (TOF-ESI) calcd for $C_{28}H_{36}N_5O_2$ [M+H]$^+$: 474.2869; found: 474.2860.

All of the compounds, formulations, and methods disclosed and claimed herein can be made and executed without undue experimentation in light of the present disclosure. While the compounds, formulations, and methods of this invention have been described in terms of preferred embodiments, it will be apparent to those of skill in the art that variations may be applied to the compounds, formulations, and methods, as well as in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

ATCC Cell Line Product Information, www.atcc.org, 2015.
Burlison, et al., *J. Am. Chem. Soc.*, 128:15529, 2006.
Burlison, et al., *J. Org. Chem.*, 73:2130, 2008.
Chavez, et al., *Breast Dis.*, 32(1-2):35-48, 2010.
*Handbook of Pharmaceutical Salts: Properties, and Use*, Stahl and Wermuth Eds.), Verlag Helvetica Chimica Acta, 2002.
Horoszewicz, et al., *Cancer Res.*, 43(4):1809-1818, 1983.
Kaighn, et al., *Invest. Urol.*, 17(1):16-23, 1979.
Kolarovic, et al., *J. Org. Chem.*, 76(8):2613-2618, 2011.
Kusuma, et al., *Bioorg. Med. Chem.*, 22:1441-1449, 2014.
Lacroix and Leclercq, *Breast Research and Treatment*, 83(3):249-289, 2004.
Lansford, et al., "Head and Neck Cancer," in Human Cell Culture, Volume 2: Cancer Cell Lines, Part 2, Masters and Palsson, Eds., Dordrecht: Kluwer, 185-255, 1999.
*March's Advanced Organic Chemistry: Reactions, Mechanisms, and Structure*, 2007.
Marcu, et al., *J. Natl. Cancer Inst.*, 92:242-248, 2000.
Matts, et al., *ACS Chem. Biol.*, 6:800-807, 2011.
Neve, et al., *Cancer Cell*, 10(6):515-527, 2006.
Peterson and Blagg, *Bioorg Med. Chem. Lett.*, 20:3957-3960, 2010.
Sobel and Sadar, *J. Urol.*, 173(2):342-359, 2005.
Strejan et al., *J. Neuroimmunol.*, 7:27, 1984.
Yu, et al., *J. Am. Chem. Soc.*, 127:12778, 2005.
Yun, et al., *Biochemistry*, 43:8217-8229, 2004.
Zhao and Blagg, *Bioorg. Med. Chem. Lett.*, 23:552-557, 2013.
Zhao et al., *ACS Med. Chem. Lett.*, 1:311-315, 2010.
Zhao, et al., *J. Med. Chem.*, 54:3839-3853, 2011.
Zhao, et al., *ACS Med. Chem. Lett.*, 5:84-88, 2014.

What is claimed is:

1. A compound of the formula:

(I)

wherein:

R$_1$ is alkyl$_{(C≤12)}$, cycloalkyl$_{(C≤12)}$, alkenyl$_{(C≤12)}$, cycloalkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, -alkanediyl$_{(C≤8)}$-cycloalkyl$_{(C≤12)}$, -alkanediyl$_{(C≤8)}$-cycloalkenyl$_{(C≤12)}$, or a substituted version of any of these groups;

R$_2$ is hydrogen, hydroxy, alkyl$_{(C≤12)}$, substituted alkyl$_{(C≤12)}$, cycloalkyl$_{(C≤12)}$, substituted cycloalkyl$_{(C≤12)}$, alkoxy$_{(C≤12)}$, substituted alkoxy$_{(C≤12)}$, cycloalkoxy$_{(C≤12)}$, or substituted cycloalkoxy$_{(C≤12)}$;

R$_3$ is hydrogen, alkyl$_{(C≤12)}$, cycloalkyl$_{(C≤12)}$, substituted alkyl$_{(C≤12)}$, or substituted cycloalkyl$_{(C≤12)}$; and X$_1$ is heterocycloalkyl$_{(C≤12)}$ or substituted heterocycloalkyl$_{(C≤12)}$; or a compound of the formula:

(II)

wherein:
- $R_4$ is alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq8)}$-cycloalkyl$_{(C\leq12)}$, -alkanediyl$_{(C\leq8)}$-cycloalkenyl$_{(C\leq12)}$, or a substituted version of any of these groups;
- $R_5$ and $R_6$ are each independently:
  - amino, cyano, halo, hydroxy, nitro, hydroxysulfonyl, or sulfonamide; or
  - alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, alkoxy$_{(C\leq12)}$, acyl$_{(C\leq12)}$, amido$_{(C\leq12)}$, alkylamino$_{(C\leq12)}$, dialkylamino$_{(C\leq12)}$, alkylsulfonyl$_{(C\leq12)}$, or a substituted version of any of these groups;
- $n_1$ and $n_2$ are each independently 0, 1, 2, 3, or 4; and
- $X_2$ is heterocycloalkyl$_{(C\leq12)}$ or substituted heterocycloalkyl$_{(C\leq12)}$;

or a pharmaceutically acceptable salt thereof.

2. The compound of claim 1, wherein the compound is further defined as:

(III)

wherein:
- $R_1$ is alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, alkanediyl$_{(C\leq8)}$cycloalkyl$_{(C\leq12)}$, -alkanediyl$_{(C\leq8)}$-cycloalkenyl$_{(C\leq12)}$, or a substituted version of any of these groups;
- $R_3$ is hydrogen, alkyl$_{(C\leq12)}$, or substituted alkyl$_{(C\leq12)}$; and
- $X_1$ is heterocycloalkyl$_{(C\leq12)}$ or substituted heterocycloalkyl$_{(C\leq12)}$;

or a pharmaceutically acceptable salt thereof.

3. The compound of claim 1, wherein the compound is further defined as:

(V)

wherein:
- $R_1$ is alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq8)}$-cycloalkyl$_{(C\leq12)}$, -alkanediyl$_{(C\leq8)}$-cycloalkenyl$_{(C\leq12)}$, or a substituted version of any of these groups;

or a pharmaceutically acceptable salt thereof.

4. The compound of claim 1, wherein the compound is further defined as:

(VI)

wherein:
- $R_4$ is alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq8)}$-cycloalkyl$_{(C\leq12)}$, -alkanediyl$_{(C\leq8)}$-cycloalkenyl$_{(C\leq12)}$, or a substituted version of any of these groups; and
- $X_2$ is heterocycloalkyl$_{(C\leq12)}$ or substituted heterocycloalkyl$_{(C\leq12)}$;

or a pharmaceutically acceptable salt thereof.

5. The compound of claim 1, wherein the compound is further defined as:

(VII)

wherein:
- $R_4$ is alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -alkanediyl$_{(C\leq8)}$-cycloalkyl$_{(C\leq12)}$, -alkanediyl$_{(C\leq8)}$-cycloalkenyl$_{(C\leq12)}$, or a substituted version of any of these groups;

or a pharmaceutically acceptable salt thereof.

6. The compound of claim 1, wherein $R_1$ is aryl$_{(C \leq 12)}$ or substituted aryl$_{(C \leq 12)}$.

7. The compound of claim 1, wherein $R_1$ is aralkyl$_{(C \leq 12)}$ or substituted aralkyl$_{(C \leq 12)}$.

8. The compound of claim 1, wherein $R_1$ is -alkanediyl$_{(C \leq 8)}$-cycloalkyl$_{(C \leq 12)}$ or a substituted version of this group.

9. The compound of claim 1, wherein $R_3$ is alkyl$_{(C \leq 12)}$ or substituted alkyl$_{(C \leq 12)}$.

10. The compound of claim 1, wherein $X_1$ is a nitrogen containing heterocycloalkyl$_{(C \leq 12)}$ or a substituted nitrogen containing heterocycloalkyl$_{(C \leq 12)}$.

11. The compound of claim 1, wherein $R_4$ is aryl$_{(C \leq 12)}$ or substituted aryl$_{(C \leq 12)}$.

12. The compound of claim 1, wherein $R_4$ is aralkyl$_{(C \leq 12)}$ or substituted aralkyl$_{(C \leq 12)}$.

13. The compound of claim 1, wherein $R_4$ is -alkanediyl$_{(C \leq 8)}$-cycloalkyl$_{(C \leq 12)}$ or a substituted version of this group.

14. The compound of claim 1, wherein $n_1$ and $n_2$ are each independently 0 or 1.

15. The compound of claim 1, wherein $X_2$ is a nitrogen containing heterocycloalkyl$_{(C \leq 12)}$ or a substituted nitrogen containing heterocycloalkyl$_{(C \leq 12)}$.

16. The compound of claim 1, wherein $X_1$ or $X_2$ is:

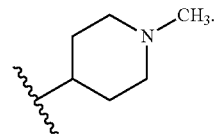 [SMILES: *C1CCN(C)CC1]

17. The compound of claim 1, wherein the compound is further defined as:

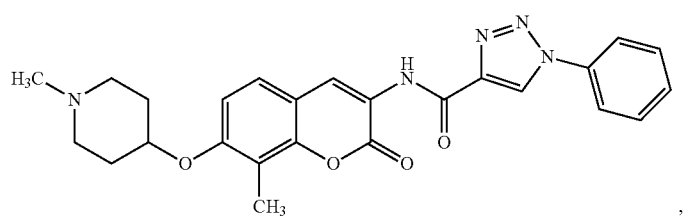

,

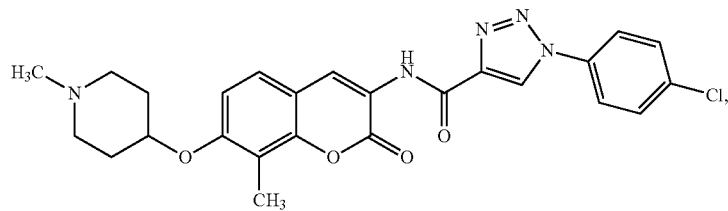

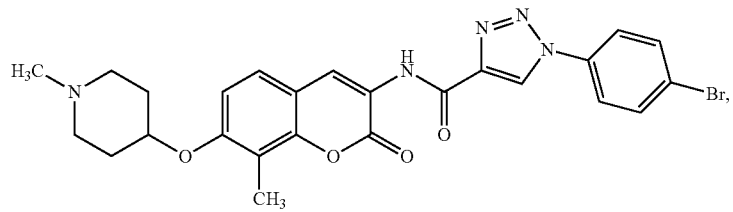

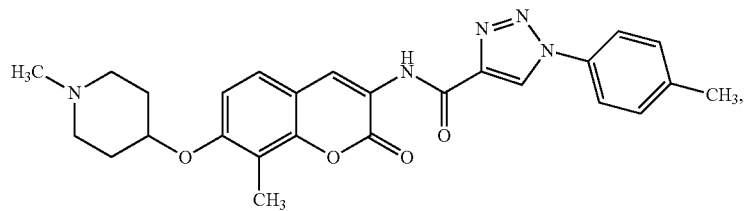

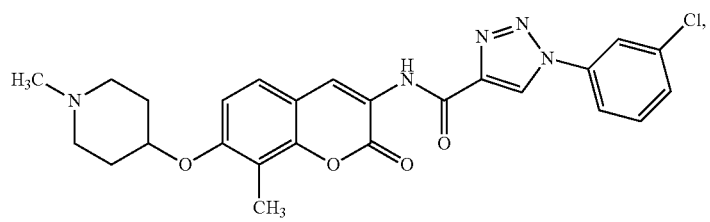

-continued
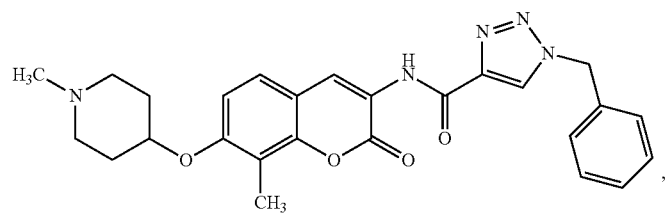
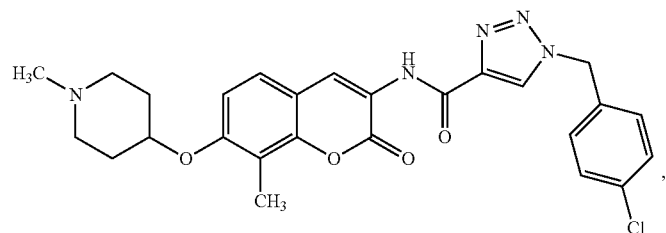
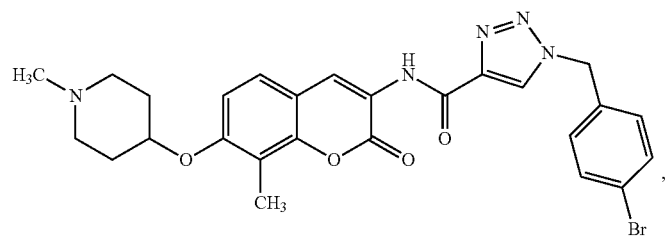
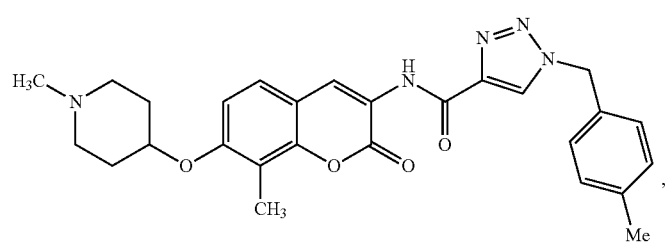
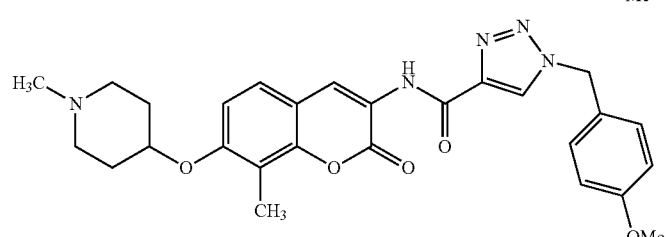
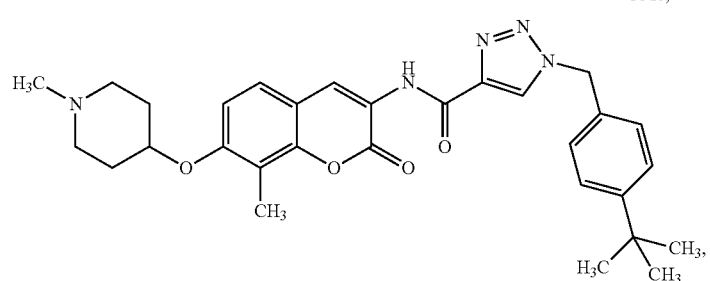
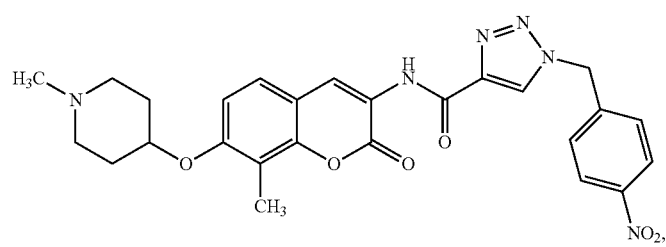

-continued
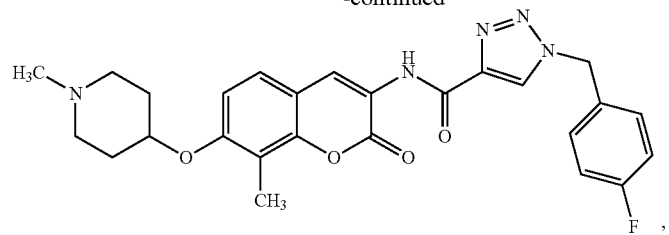
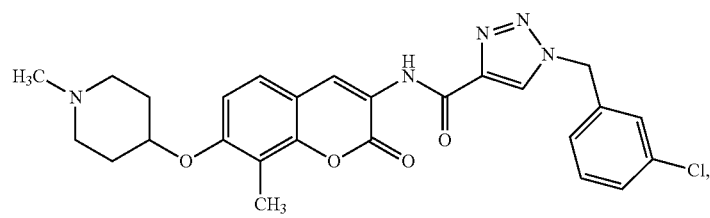
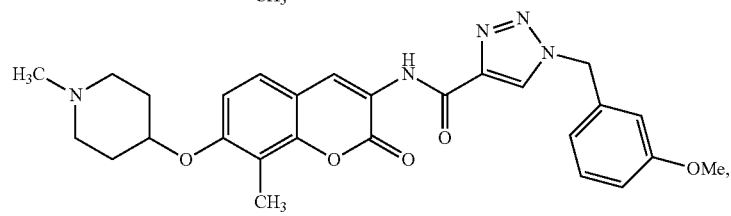
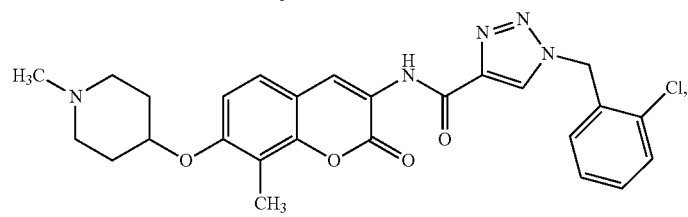
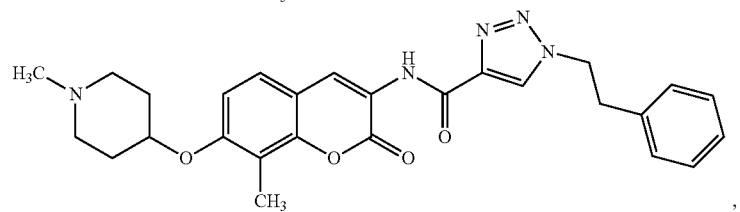
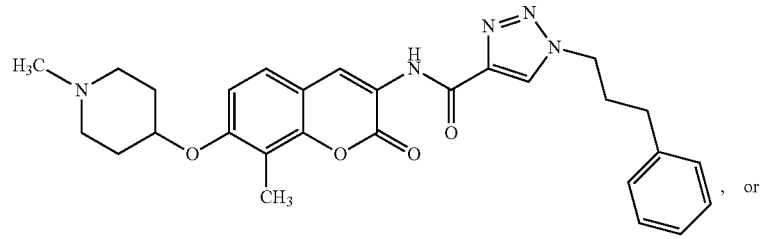, or
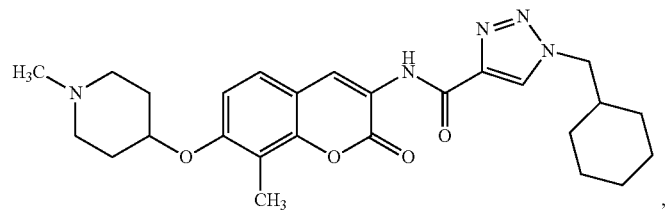,
or a pharmaceutically acceptable salt of any of the above formulas.
18. The compound of claim 1, wherein the compound is further defined as:

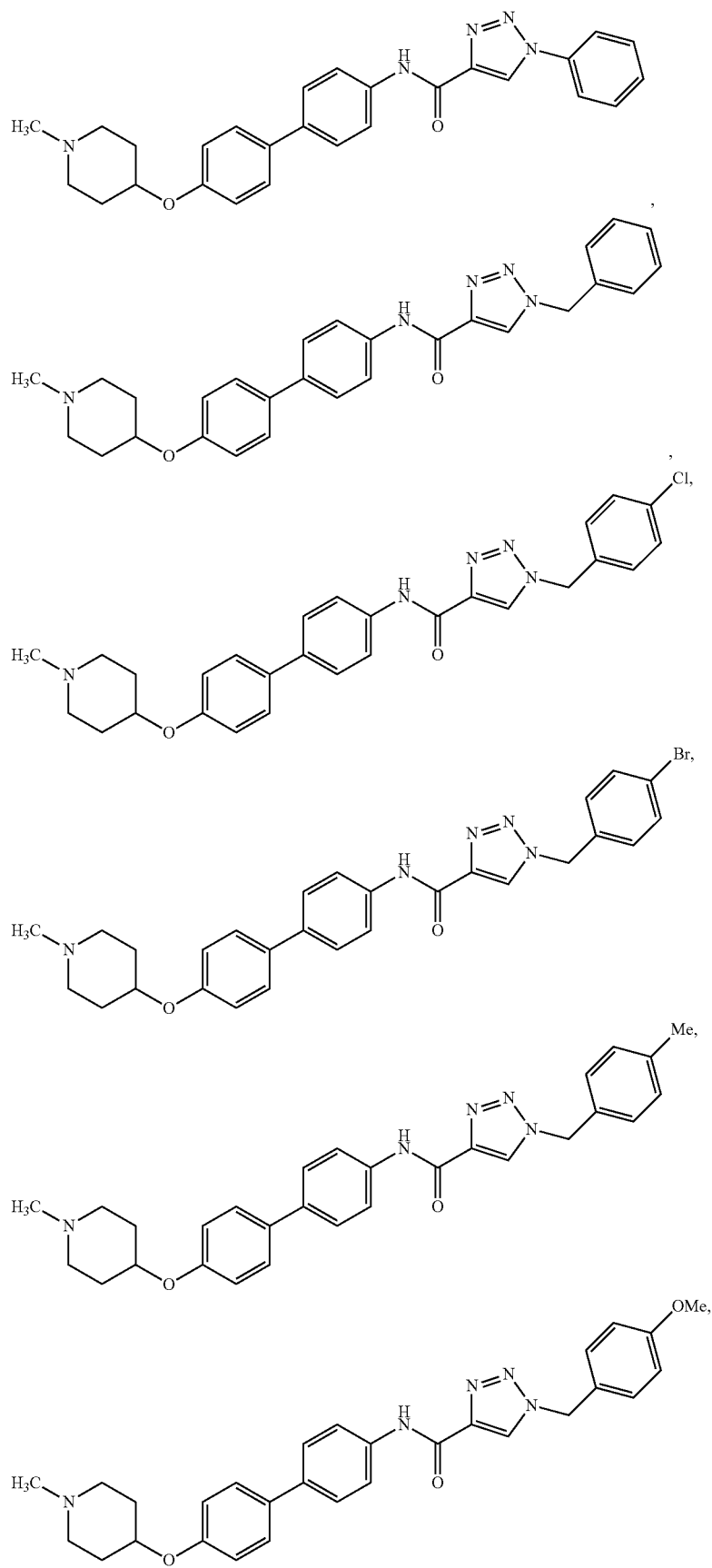 [SMILES: CN1CCC(Oc2ccc(-c3ccc(NC(=O)c4cn(-c5ccccc5)nn4)cc3)cc2)CC1 ; CN1CCC(Oc2ccc(-c3ccc(NC(=O)c4cn(Cc5ccccc5)nn4)cc3)cc2)CC1 ; CN1CCC(Oc2ccc(-c3ccc(NC(=O)c4cn(Cc5ccc(Cl)cc5)nn4)cc3)cc2)CC1 ; CN1CCC(Oc2ccc(-c3ccc(NC(=O)c4cn(Cc5ccc(Br)cc5)nn4)cc3)cc2)CC1 ; Cc1ccc(Cn2cc(C(=O)Nc3ccc(-c4ccc(OC5CCN(C)CC5)cc4)cc3)nn2)cc1 ; COc1ccc(Cn2cc(C(=O)Nc3ccc(-c4ccc(OC5CCN(C)CC5)cc4)cc3)nn2)cc1]

-continued
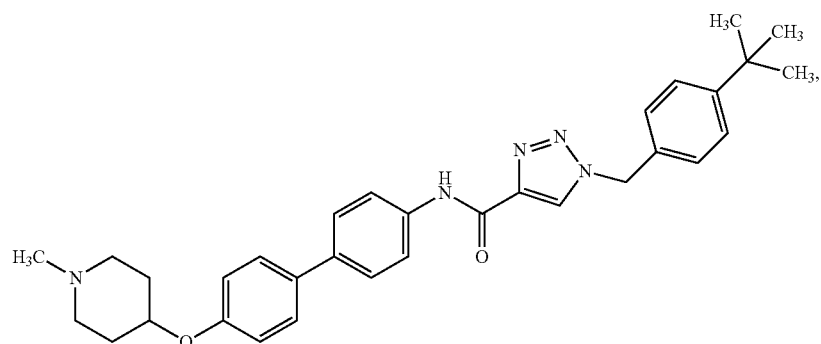
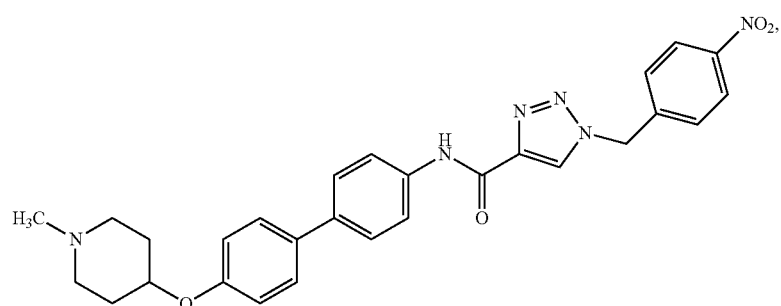
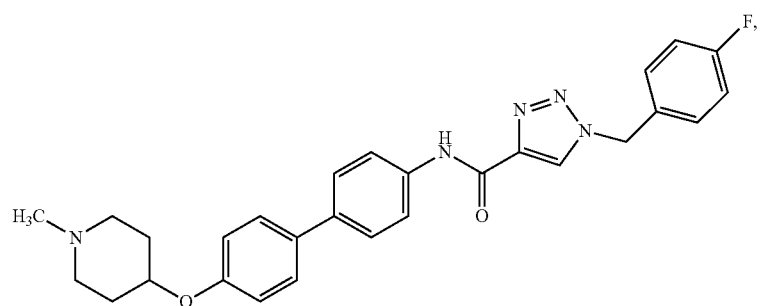
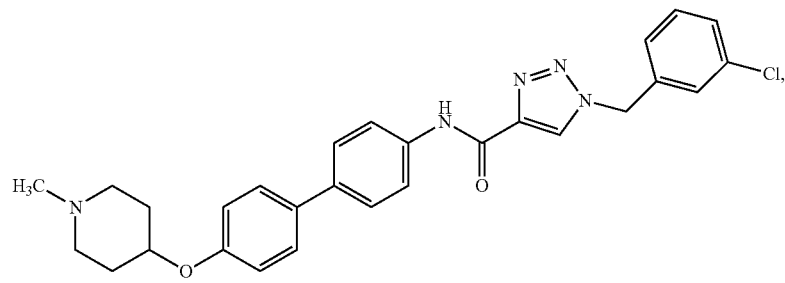
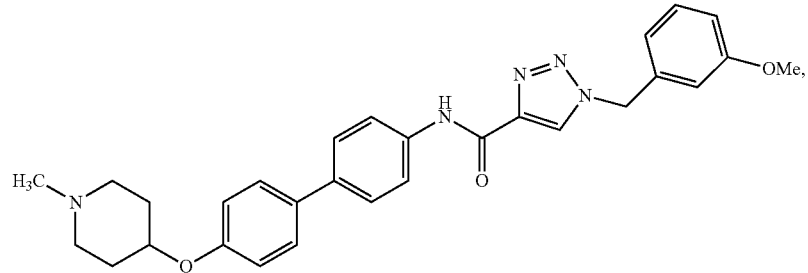

-continued
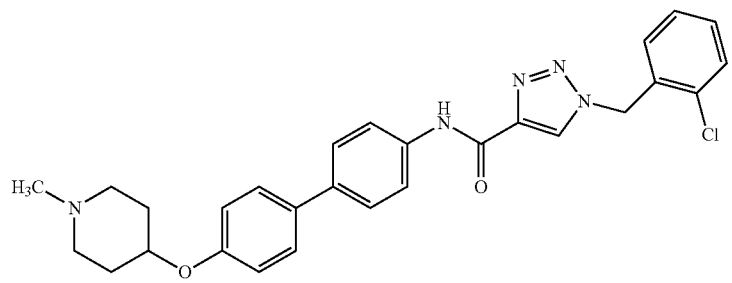
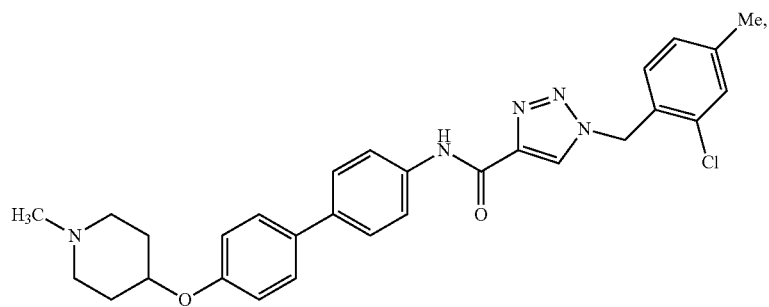
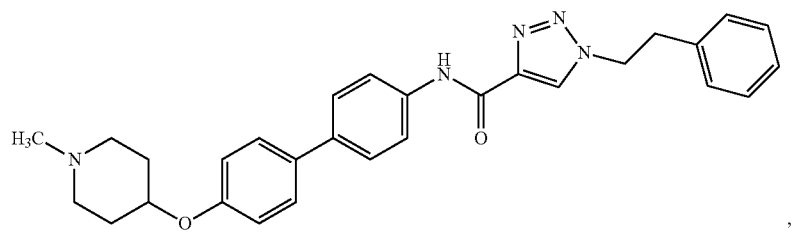
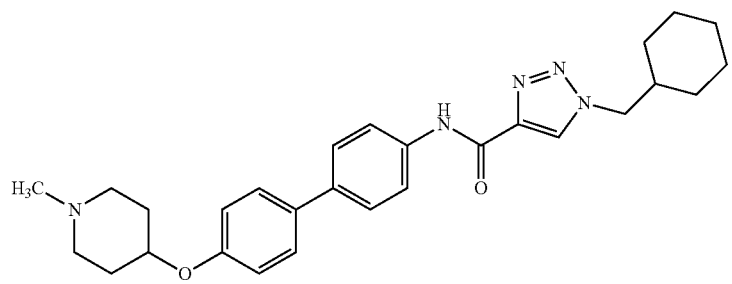
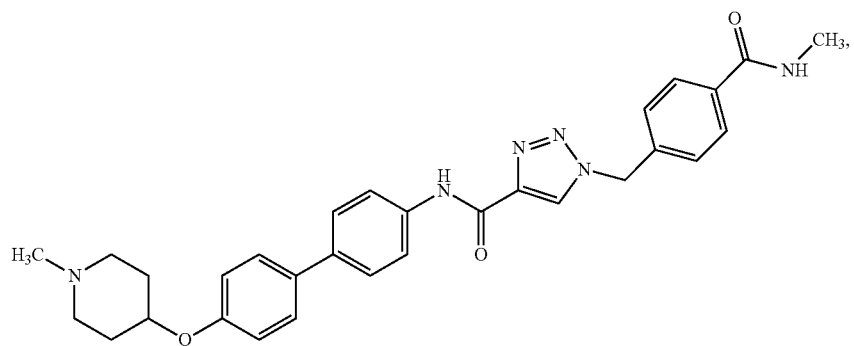

-continued
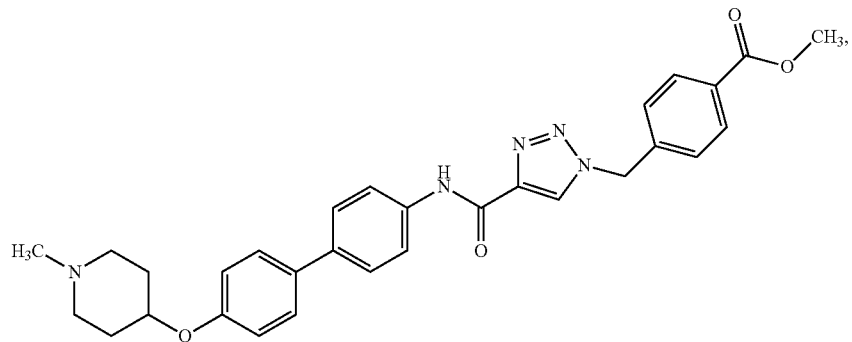
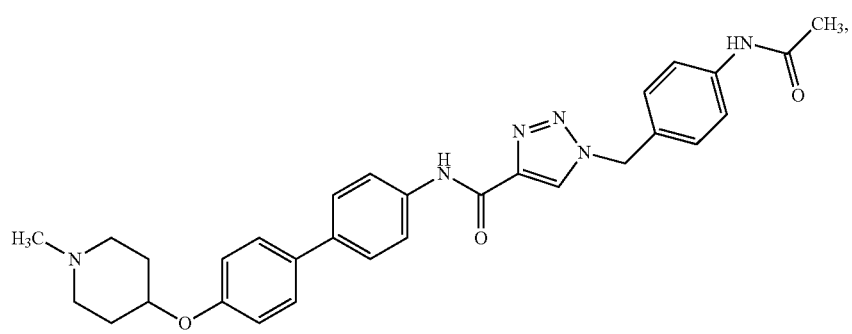
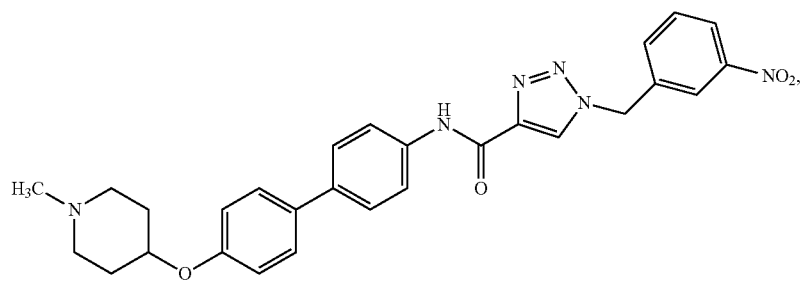
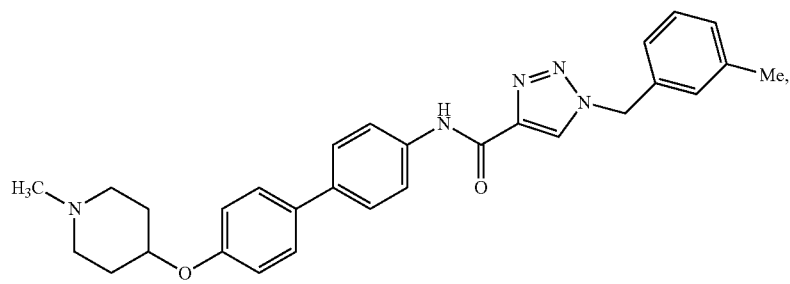
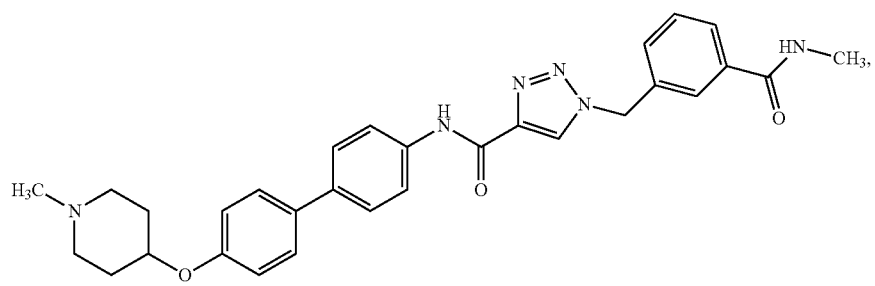

-continued
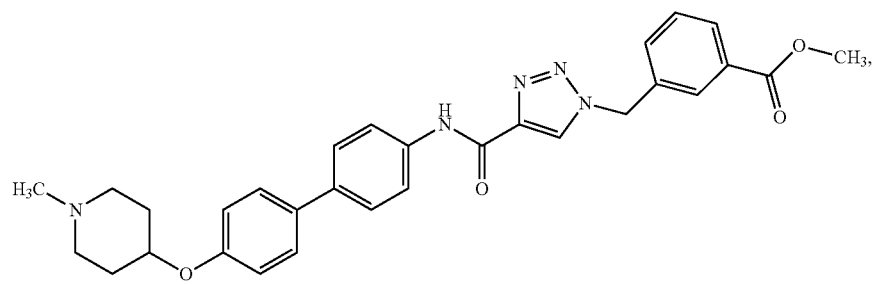
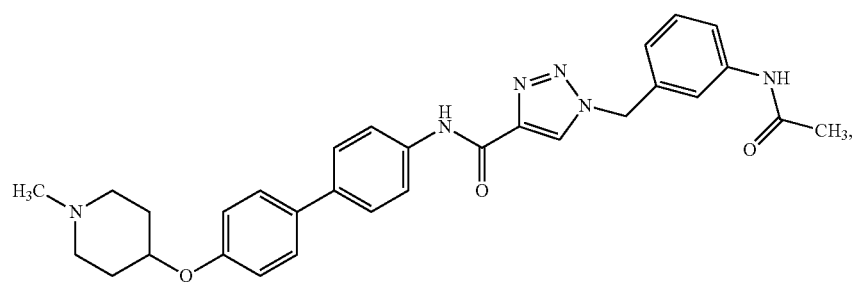
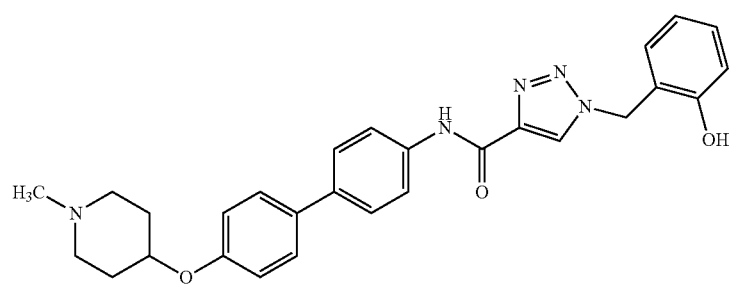
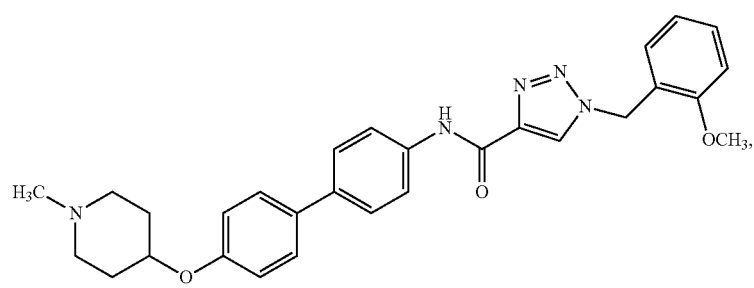
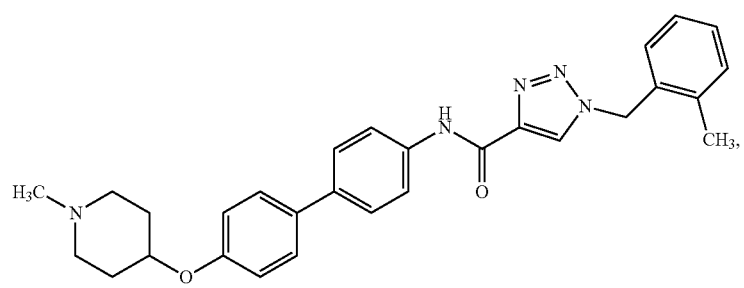
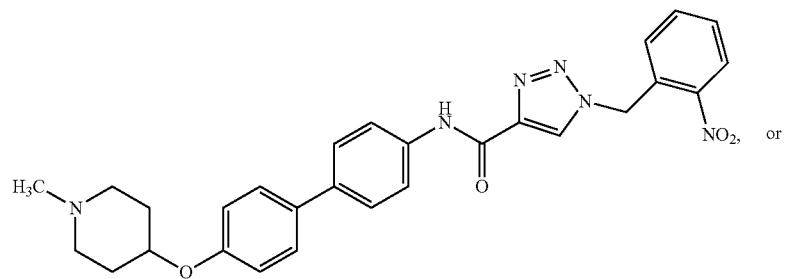

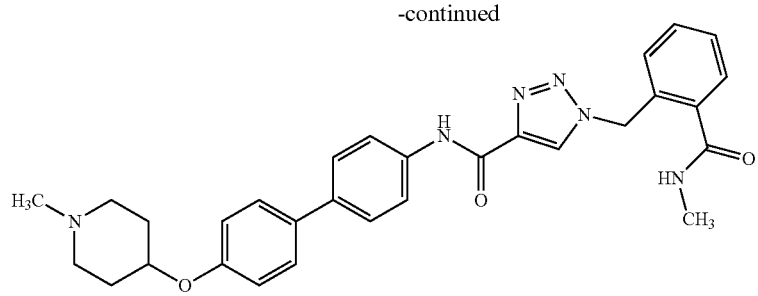
or a pharmaceutically acceptable salt of any of the above formulas.
19. A pharmaceutical composition comprising:
(A) a compound of claim 1; and
(B) a pharmaceutically acceptable carrier.
20. A method of treating cancer in a patient comprising administering to the patient a therapeutically effective amount of a compound of claim 1.
* * * * *